(12) United States Patent
Johnson et al.

(10) Patent No.: US 6,703,400 B2
(45) Date of Patent: Mar. 9, 2004

(54) METHODS FOR TREATING MULTIDRUG RESISTANCE

(75) Inventors: William W. Johnson, Sparta, NJ (US); Er-Jia Wang, Sparta, NJ (US); Christopher Casciano, Newton, NJ (US); Robert P. Clement, Morris Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/104,554

(22) Filed: Mar. 22, 2002

(65) Prior Publication Data

US 2003/0216422 A1 Nov. 20, 2003

Related U.S. Application Data

(60) Provisional application No. 60/271,243, filed on Feb. 23, 2001.

(51) Int. Cl.⁷ ............................................... A61K 31/44
(52) U.S. Cl. .......................... 514/290; 514/34; 514/90; 514/922
(58) Field of Search ........................... 514/90, 34, 290, 514/922

(56) References Cited

U.S. PATENT DOCUMENTS

| 5,416,091 | A |   | 5/1995  | King ........................... 514/290 |
| 5,719,148 | A |   | 2/1998  | Bishop et al. ............... 514/228 |
| 5,728,687 | A | * | 3/1998  | Bissery ........................ 514/90 |
| 5,874,442 | A |   | 2/1999  | Doll et al. ................... 514/290 |
| 5,894,442 | A |   | 4/1999  | Okamura et al. ........... 365/203 |
| 6,096,757 | A |   | 8/2000  | Bishop et al. .............. 514/290 |
| 6,316,462 | B1 |   | 11/2001 | Bishop et al. .............. 514/290 |
| 6,465,448 | B1 | * | 10/2002 | Gerson et al. .............. 514/183 |

FOREIGN PATENT DOCUMENTS

| WO | WO 95/10516 | 4/1995 | ......... C07D/401/04 |
| WO | WO 96/30363 | 10/1996 | ......... C07D/401/04 |

OTHER PUBLICATIONS

U.S. application 09/971,545, filed Oct 5, 2001, "Methods of Inducing Cancer Cell Death and Tumor Regression".
U.S. application 10/303,259, filed Nov. 25, 2002, "Methods of Treating Cancer Using an FPT Inhibitor and Antineoplastic Agents".
Gottesman et al, Annu. Rev. Biochem, 1993 62:385–427.
Johnson et al., The Farnesyl Protein Gransferase Inhibitor SCH66336 Is a Potent Inhibitor of MDR1 Product P–Glycoprotein, Abstract No. 1409 (2001).
Pastan et al, The New England Journal of Medicine 1987, 1388–1393.
Scientific Program 92$^{nd}$ Annual Meeting of the American Association for Cancer Research, New Orleans, LA Mar. 24–28, 2001.
Shapiro et al., The Journal of Biological Chemistry, 1995 270:16167–16175.

\* cited by examiner

*Primary Examiner*—Frederick Krass
(74) *Attorney, Agent, or Firm*—Henry C. Jeanette

(57) ABSTRACT

Methods are provided for treating multidrug resistance in refractory tumor cells comprising administering (1) a P-glycoprotein inhibitor in conjunction with (2) an antineoplastic agent.

1 Claim, 4 Drawing Sheets

METHODS FOR TREATING MULTIDRUG RESISTANCE

FIELD OF THE INVENTION

This invention describes novel methods of treating multiple drug resistance of refractory tumor cells in a patient in need of such treatment, said method comprising the combined use of (1) a P-gp inhibitor and (2) an antineoplastic agent.

BACKGROUND OF THE INVENTION

Resistance to drug therapy thwarts the treatment of many diseases and infections, particularly cancer. A major cause for the observed resistance is the overexpression of transmembrane multidrug resistance transporters (MDR) responsible for pumping structurally diverse antitumor drugs from cells. By ejecting drugs from the cell, these transporter enzymes decrease exposure and hence efficacy. The resistance can be enhanced in mutated or induced cells, including cancer cells which commonly have elevated levels of these transporters.

Over-expression of P glycoprotein ("Pgp," 170–180 kDa), the product of the MDR1 gene, is the most commonly observed characteristic of multidrug resistant cells grown in vitro (Gottesman et al., 1993 Annu. Rev. Biochem 62:385–427; Schinkel et al, 1996, Shapiro et al., 1995, J. Biol. Chem 270: 16167–75 and in a number of tumors (Redmond et al., 1991, Decker et al., 1995).

Cancers which are known to exhibit drug resistance due to overexpression of the multiple drug transporter P-gp include adenocarcinomas derived from adrenal, kidney, liver, small intestine, and colon tissue (Gottes et al., 1987, New England J. Med 1388) pancreatic, carcinoid, chronic myelogenous leukemia in blast crisis, and non-small cell lung carcinoma. Examples of tumor cells which have the ability to overexpress the multidrug transporter protein upon selection by an antineoplastic agent include neuroblastoma cells, pheochromocytoma cells, multiple myeloma, adult acute lymphocytic leukemia cells, adult acute nonlymphocytic leukemia cells, nodular poorly differentiated lymphoma cells, breast cancer cells and ovarian and cervical cancer cells.

A large number of compounds that interact with the Pgp efflux pump have been identified and some are under development as drugs. These compounds have no common chemical structural features except for hydrophobicity. Some of them are positively charged at physiological pH (Chin, 1993). The early generation of modulators of Pgp, such as cyclosporin A (Sonneveld et al., 1992), verapamil (Watanabe et al., 1995) and quinidine (Wishart et al., 1992) failed to show clinical significance due to limited efficacy and their own dose related toxicity or profound alterations in pharmacokinetics when used in combination with anticancer drugs. The more recently developed modulators possess a higher affinity for Pgp, however their efficacy is still under clinical evaluation. Examples of this class include the cyclosporin A analog PSC 833 (Keller et al., 1992), the acridonecarboximide GF120918 (Hyafil et al., 1993), LY335979 (Slate, et al.1995), the triazinoaminopiperidine derivative S9788 (Merlin et al., 1995), a yohimbine analog, trimethoxybenzoylyohimbine (Pearce et al., 1989) and other compounds including MS-073 (Sato et al., 1991) and R-isomer of verapamil (Toffoli et al., 1995).

International Patent Publication Number WO92/11034 (published Jul. 9, 1992) (U.S. Pat. No. 5,416,091) discloses a method of inhibiting multiple drug resistance, by the concurrent administration of an antineoplastic agent and (inter alia) a potentiating agent of the formula:

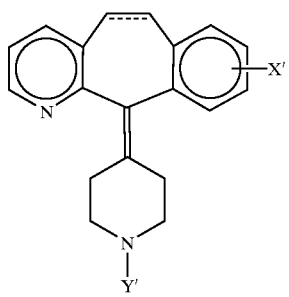

A wherein the dotted line represents an optional double bond, X' is hydrogen or halo, and Y' is hydrogen, substituted carboxylate or substituted sulfonyl. For example, Y' can be, amongst others, —COOR' wherein R' is C-1 to C-6 alkyl or substituted alkyl, phenyl, substituted phenyl, C-7 to C-12 aralkyl or substituted aralkyl, 2-, 3- or 4-piperidyl or N-substituted piperidyl. Y' can also be, amongst others, SO$_2$R' wherein R' is C-1 to C-6 alkyl, phenyl, substituted phenyl, C-7 to C-12 aralkyl or substituted aralkyl. Examples of such potentiating agents include 11-(4-piperidyl-dene)-5H-benzo[5,6]cyclohepta[1,2-b]pyridines such as Loratadine. Antineoplastic agents exemplified are: vinca alkaloids, epipodophyllotoxins, anthracycline antibiotics, actinomycin D, plicamycin, puromycin, gramicidin D, taxol, colchicine, cytochalasin B, emetine, maytansine, and amsacrine.

SCH66336 is a tricyclic small molecule which was originally identified as a potent and selective inhibitor of the farnesyl protein transferase (FPT) enzyme. (U.S. Pat. No. 5,874,442; see also U.S. Pat. No. 5,719,148). The antitumor activity of SCH66336 includes inhibition of anchorage-indepent growth of a variety of human tumor cell lines in vitro and their growth as xenografts in immunocompromised mice (Liu et al., 1998).

In view of the need for improved treatments for multiple drug resistance, novel methods of treatment would be a welcome contribution to the art. The present invention provides just such methods of treatment.

SUMMARY OF THE INVENTION

The present invention is based on the surprising discovery that SCH66336 and compounds in the same structural series are potent inhibitors of the P-gp transporter enzyme. The invention provides methods of treating multidrug resistance of refractory tumor cells in a patient (e.g., a mammal such as a human) in need of such treatment, said treatment comprising administering, concurrently or sequentially, an effective amount of (1) P-glycoprotein (P-gp) inhibitor, and (2) an antineoplastic agent. The methods of the present invention are particularly useful for the treatment of various cancers, especially adenocarcinoma cells derived from adrenal, kidney, liver, small intestine, and colon tissue, pancreatic, carcinoid, chronic myelogenous leukemia in blast crisis, non-small cell lung carcinoma, neuroblastoma cells, pheochromocytoma cells, multiple myeloma, adult acute lymphocytic leukemia cells, adult acute nonlymphocytic leukemia cells, nodular poorly differentiated lymphoma cells, ocular melanoma cells, skin melanoma cells, uterine melanoma cells, breast cancer cells and ovarian cancer cells, and metastatic cells.

In preferred embodiments, the P-gp inhibitor is combined with one of the following antineoplastic agents:

gemcitabine, paclitaxel (Taxol®), 5-Fluorouracil (5-FU), cyclophosphamide (Cytoxan®), temozolomide, or Vincristine, docetaxel.

For instance, in a preferred embodiment, the present invention provides a method of treating multi-drug resistance comprising administering, concurrently or sequentially, an effective amount of (1) a P-gp inhibitor, and (2) gemcitabine. In a particularly preferred embodiment, the cancer to be treated is a pancreatic cancer.

In a particularly preferred embodiment, the present invention provides a method of treating multi-drug resistance, comprising administering, concurrently or sequentially, an effective amount of (1) the P-gp inhibitor SCH66336, and (2) an antineoplastic agent.

BRIEF DESCRIPTION OF THE DRAWINGS

The P-gp Inhibitory Compound in FIGS. 1 through 4 (sometimes referred to as "SCH66336") is as follows:

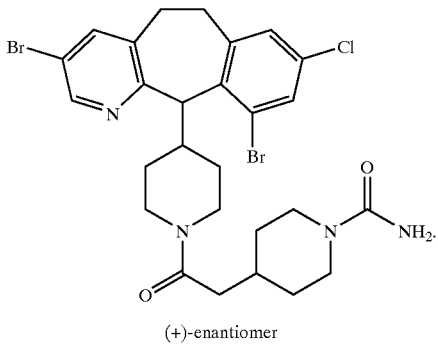

(+)-enantiomer

Figure 1:
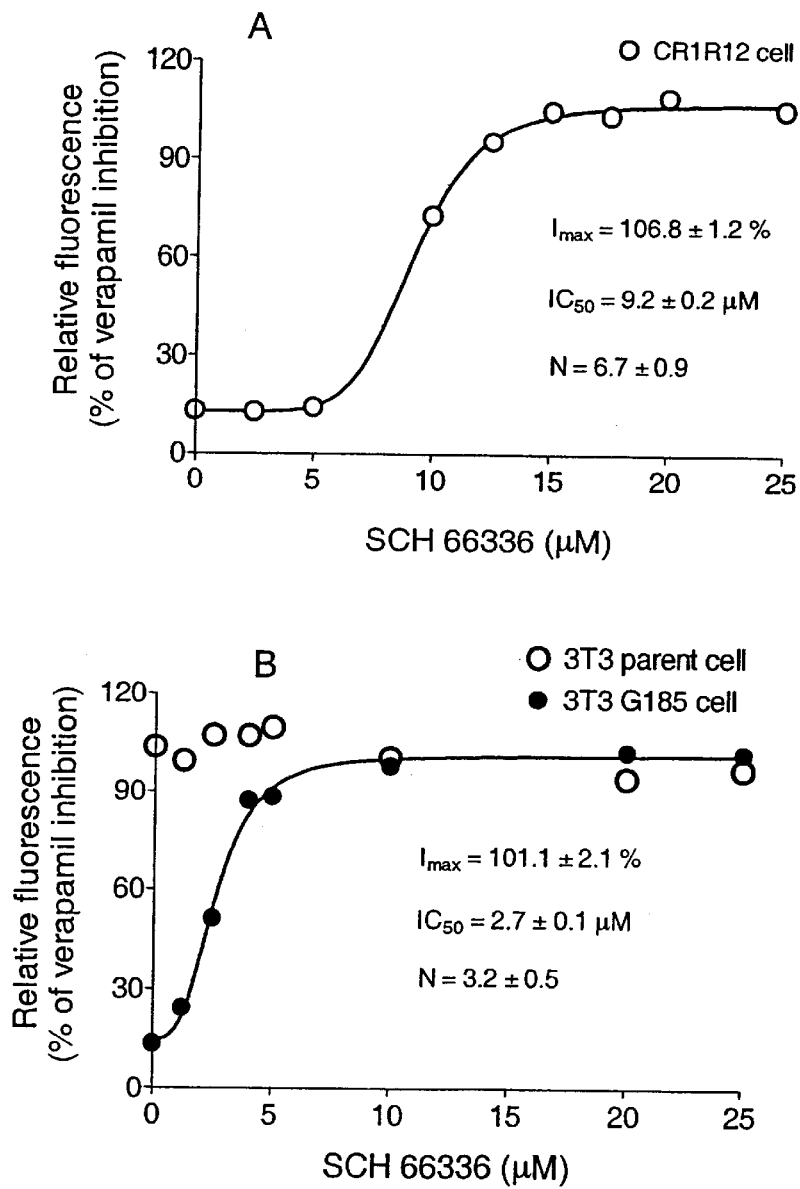

FIG. 1 shows intracellular retention of daunorubicin fluorescence (a & b) in CR1R12 cells (FIG. 1A) and G185 cells (FIG. 1B) versus competing SCH 66336 concentration. Fluorescence intensity of cells is expressed as relative fluorescence (channel numbers) and plotted against SCH66336 concentration. The efflux phase or incubation was 30 min in all cases. The average number of cells per assay was 10,000. The function for the line through the data is the Hill equation: $v=V_{max}S^n/(K'+S^n)$. The parameters IC50 and the Hill coefficient along with the standard deviation are shown on the respective graphs.

Figure 2:
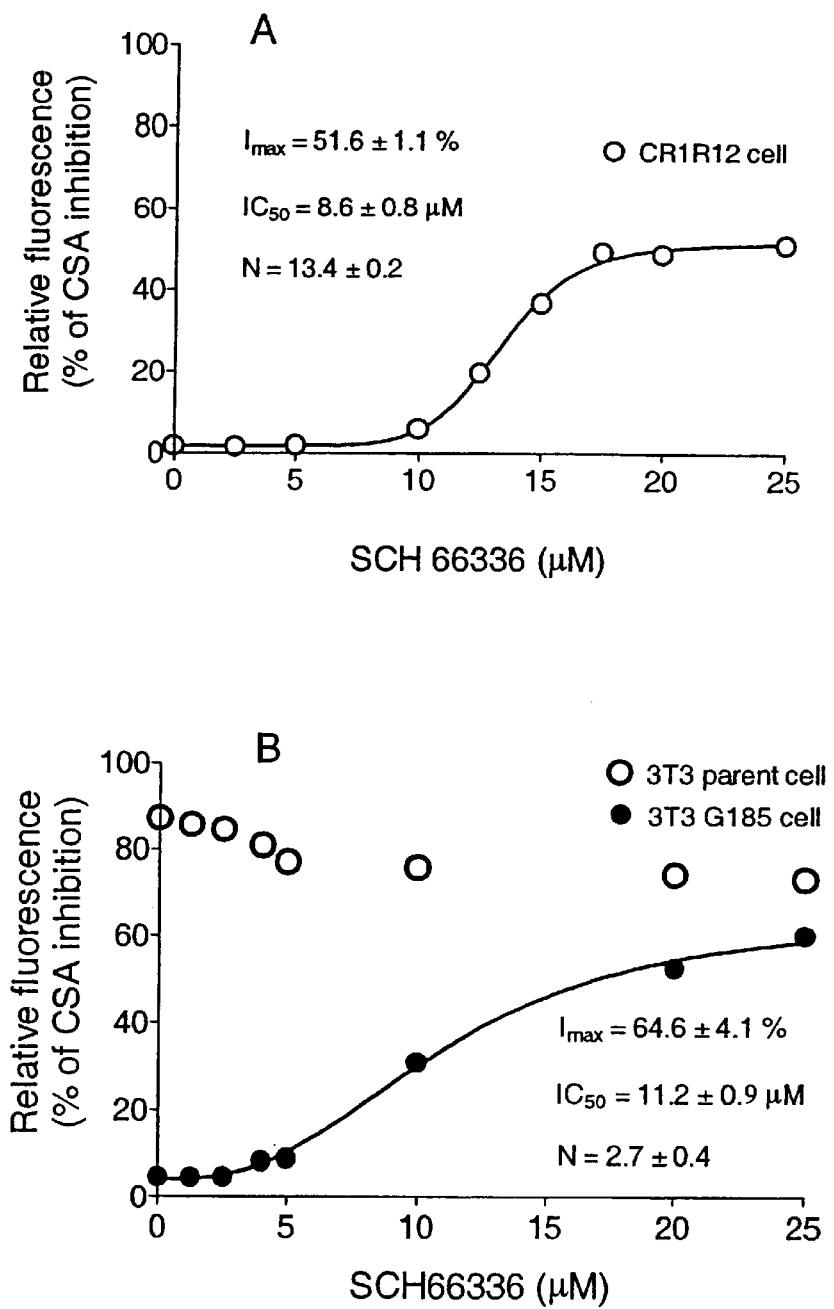

FIG. 2 shows P-gp-mediated ATP hydrolysis rates in the presence of SCH 6336. ATP hydrolysis as nmol/min/mg is plotted against SCH66336 concentration. The data is fit to a hyperbola (Michaelis-Mentin kinetics) (FIG. 2A) and the $V_{max}=28\%$ of control with a $K_m=3.2\pm1$ mM (FIG. 2B).

Figure 3:
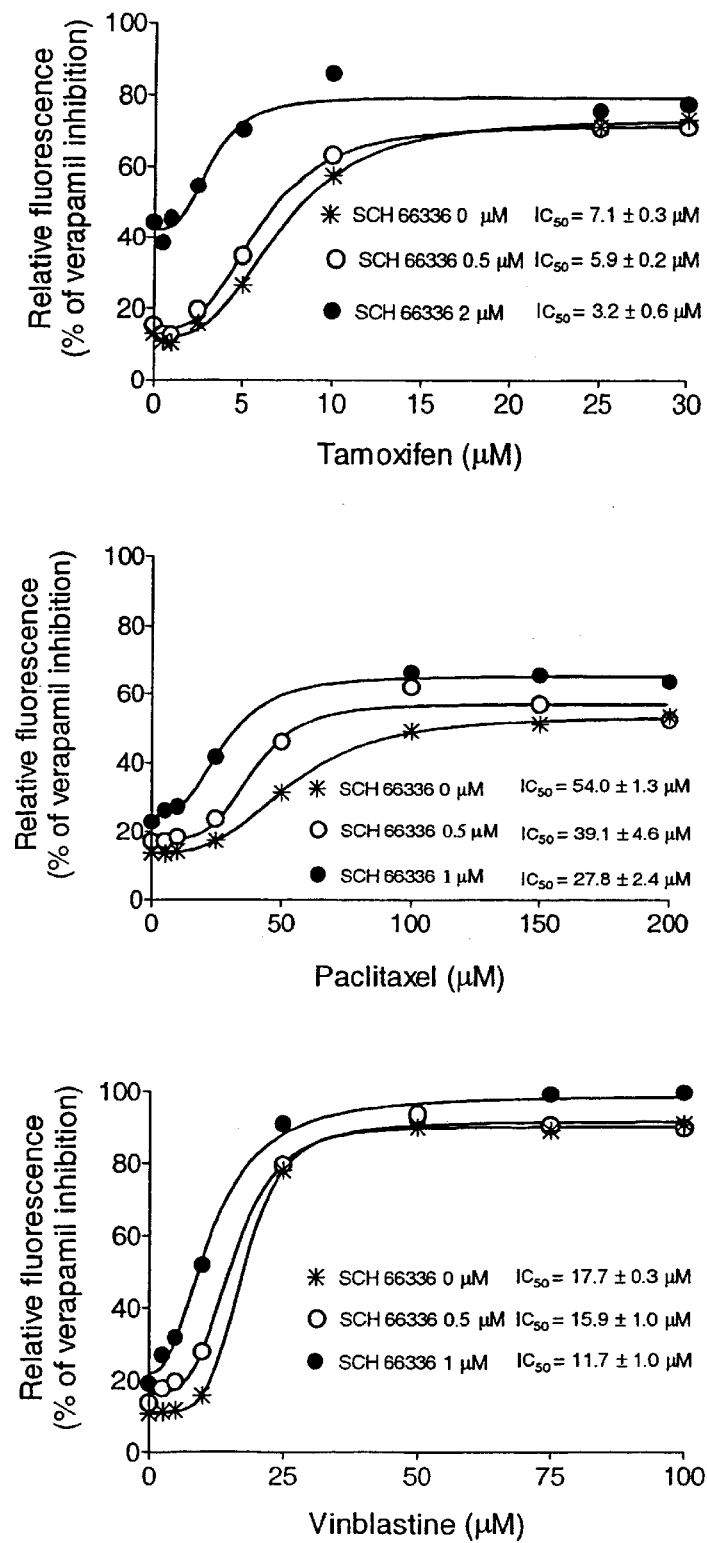

FIG. 3 graphically shows the decrease in IC50 comparing Tamoxifen, Paclitaxel and Vinblastine.

Figure 4:
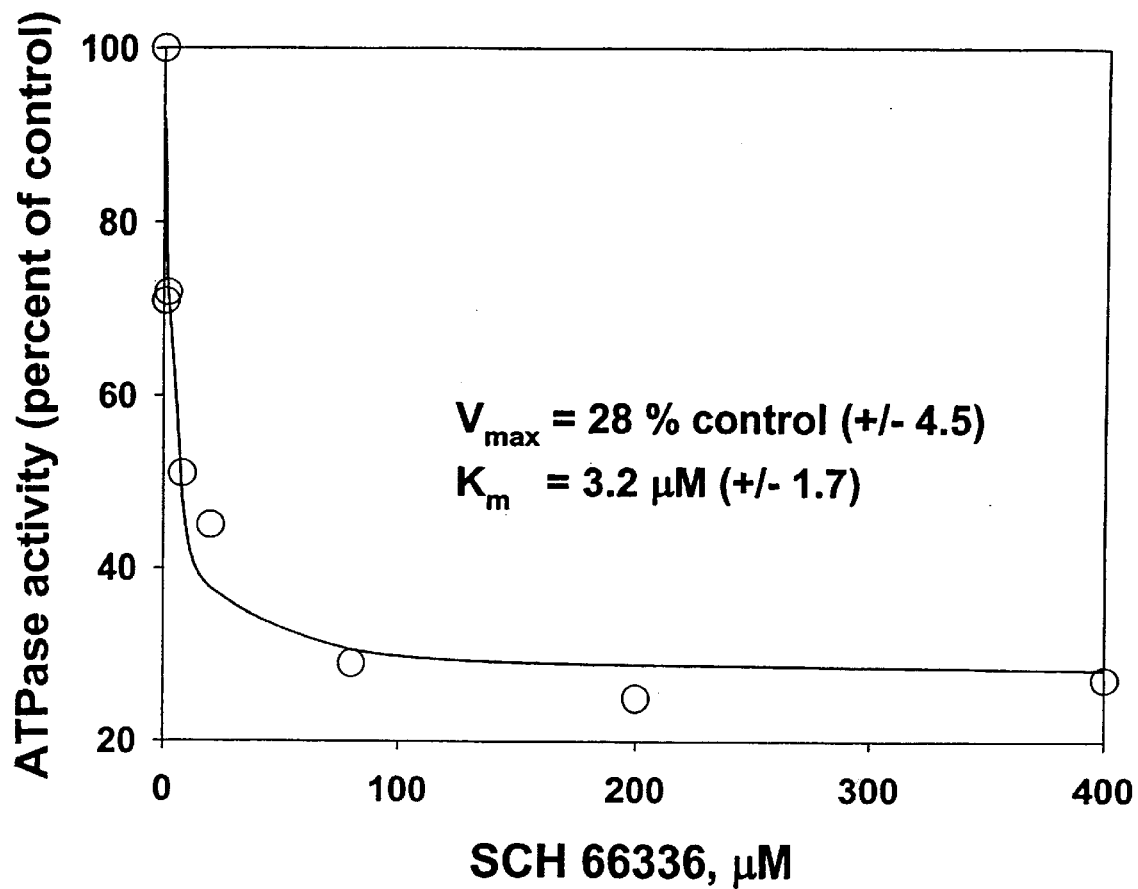

FIG. 4 graphically shows the P-gp-mediated ATP hydrolysis rates in the presence of SCH 66336.

DETAILED DESCRIPTION OF THE INVENTION

The present invention is based on the surprising and unexpected discovery that the FPT inhibitor SCH 66336 is an effective, potent antagonist of the MDR1 (p-glycoprotein) transporter enzyme, the most ubiquitous of MDR transporters (referred to hereinafter as "P-gp"). Thus, SCH 66336 and P-gp inhibitors in the same structural series have a novel therapeutic benefit in overcoming multidrug resistance in refractory tumor cells. By impeding the ability of these transporters to remove drugs from the cell, P-gp antagonists such as SCH 66336 and the compounds in this series can prolong and increase exposure to drugs of various therapeutic classes, including those for treatment of cancer.

The present invention provides methods for treating multidrug resistance of refractory tumor cells in a patient in need of such treatment (e.g., a mammal such as a human), by administering, concurrently or sequentially, an effective amount of a P-gp inhibitor and an effective amount of a chemotherapeutic agent. The method for treating multidrug resistance according to the invention includes a method for inhibiting the P-gp transporter enzyme expressed on the surface of refractory tumor cells.

"Refractory tumor cells" means tumor cells which have elevated levels of P-gp tranport enzymes on the cell surface. In addition to those tumor cells listed herein as having elevated levels of P-gp transport enzymes on the cell surface, the term "refractory tumor cells" also included tumor cells that are determined to express elevated levels of P-gp by standard methods.

In preferred embodiments, the methods of the present invention include methods for treating multidrug resistance of refractory tumor cells in a patient in need of such treatment (e.g., a mammal such as a human) by administering, concurrently or sequentially, (1) an effective amount of a P-gp inhibitor and (2) an effective amount of an antineoplastic agent. Examples of refractory tumor cells which may be treated include, but are not limited to, adenocarcinoma cells derived from adrenal, kidney, liver, small intestine, and colon tissue, pancreatic, carcinoid, chronic myelogenous leukemia in blast crisis, non-small cell lung carcinoma, neuroblastoma cells, pheochromocytoma cells, multiple myeloma, adult acute lymphocytic leukemia cells, adult acute nonlymphocytic leukemia cells, nodular poorly differentiated lymphoma cells ocular melanoma cells, skin melanoma cells, uterine melanoma cells, breast cancer cells and ovarian cancer cells, and metastatic cells.

As used herein the following terms have the following meanings unless indicated otherwise:

antineoplastic agent—a chemotherapeutic agent effective against cancer;

concurrently—(1) simultaneously in time, or (2) at different times during the course of a common treatment schedule; and sequentially—(1) administration of one component of the method ((a) P-GP inhibitor, or (b) antineoplastic agent and/or radiation therapy) followed by administration of the other component; after administration of one component, the second component can be administered substantially immediately after the first component, or the second component can be administered after an effective time period after the first component; the effective time period is the amount of time given for realization of maximum benefit from the administration of the first component.

Chemotherapeutic Agents

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxyco-formycin, Mitomycin-C, L-Asparaginase, Interferons (especially IFN-a), Etoposide, and Teniposide.

Hormones and steroids (including synthetic analogs): 17-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

Microtubule Affecting Agents

The present invention also provides methods of treating diseased cells by contacting the cells with a P-GP inhibitor and a microtubule affecting agent (e.g., paclitaxel, a paclitaxel derivative or a paclitaxel-like compound). As used herein, a microtubule affecting agent is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) *Science*, 274:2009) estramustine, nocodazole, MAP4, and the like. Examples of such agents are also described in the scientific and patent literature, see, e.g., Bulinski (1997) *J. Cell Sci.* 110:3055–3064; Panda (1997) *Proc. Natl. Acad. Sci. USA* 94:10560–10564; Muhiradt (1997) *Cancer Res.* 57:3344–3346; Nicolaou (1997) *Nature* 387:268–272; Vasquez (1997) *Mol. Biol Cell.* 8:973–985; Panda (1996) *J. Biol. Chem.* 271:29807–29812.

Particularly preferred agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos: 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) *Oncology*, 6: 17–23, Horwitz (1992) *Trends Pharmacol. Sci.* 13: 134–146, Rowinsky (1990) *J. Natl. Canc. Inst.* 82: 1247–1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) *Cancer Chemother. Pharmacol.* 41:37–47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

In a preferred embodiment, compounds with possible tubulin polymerization activity are screened in vitro. In a preferred embodiment, the compounds are screened against cultured WR21 cells (derived from line 69–2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) *Lab. Anim. Sci.*, 45(2):145–150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) *J. Molec. Biol.*, 89: 737–758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

P-gp Inhibitors-Exemplified Compounds

The following documents disclose compounds that are P-gp inhibitors that can be used in this invention. The radicals and formulae designations defined herein for a particular document apply only to the compounds described in that document.

U.S. Pat. No. 5,719,148, issued Feb. 17, 1998 (see also WO 95/10516 published Apr. 20, 1995 and WO 96/30363 published Oct. 3, 1996, the disclosures of which are expressly incorporated herein by reference) disclose compounds of formula 1.0:

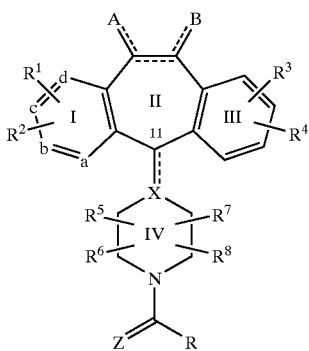

(1.0)

or a pharmaceutically acceptable salt or solvate thereof, wherein:
one of a, b, c and d represents N or $NR^9$ wherein $R^9$ is O—, —$CH_3$ or —$(CH_2)_nCO_2H$ wherein n is 1 to 3, and the remaining a, b, c and d groups represent $CR^1$ or $CR^2$; or each of a, b, c, and d is independently selected from $CR^1$ and $CR^2$;

each $R^1$ and each $R^2$ is independently selected from H, halo, —$CF_3$, —$OR^{10}$, —$COR^{10}$, —$SR^{10}$, —$S(O)_tR^{11}$ (wherein t is 0, 1 or 2), —SCN, —$N(R^{10})_2$, —$NO_2$, —$OC(O)R^{10}$, —$CO_2R^{10}$, —$OCO_2R^{11}$, —CN, —NHC(O)$R^{10}$, —$NHSO_2R^{10}$, —$CONHR^{10}$, —$CONHCH_2CH_2OH$, —$NR^{10}COOR^{11}$, —$SR^{11}C(O)OR^{11}$,

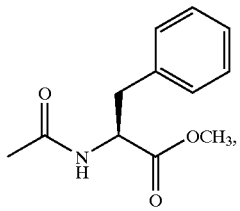

—$SR^{11}N(R^{75})_2$ (wherein each $R^{75}$ is independently selected from H and —$C(O)OR^{11}$), benzotriazol-1-yloxy, tetrazol-5-ylthio, substituted tetrazol-5-ylthio, alkynyl, alkenyl and alkyl, said alkyl or alkenyl group optionally being substituted with halo, —$OR^{10}$ or —$CO_2R^{10}$;

$R^3$ and $R^4$ are the same or different and each independently represents H or any of the substituents of $R^1$ and $R^2$, or $R^3$ and $R^4$ taken together represent a saturated or unsaturated $C_5$-$C_7$ ring fused to the benzene ring;

each of $R^5$, $R^6$, $R^7$ and $R^8$ independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, or $OPO_3R^{10}$, or one of $R^5$, $R^6$, $R^7$ and $R^8$ can be taken in combination with $R^{40}$ as defined below to represent —$(CH_2)_r$— wherein r is 1 to 4 which can be substituted with lower alkyl, lower alkoxy, —$CF_3$ or aryl, or $R^5$ is combined with $R^6$ to represent =O or =S and/or $R^7$ is combined with $R^8$ to represent =O or =S;

$R^{10}$ represents H, alkyl, aryl, or aralkyl;

$R^{11}$ represents alkyl or aryl;

X represents N, CH or C, which C may contain an optional double bond, represented by the dotted line, to carbon atom 11;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, each of A and B independently represents $H_2$, —$(OR^{11})_2$, (H and halo), dihalo, (alkyl and H), (alkyl)$_2$, (H and ——$OC(O)R^{10}$), (H and —$OR^{10}$), =O, (aryl and H), =$NOR^{10}$, or —O—$(CH_2)_p$—O— wherein p is 2, 3 or 4;

R represents $R^{40}$, $R^{42}$, $R^{44}$, or $R^{54}$, as defined below;

$R^{40}$ represents H, aryl, alkyl, cycloalkyl, alkenyl, alkynyl or —D wherein —D represents

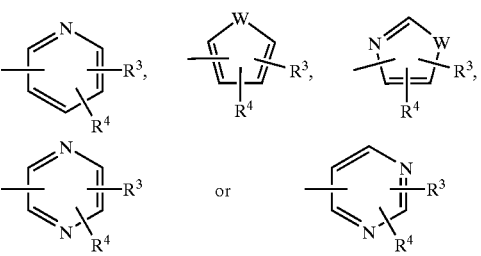

wherein $R^3$ and $R^4$ are as previously defined and W is O, S or $NR^{10}$ wherein $R^{10}$ is as defined above; said $R^{40}$ cycloalkyl, alkenyl and alkynyl groups being optionally substituted with from 1–3 groups selected from halo, —$CON(R^{10})_2$, aryl, —$CO_2R^{10}$, —$OR^{12}$, —$SR^{12}$, —$N(R^{10})_2$, —$N(R^{10})CO_2R^{11}$, —$COR^{12}$, —$NO_2$ or D, wherein —D, $R^{10}$ and $R^{11}$ are as defined above and $R^{12}$ represents $R^{10}$, —$(CH_2)_mOR^{10}$ or —$(CH_2)_qCO_2R^{10}$ wherein $R^{10}$ is as previously defined, m is 1 to 4 and q is 0 to 4; said alkenyl and alkynyl $R^{40}$ groups not containing —OH, —SH or —$N(R^{10})_2$ on a carbon containing a double or triple bond respectively; or $R^{40}$ represents phenyl substituted with a group selected from —$SO_2NH_2$, —$NHSO_2CH_3$, —$SO_2NHCH_3$, —$SO_2CH_3$, —$SOCH_3$, —$SCH_3$, and —$NHSO_2CF_3$, which group is preferably located in the para position of the phenyl ring; or $R^{40}$ represents a group selected from

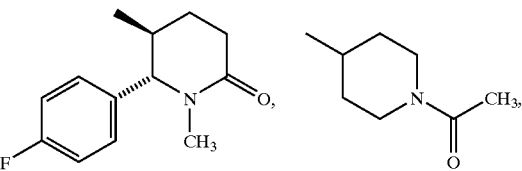

-continued

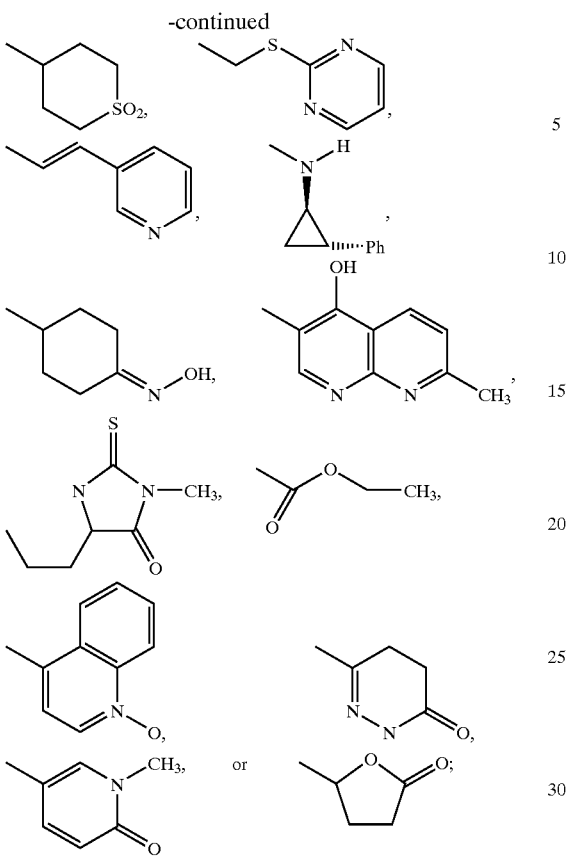

$R^{42}$ represents

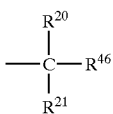

wherein $R^{20}$, $R^{21}$ and $R^{46}$ are each independently selected from the group consisting of:
(1) H;
(2) —(CH$_2$)$_q$SC(O)CH$_3$ wherein q is 1 to 3;
(3) —(CH$_2$)$_q$OSO$_2$CH$_3$ wherein q is 1 to 3;
(4) —OH;
(5) —CS—(CH$_2$)$_w$-(substituted phenyl) wherein w is 1 to 3 and the substitutents on said substituted phenyl group are the same substitutents as described under (12) below for substituted phenyl;
(6) —NH$_2$;
(7) —NHCBZ;
(8) —NHC(O)OR$^{22}$ wherein R$^{22}$ is an alkyl group having from 1 to 5 carbon atoms, or R$^{22}$ represents phenyl substituted with 1 to 3 alkyl groups;
(9) alkyl;
(10) —(CH$_2$)$_k$-phenyl wherein k is 1 to 6;
(11) phenyl;
(12) substituted phenyl wherein the substituents are selected from the group consisting of: halo, NO$_2$, —OH, —OCH$_3$, —NH$_2$, —NHR$^{22}$, —N(R$^{22}$)$_2$, alkyl, —O(CH$_2$)$_t$-phenyl (wherein t is from 1 to 3), and —O(CH$_2$)$_t$-substituted phenyl (wherein t is from 1 to 3);
(13) naphthyl;
(14) substituted naphthyl, wherein the substituents are as defined for substituted phenyl under (12) above;
(15) bridged polycyclic hydrocarbons having from 5 to 10 carbon atoms;
(16) cycloalkyl having from 5 to 7 carbon atoms;
(17) heteroaryl;
(18) hydroxyalkyl;
(19) substituted pyridyl or substituted pyridyl N-oxide wherein the substituents are selected from methylpyridyl, morpholinyl, imidazolyl, 1-piperidinyl, 1-(4-methylpiperazinyl), —S(O)$_x$R$^{11}$, and any of the substituents given under (12) above for substituted phenyl, and said substitutents are bound to a ring carbon by replacement of the hydrogen bound to said carbon;

(20)

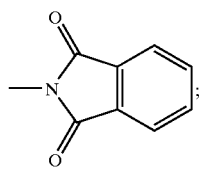

(21)

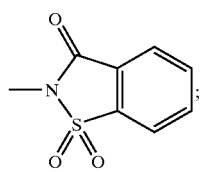

(22)

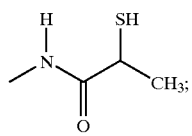

(23) —NHC(O)—(CH$_2$)$_k$-phenyl or —NH(O)—(CH$_2$)$_k$-(substituted phenyl), wherein said k is as defined under (10) above;
(24) piperidine Ring V:

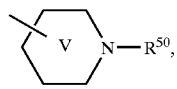

wherein R$^{50}$ represents H, alkyl, alkylcarbonyl, alkoxycarbonyl, haloalkyl, or —C(O)NH(R$^{10}$) wherein R$^{10}$ is H or alkyl;
(25) —NHC(O)CH$_2$C$_6$H$_5$ or —NHC(O)CH$_2$-(substituted C$_6$H$_5$);
(26) —NHC(O)OC$_6$H$_5$;
(27) (28) (29)

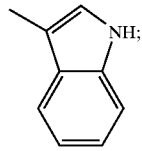

(30) —OC(O)-heteroaryl (for example pyridine-4-carbonyloxy);
(31) —O-alkyl (e.g., —OCH$_3$);
(32) —CF$_3$;
(33) —CN;
(34) a heterocycloalkyl group of the formula and

(35) a piperidinyl group of the formula wherein R$^{85}$ is H, alkyl, or alkyl substituted by —OH or —SCH$_3$; or R$^{20}$ and R$^{21}$ taken together form an =O group and the remaining R$^{46}$ is as defined above; or two of R$^{20}$, R$^{21}$ and R$^{46}$ taken together form piperidine Ring V wherein R$^{50}$ is as defined under (24) above;

with the proviso that R$^{46}$, R$^{20}$ and R$^{21}$ are selected such that the carbon atom to which they are bound is not bonded to more than one heteroatom;

R$^{44}$ represents —NR$^{25}$R$^{48}$ wherein R$^{25}$ represents heteroaryl, N-methyl-piperidinyl or aryl, and R$^{48}$ represents H or alkyl;

R$^{54}$ represents an N-oxide heterocyclic group of the formula (i), (ii), (iii) or (iv):

wherein R$^{56}$, R$^{58}$, and R$^{60}$ are the same or different and each is independently selected from H, halo, —CF$_3$, —OR$^{10}$, —C(O)R$^{10}$, —SR$^{10}$, —S(O)$_e$R$^{11}$ (wherein e is 1 or 2), —N(R$^{10}$)$_2$, —NO$_2$, —CO$_2$R$^{10}$, —OCO$_2$R$^{11}$, —OCOR$^{10}$, alkyl, aryl, alkenyl and alkynyl, which alkyl may be substituted with —OR$^{10}$, —SR$^{10}$ or —N(R$^{10}$)$_2$ and which alkenyl may be substituted with OR$^{11}$ or SR$^{11}$; or R$^{54}$ represents an N-oxide heterocyclic group of the formula (ia), (iia), (iiia) or (iva):

wherein Y represents N$^+$—O$^-$ and E represents N; or

R$^{54}$ represents an alkyl group substituted with one of said N-oxide heterocyclic groups (i), (ii), (iii), (iv), (ia), (iia), (iiia) or (iva); and Z represents O or S such that R can be taken in combination with R$^5$, R$^6$, R$^7$ or R$^8$ as defined above, or R represents R$^{40}$, R$^{42}$, R$^{44}$ or R$^{54}$.

WO 95/10516 and WO 96/30363 also disclose compounds of the formulas:

(5.0)

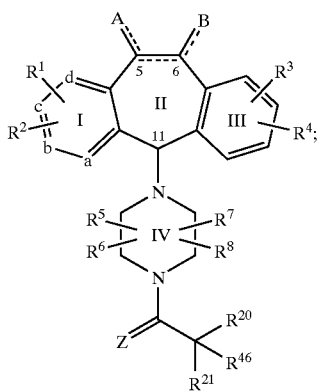

(5.1)

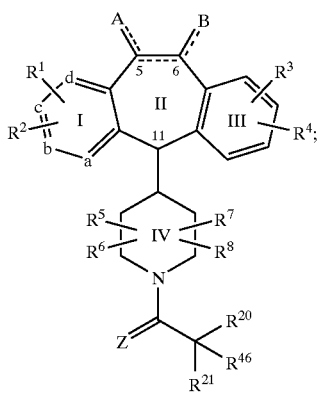

(5.2)

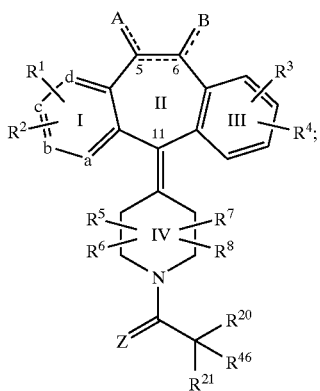

(5.3)

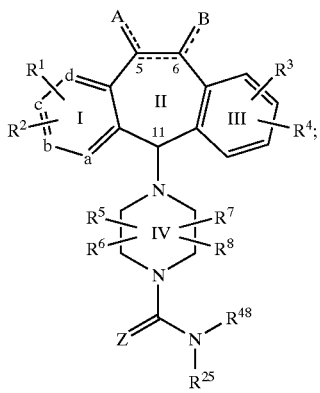

(5.3A)

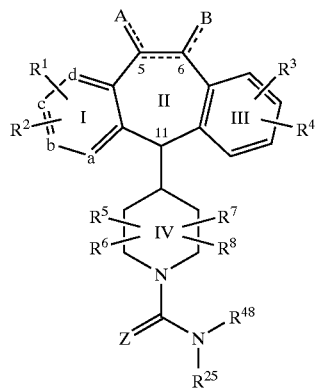

or (5.3B)

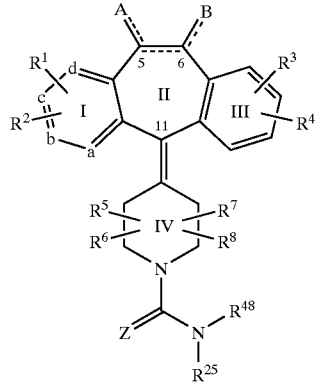

or a pharmaceutically acceptable salt or solvate thereof, wherein all the substituents are as defined for formula 1.0 of WO 95/10516 and WO 96/30363, and wherein for the compounds of Formula 5.2 the substituents $R^{20}$, $R^{21}$, and $R^{46}$ are selected such that when one of said substituents $R^{20}$, $R^{21}$, and $R^{46}$ is selected from the group consisting of: (1) H, (2) —OH, (3) —NH$_2$, (4) —NHC(O)OR$^{22}$, (5) alkyl, (6) phenyl, (7) heteroaryl, (8) hydroxyalkyl, (9) substituted pyridyl, (10) substituted phenyl and (11) —O-alkyl, then the remaining two of said substituents $R^{20}$, $R^{21}$ and $R^{46}$ cannot both be H when: (a) $R^1$ and $R^2$ are both H, and (b) the double bond between C-5 and C-6 is absent, and (c) both A and B are H$_2$, and (d) $R^4$ is H, and (e) $R^3$ is H or Cl at C-8.

WO 96/30363 also disclose the compounds:

(5.200)

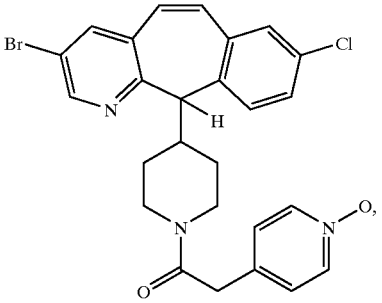

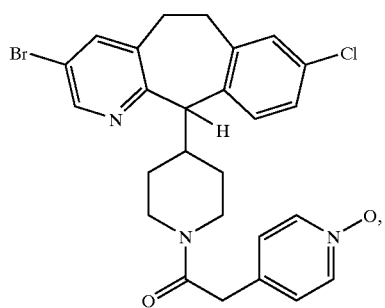
(5.201)
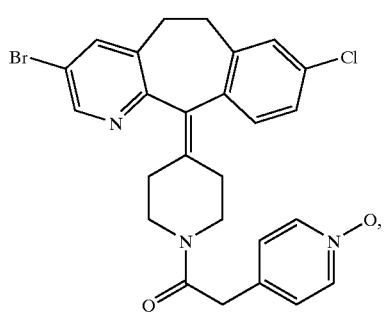
(5.206)
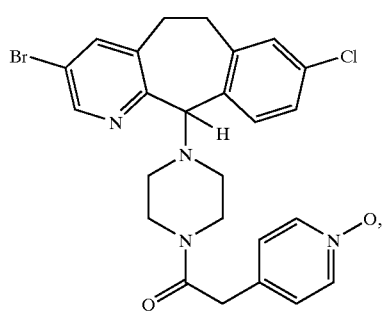
(5.202)
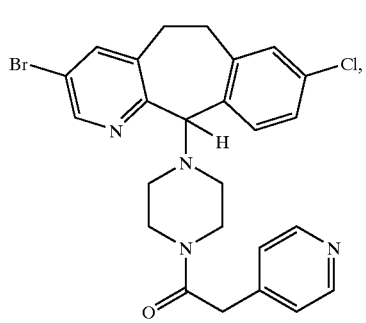
(5.207)
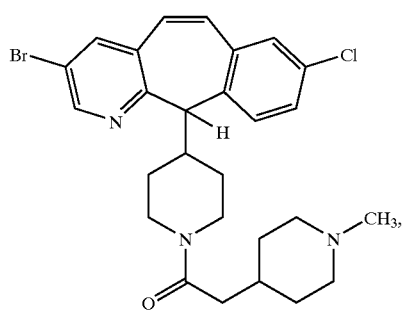
(5.203)
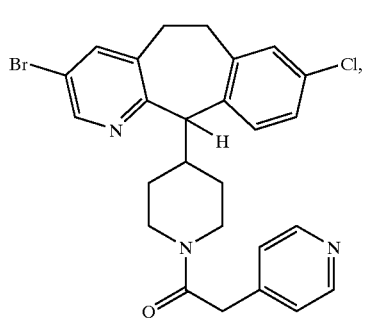
(5.208)
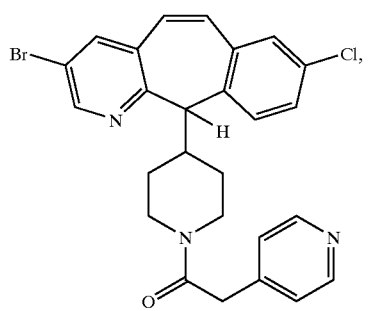
(5.204)
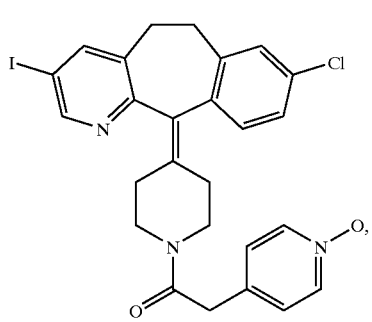
(5.209)
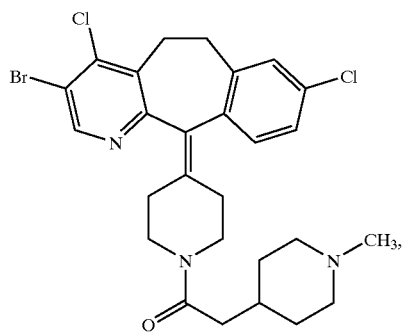
(5.205)
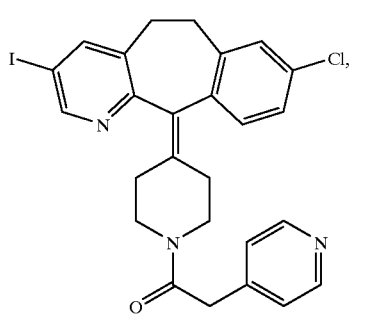
(5.210)

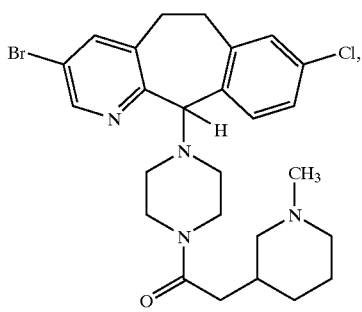
(5.211)
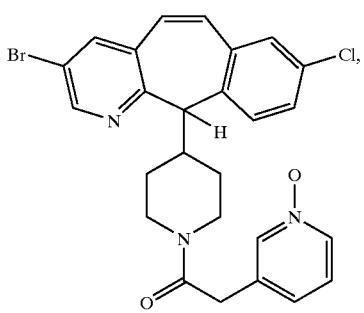
(5.217)
(5.216)
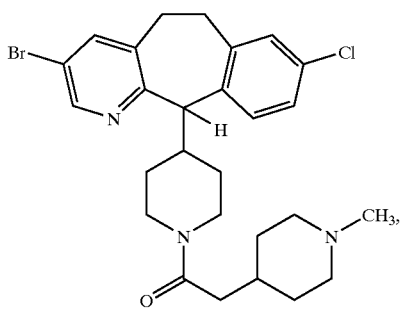
(5.212)
(5.218)
(5.214)
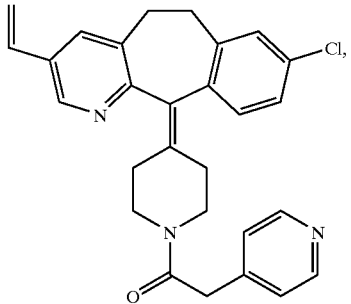
(5.213)
(5.219)
and
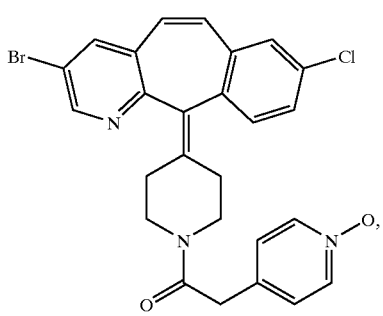
(5.215)
(5.220)
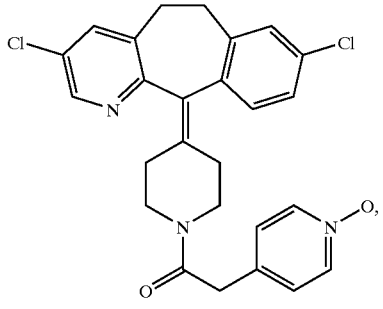
WO 97/23478 published Jul. 3, 1997 (see also U.S. Pat. No. 5,894,442) discloses the compounds:

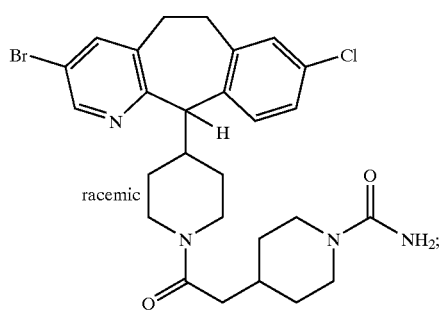 (1.0)
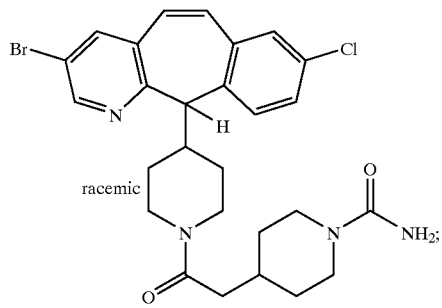 (2.0)
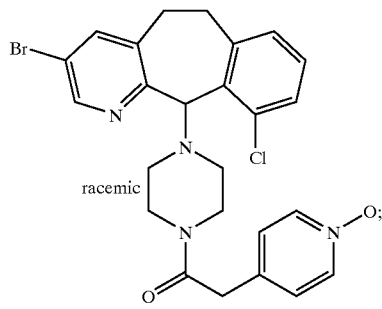 (3.0)
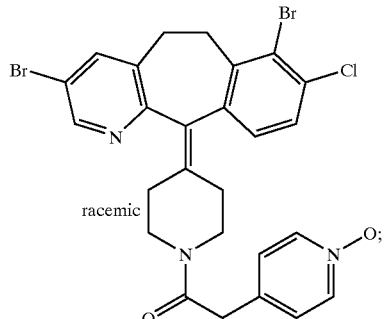 (5.0)
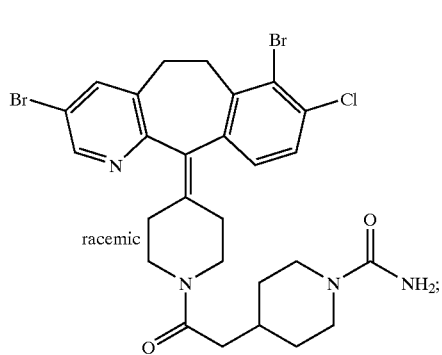 (6.0)
-continued
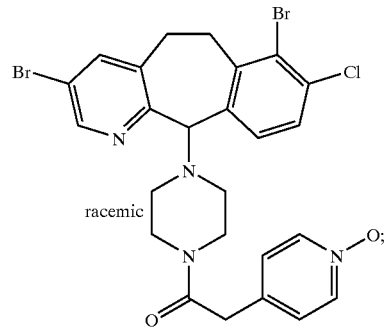 (7.0)
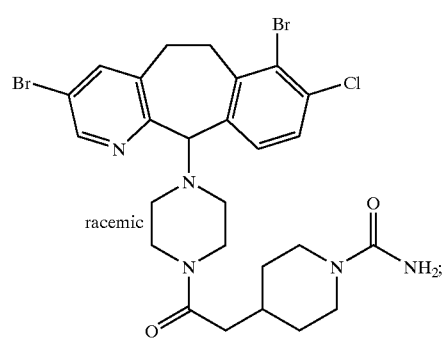 (7.0A)
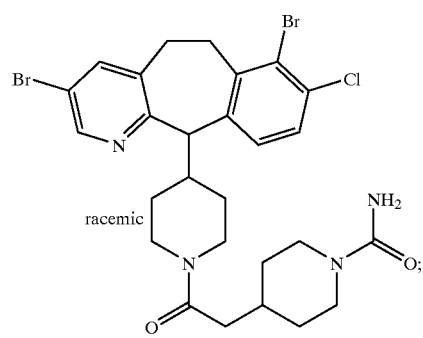 (8.0)
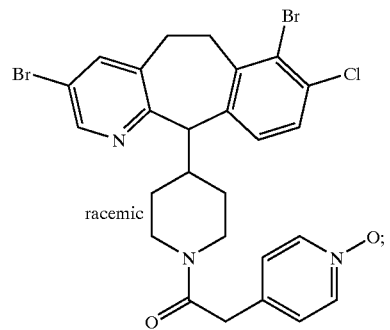 (8.0A)
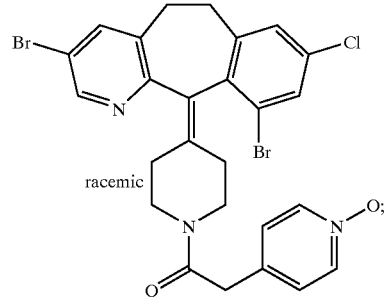 (9.0)

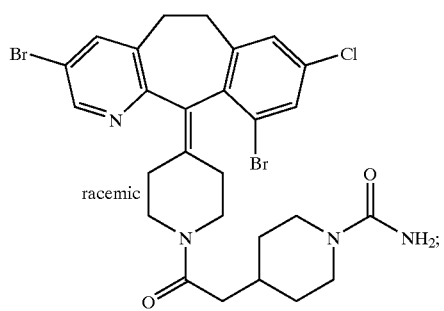
(10.0)
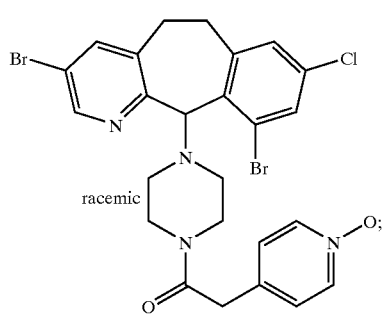
(11.0)
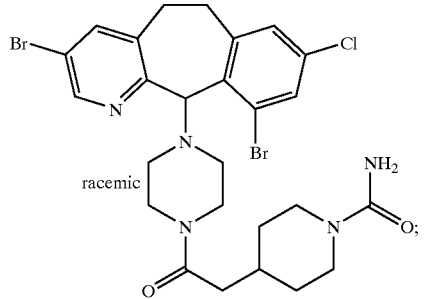
(12.0)
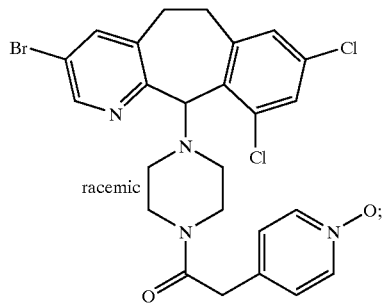
(13.0)
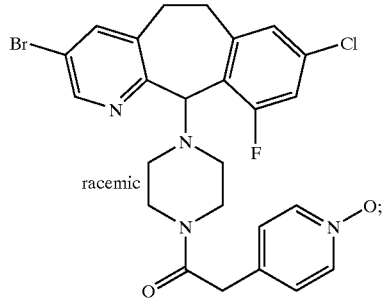
(14.0)
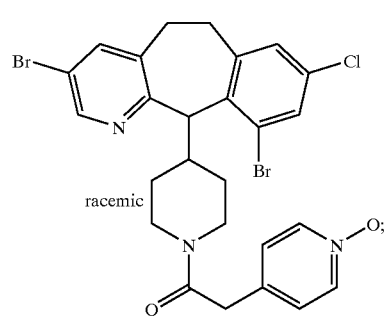
(15.0)
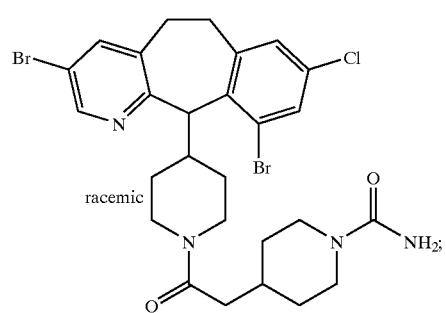
(16.0)
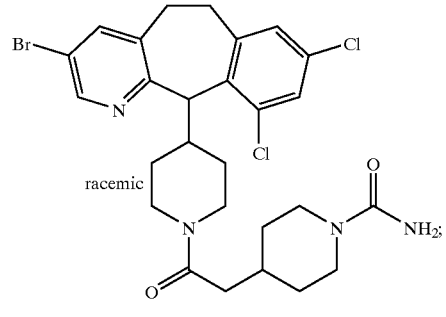
(17.0)
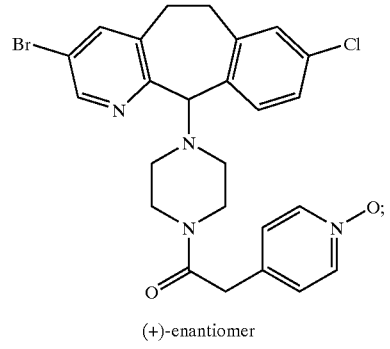
(18.0)
(+)-enantiomer
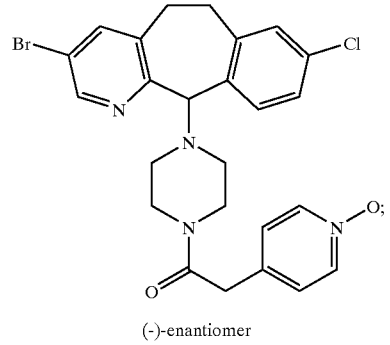
(19.0)
(−)-enantiomer

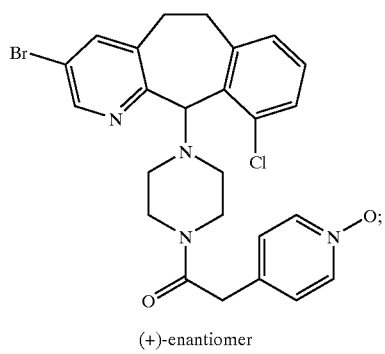
(20.0)
(+)-enantiomer
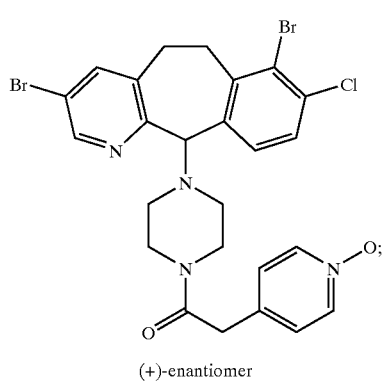
(21.0)
(+)-enantiomer
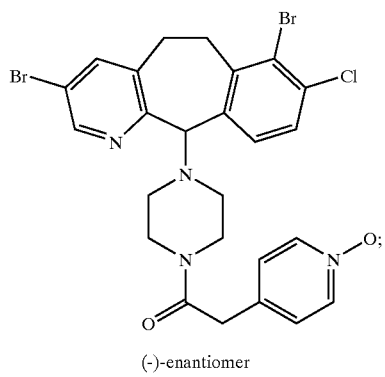
(22.0)
(−)-enantiomer
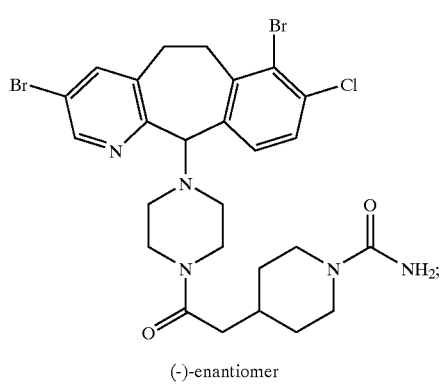
(23.0)
(−)-enantiomer
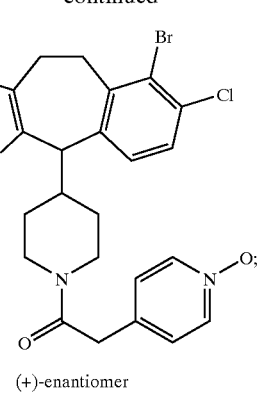
(24.0)
(+)-enantiomer
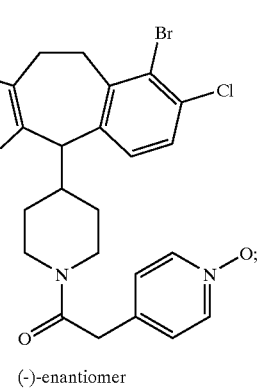
(25.0)
(−)-enantiomer
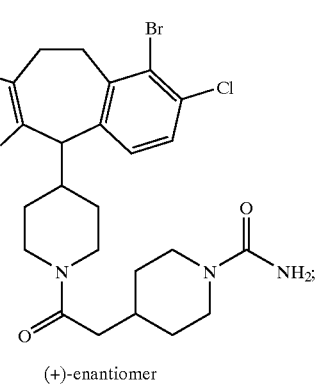
(26.0)
(+)-enantiomer
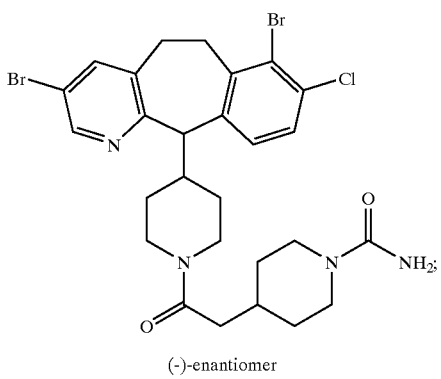
(27.0)
(−)-enantiomer

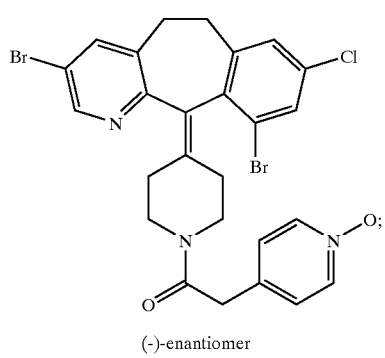
(28.0) (−)-enantiomer
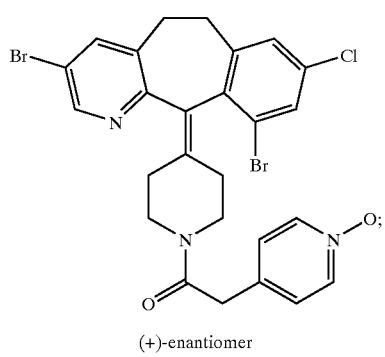
(29.0) (+)-enantiomer
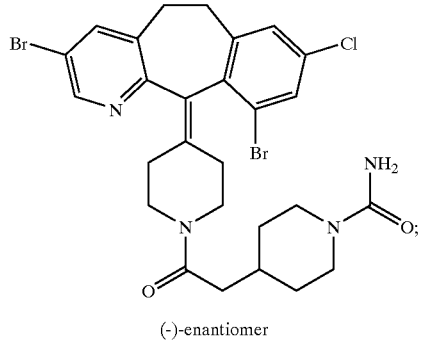
(30.0) (−)-enantiomer
(31.0)
(+)-enantiomer
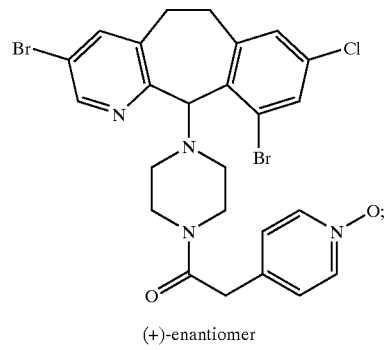
(32.0) (+)-enantiomer
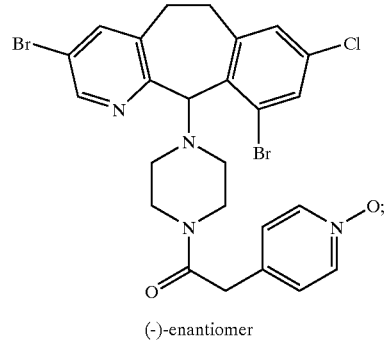
(33.0) (−)-enantiomer
(34.0)
(+)-enantiomer
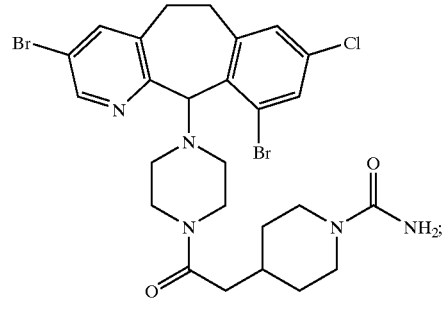
(35.0) (−)-enantiomer (36.0)
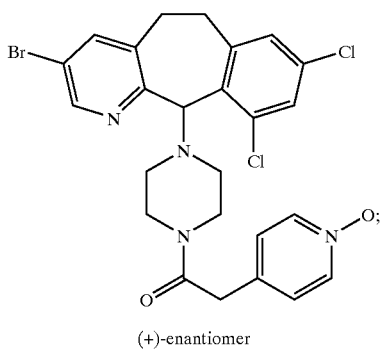
(+)-enantiomer
(37.0)
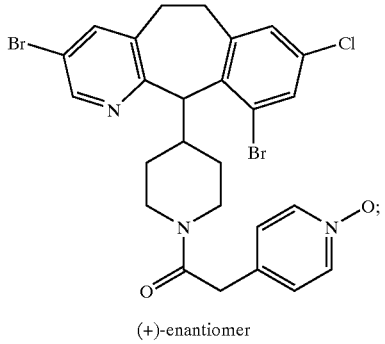
(+)-enantiomer
(38.0)
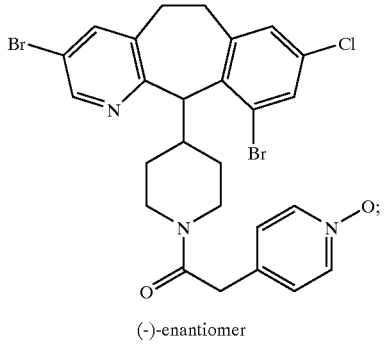
(−)-enantiomer
(39.0)
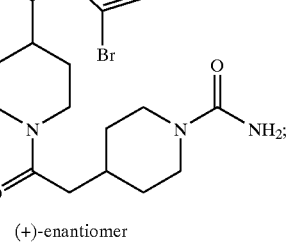
(+)-enantiomer
(40.0)
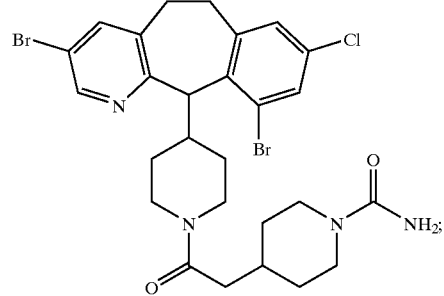
(−)-enantiomer
(41.0)
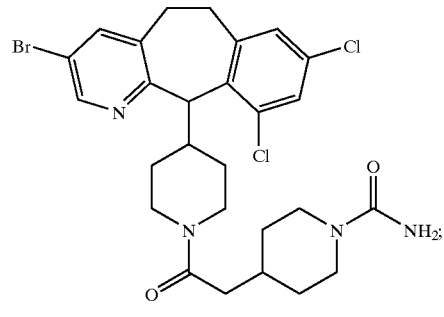
(+)-enantiomer
(42.0)
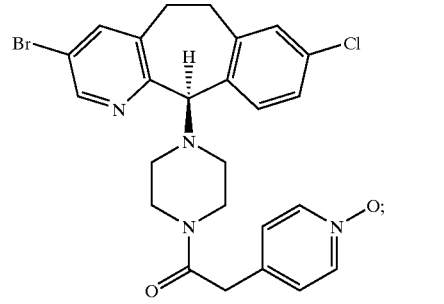
(43.0)
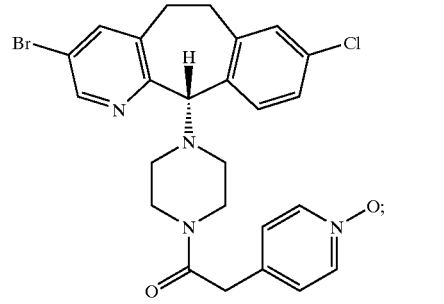
(44.0)
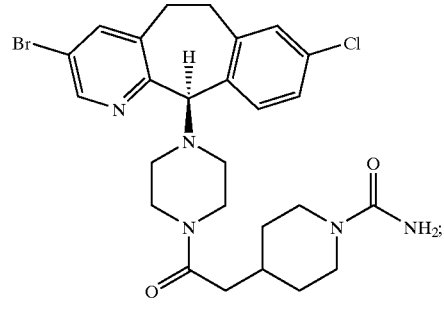

-continued
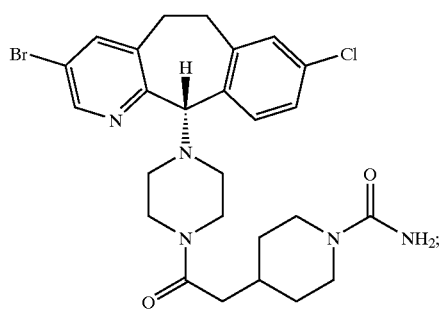 (45.0)
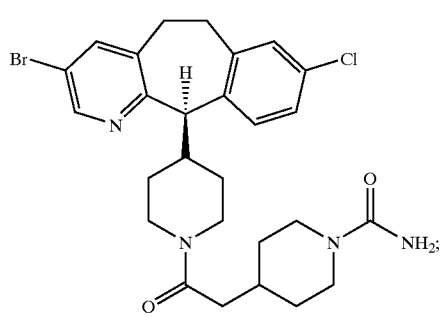 (46.0)
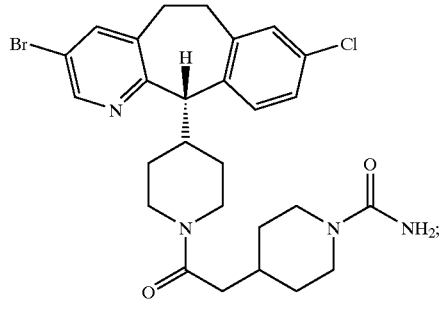 (47.0)
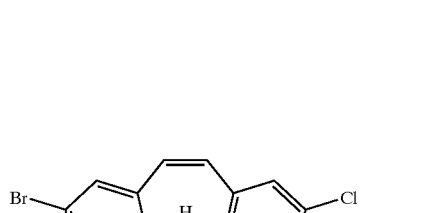 (48.0)
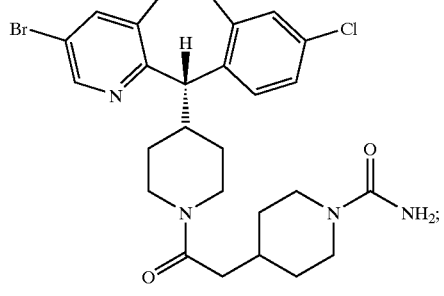
-continued
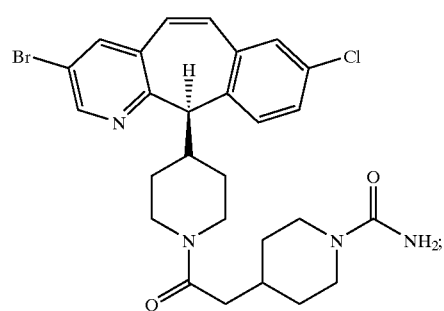 (49.0)
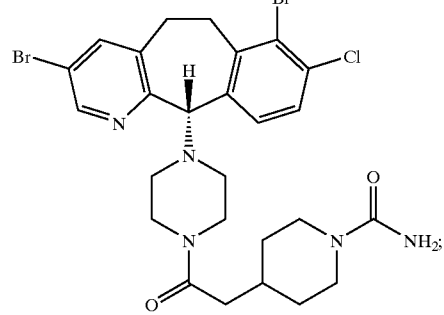 (50.0)
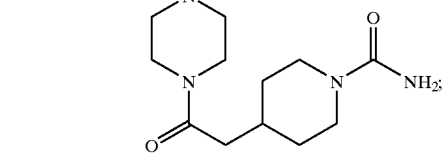 (51.0)
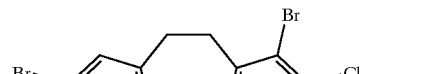 (52.0)
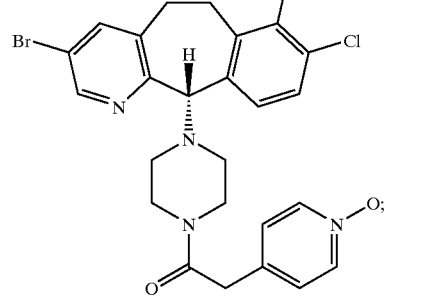 (53.0)

31
-continued
(54.0)
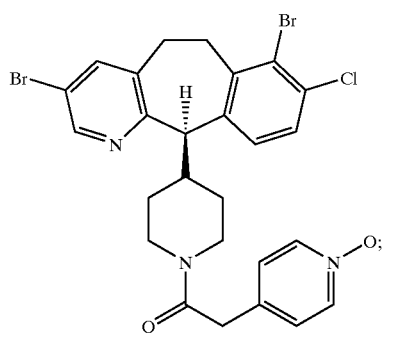
(55.0)
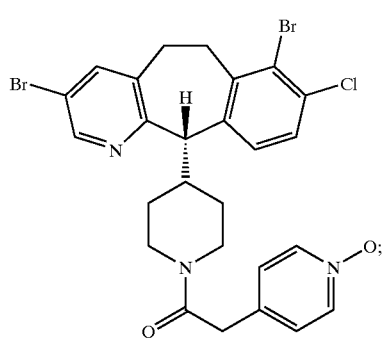
(56.0)
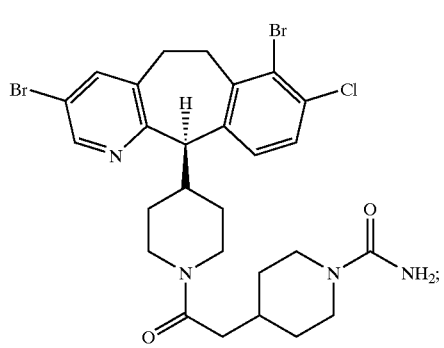
(57.0)
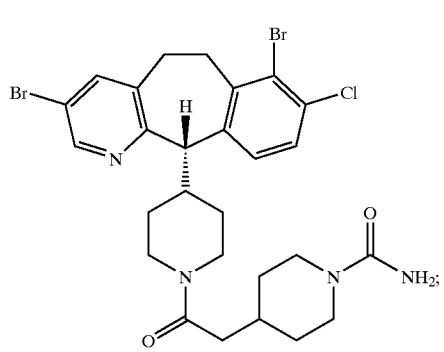
(58.0)
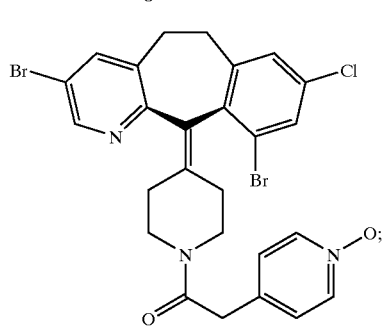
32
-continued
(59.0)
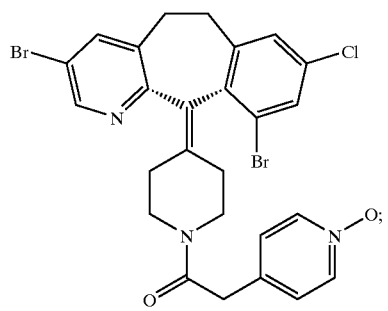
(60.0)
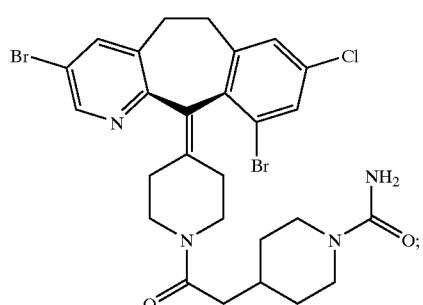
(61.0)
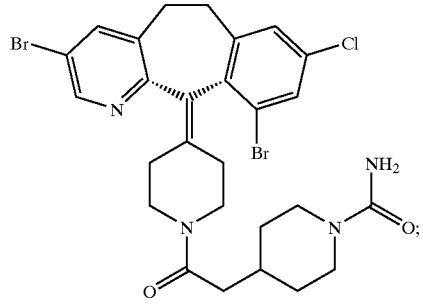
(62.0)
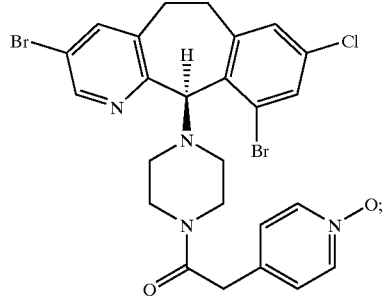
(63.0)
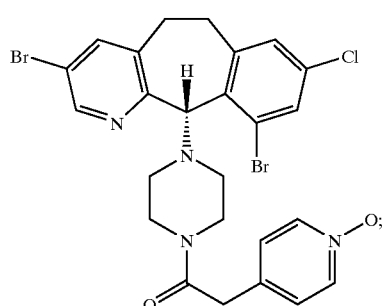

(64.0) 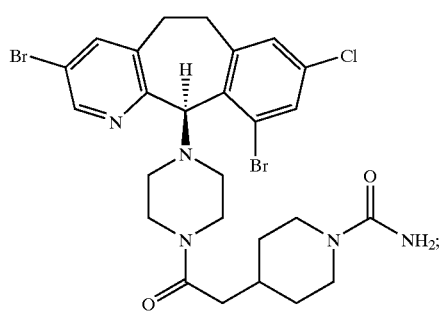
(65.0) 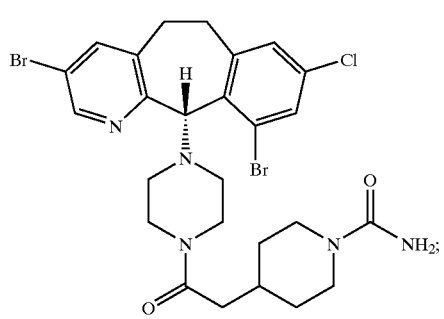
(66.0) 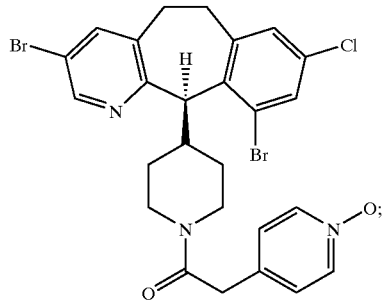
(67.0) 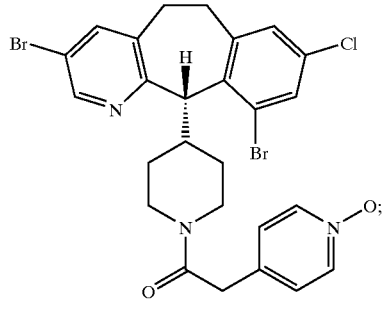
(68.0) 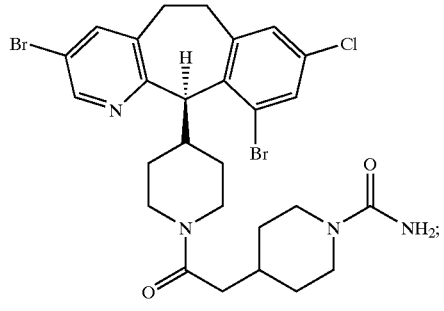
(69.0) 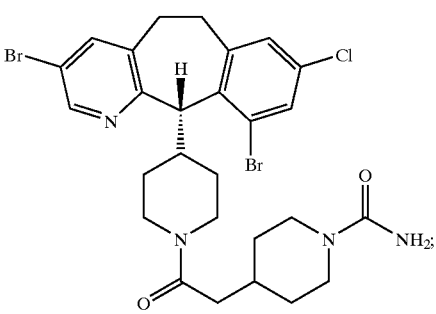
(70.0) 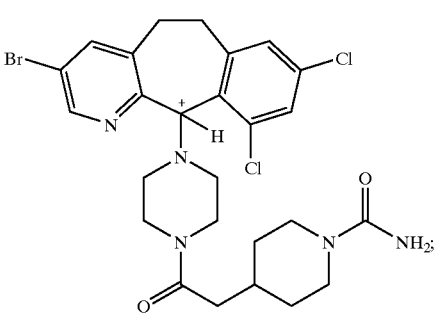
(71.0) 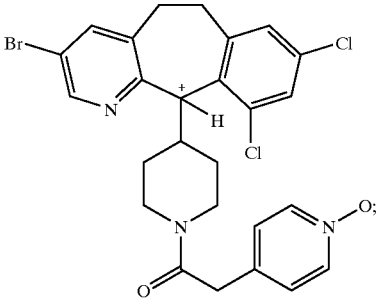
(72.0) 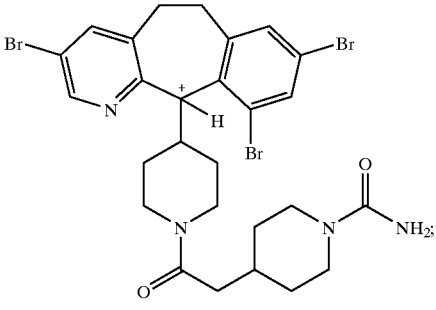
(73.0) 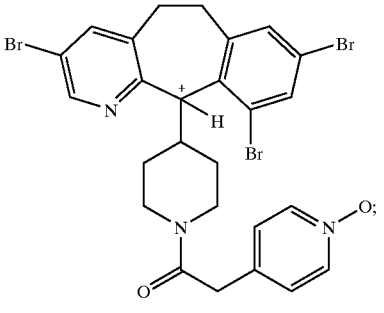

-continued (74.0)
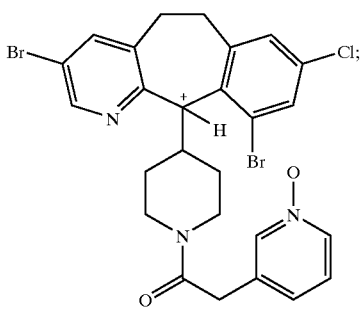

(75.0)
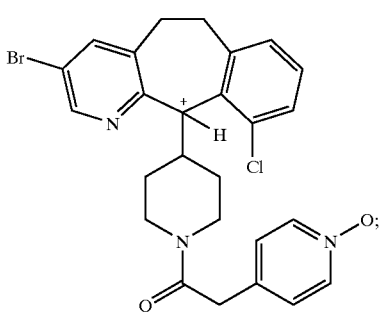

(76.0)
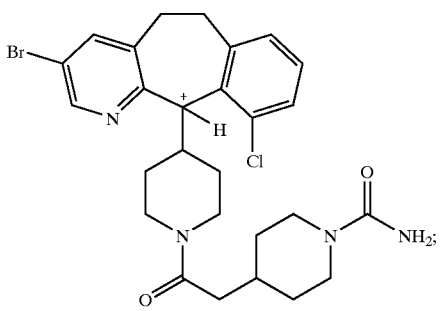

(77.0)
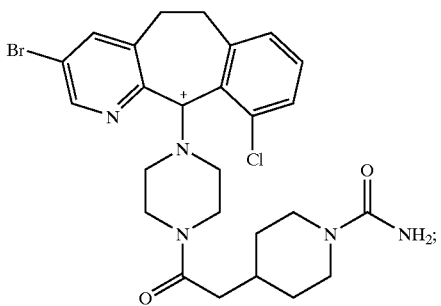

(78.0)
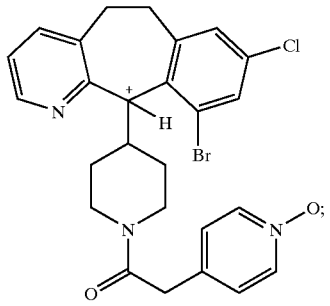

(79.0)
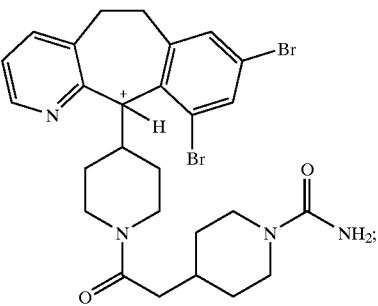

(80.0)
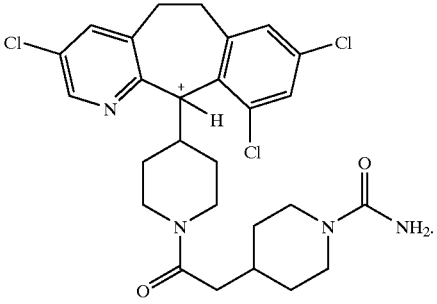

or pharmaceutically acceptable salts thereof.

A preferred compound for use as a P-gp inhibitor in the method of the present invention has the formula:

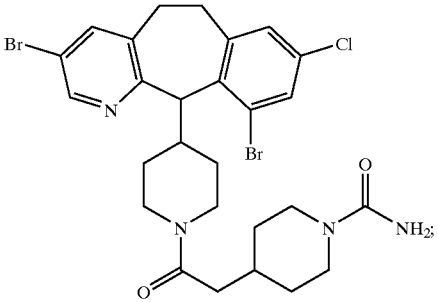

i.e., the compound 4-[2-[4-[(8-chloro-3,10-dibromo-6,11-dihydro-5H-benzo[5,6]cyclohepta[1,2-b]pyridin-11-yl)-1-piperidinyl]-2-oxoethyl]-1-piperidine-carboxamide, preferably the (+)-isomer thereof, which has the structure

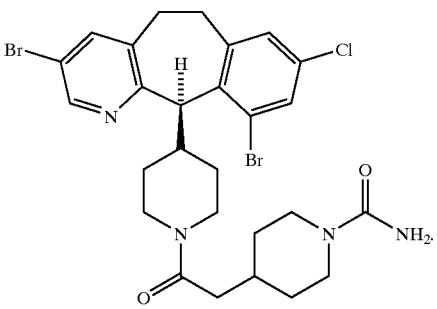

See U.S. Pat. No. 5,874,442, the disclosure of which is expressly incorporated herein by reference. See also U.S. Pat. No. 5,719,148, which issued on Feb. 17, 1998, and is expressly incorporated herein by reference.

U.S. application Ser. No. 08/877057 filed Jun. 17, 1997, now abandoned, discloses compounds of the formula:
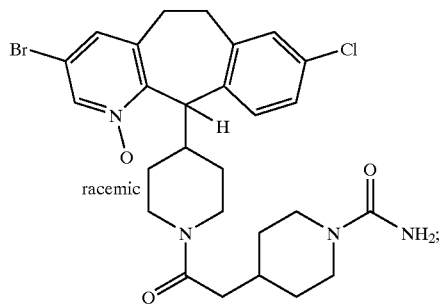
(1.0)
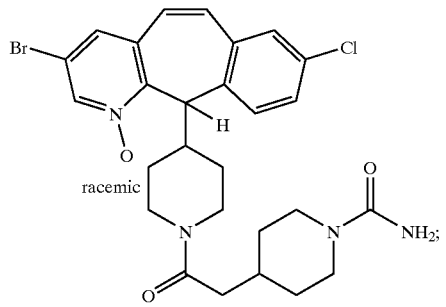
(2.0)
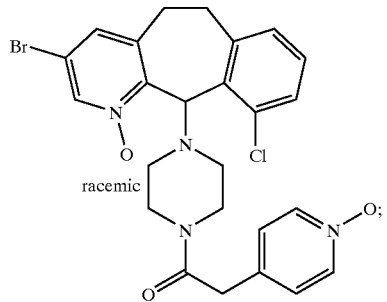
(3.0)
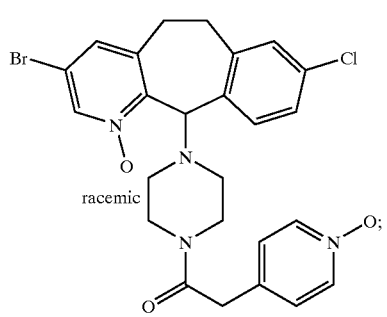
(3.0A)
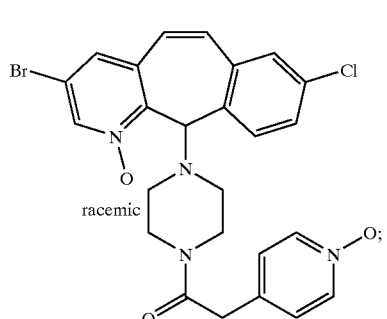
(3.0B)
-continued
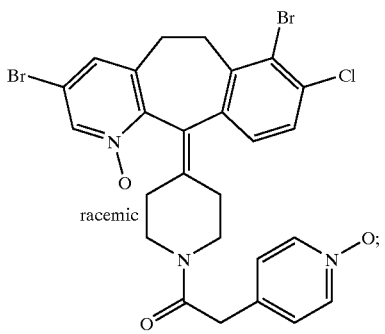
(5.0)
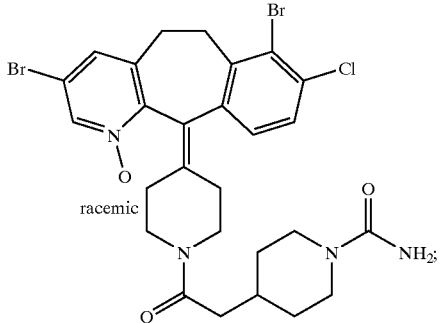
(6.0)
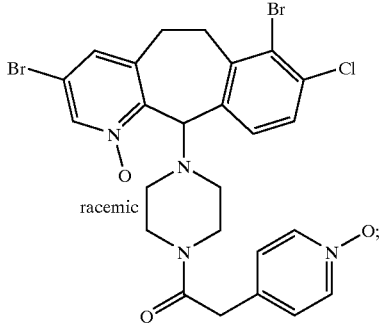
(7.0)
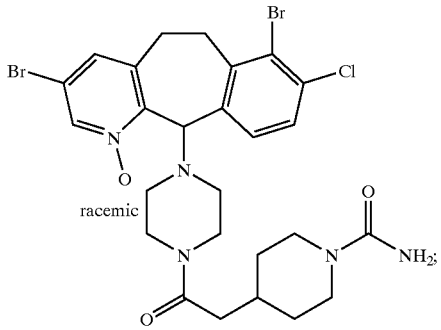
(7.0A)

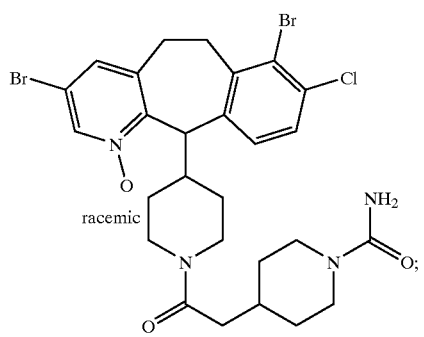
(8.0)
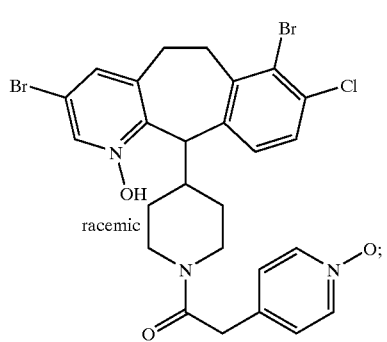
(8.0A)
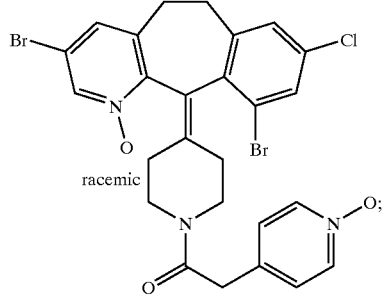
(9.0)
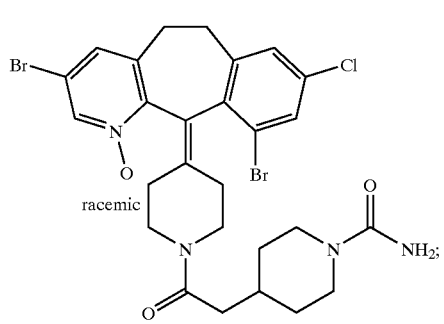
(10.0)
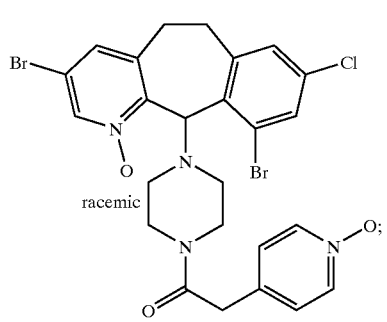
(11.0)
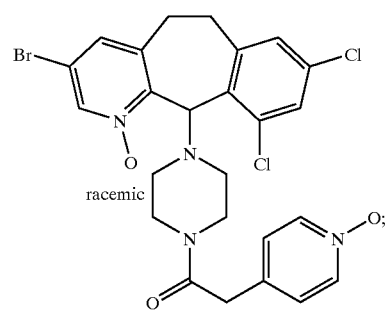
(12.0)
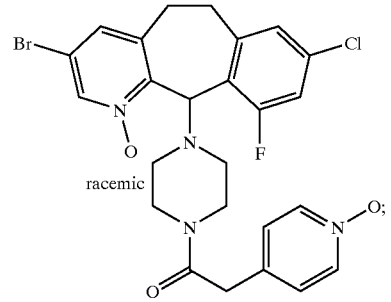
(13.0)
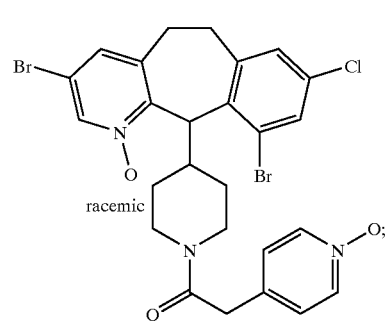
(14.0)
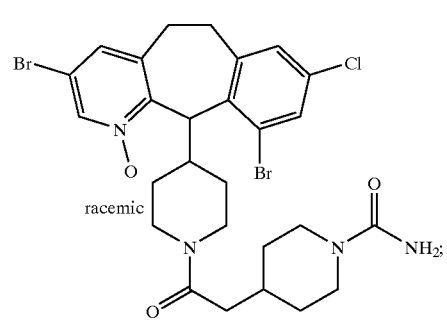
(15.0)
(16.0)

(17.0)
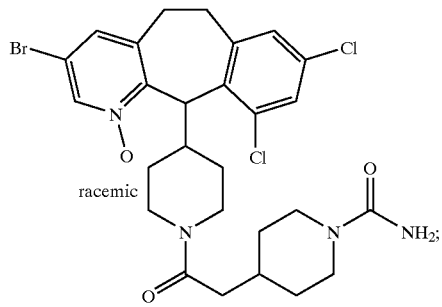
racemic
(18.0)
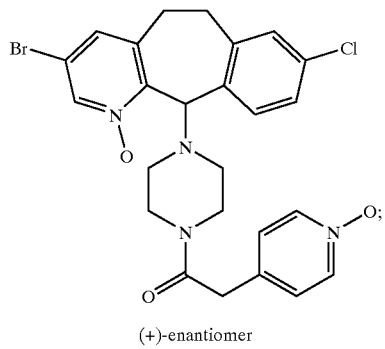
(+)-enantiomer
(19.0)
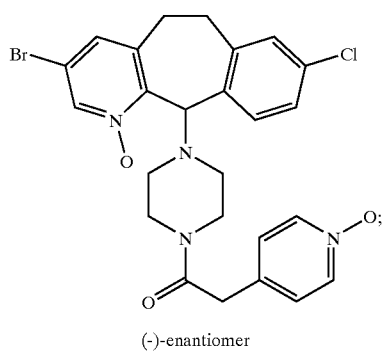
(−)-enantiomer
(20.0)
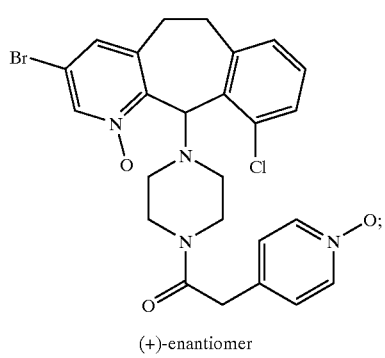
(+)-enantiomer
(21.0)
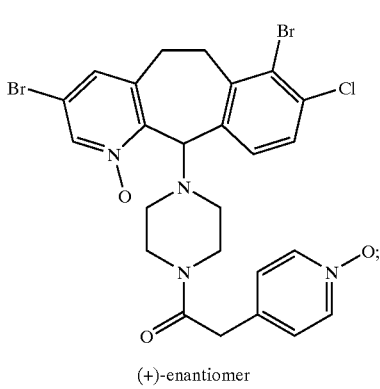
(+)-enantiomer
(22.0)
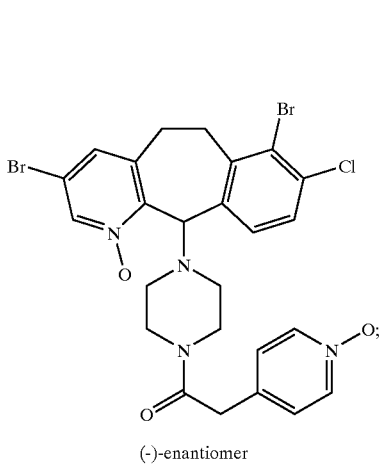
(−)-enantiomer
(23.0)
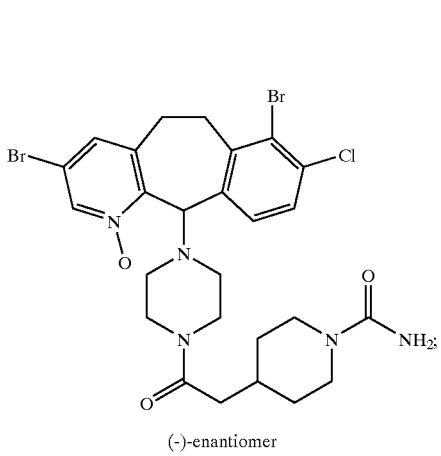
(−)-enantiomer
(24.0)
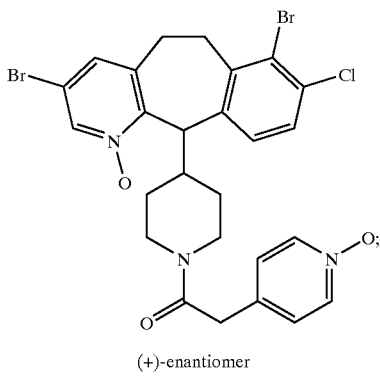
(+)-enantiomer (25.0)
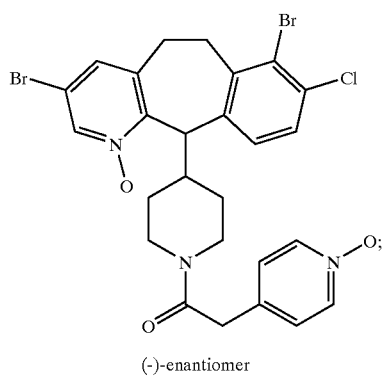
(-)-enantiomer
(26.0)
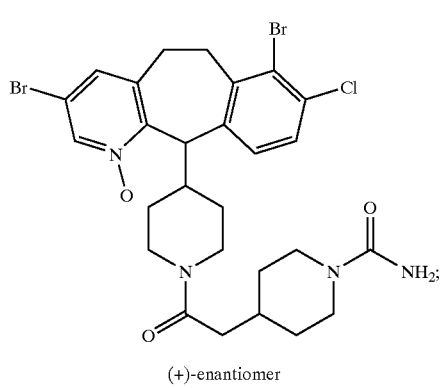
(+)-enantiomer
(27.0)
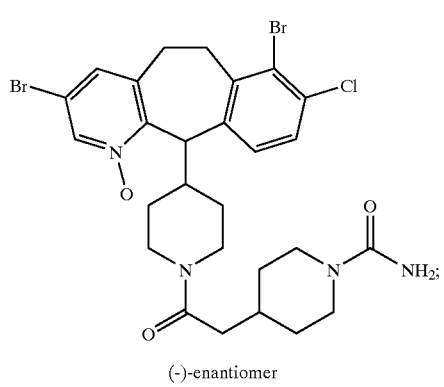
(-)-enantiomer
(28.0)
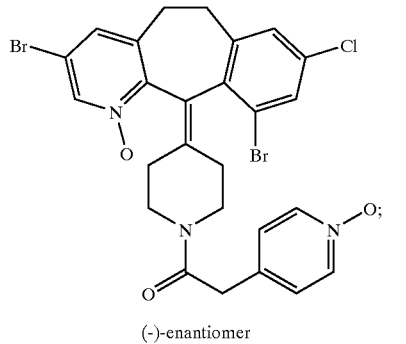
(-)-enantiomer
(29.0)
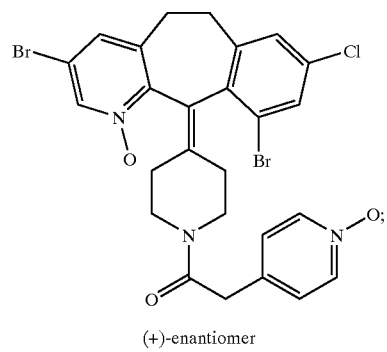
(+)-enantiomer
(30.0)
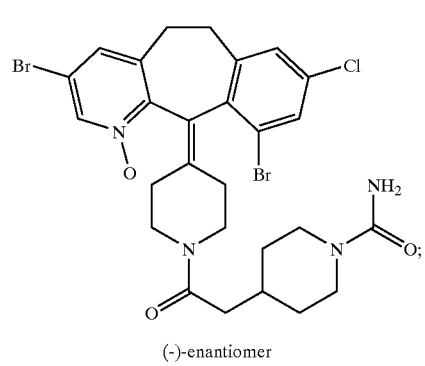
(-)-enantiomer
(31.0)
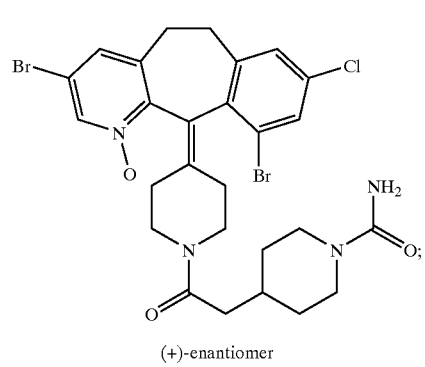
(+)-enantiomer
(32.0)
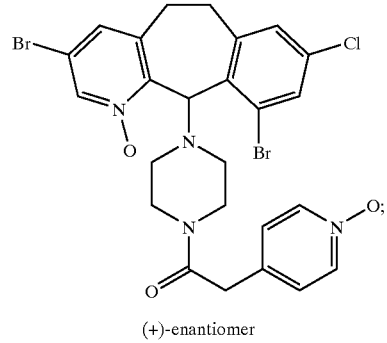
(+)-enantiomer

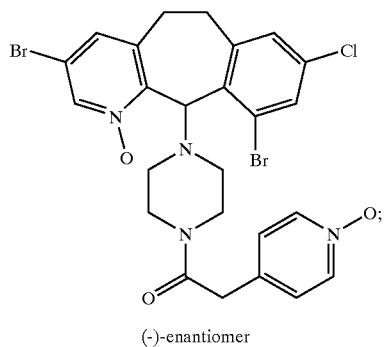
(33.0)
(-)-enantiomer
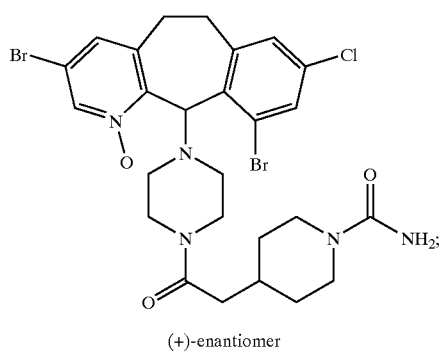
(34.0)
(+)-enantiomer
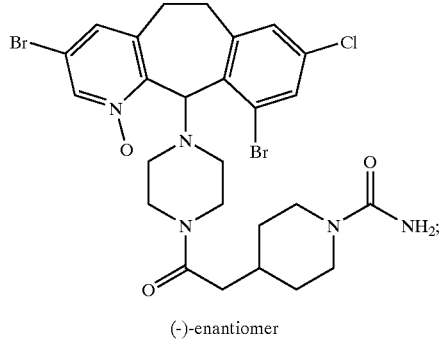
(35.0)
(-)-enantiomer
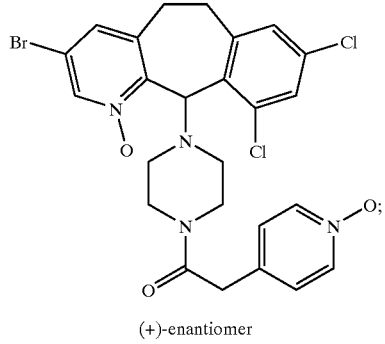
(36.0)
(+)-enantiomer
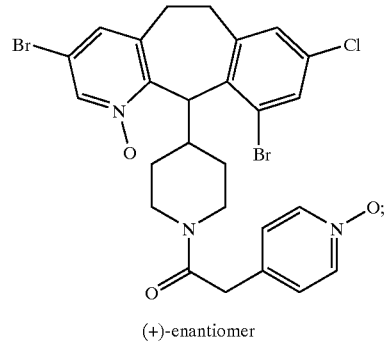
(37.0)
(+)-enantiomer
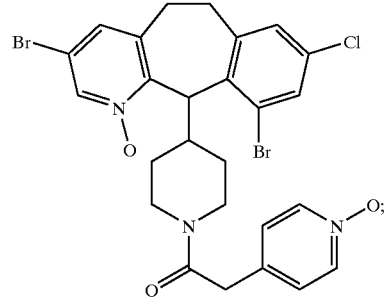
(38.0)
(-)-enantiomer
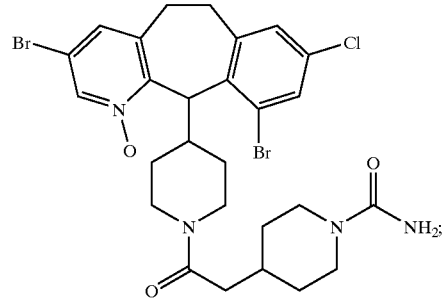
(39.0)
(+)-enantiomer
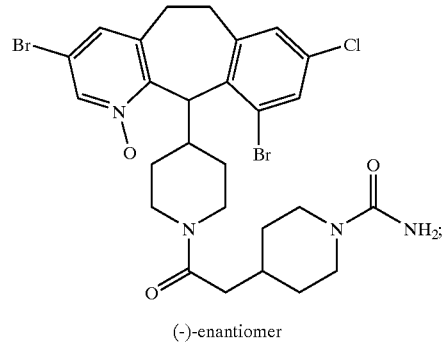
(40.0)
(-)-enantiomer

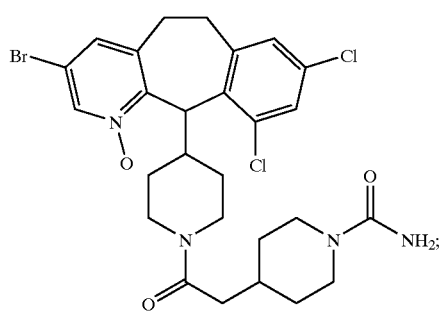
(41.0)
(+)-enantiomer
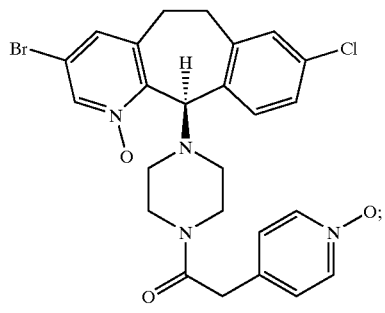
(42.0)
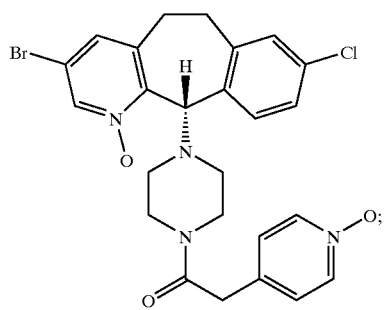
(43.0)
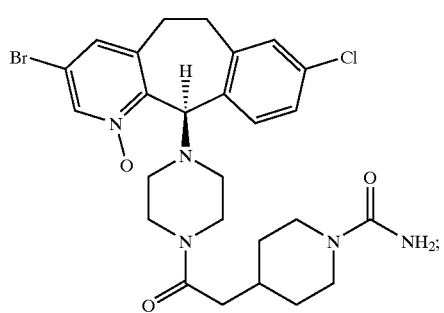
(44.0)
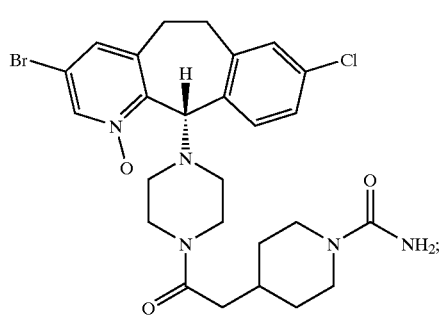
(45.0)
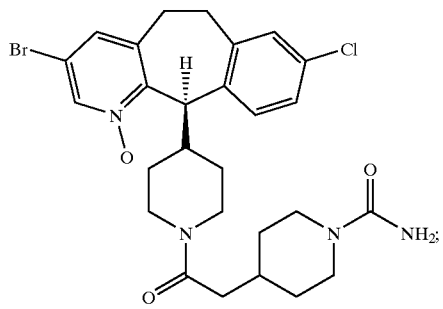
(46.0)
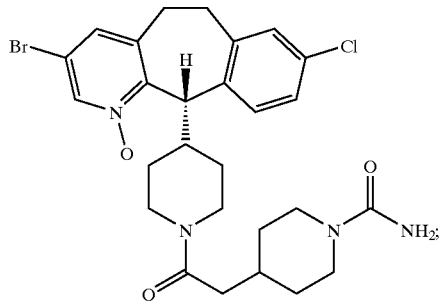
(47.0)
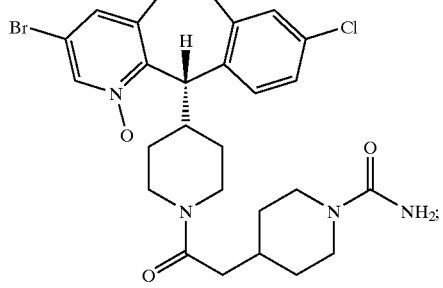
(48.0)
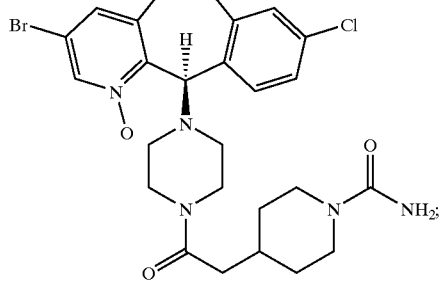
(49.0)
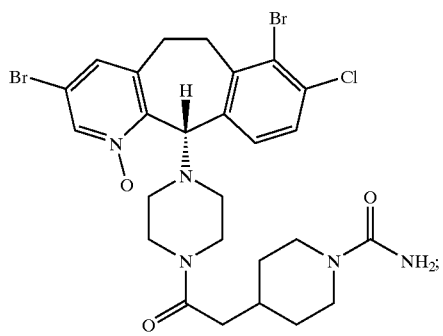
(50.0)

(51.0) 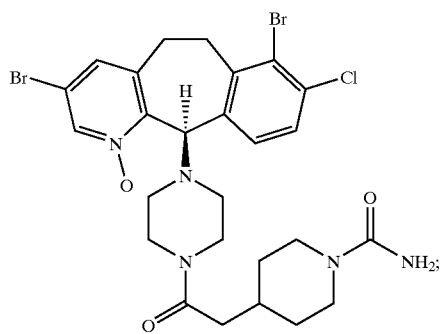
(52.0) 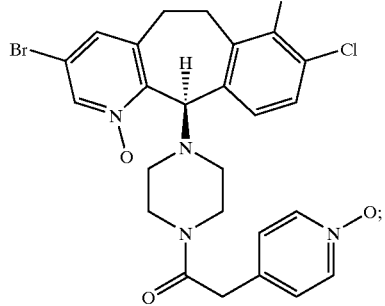
(53.0) 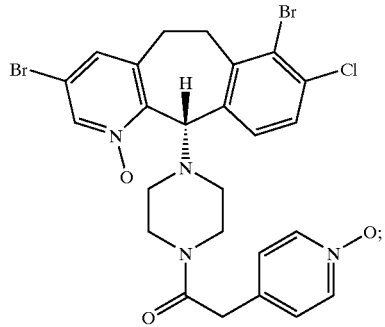
(54.0) 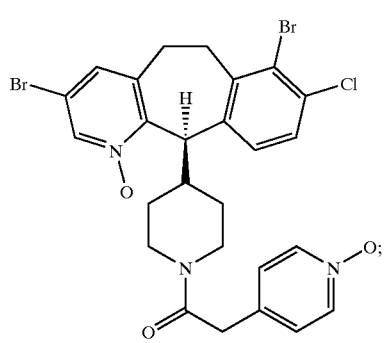
(55.0) 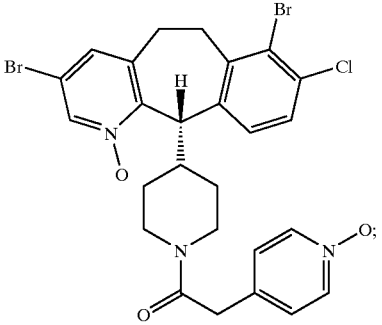
(56.0) 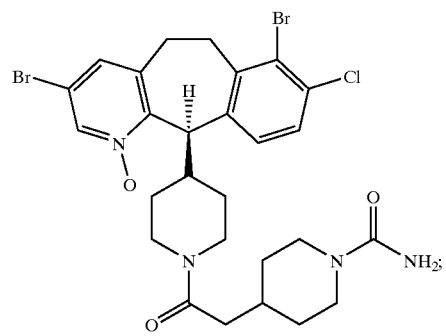
(57.0) 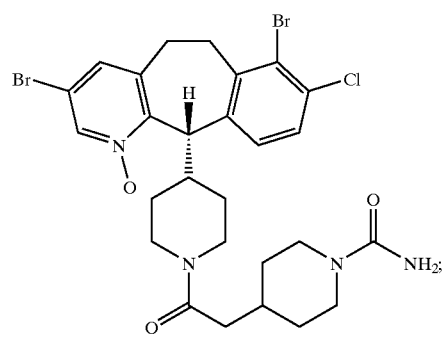
(58.0) 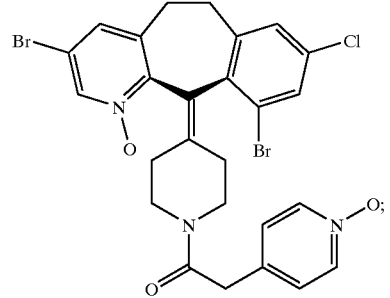
(59.0) 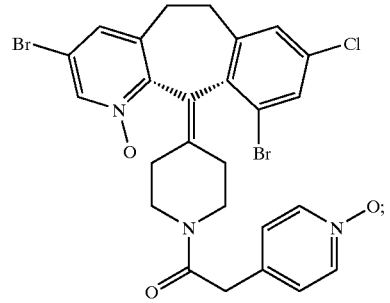

(60.0)
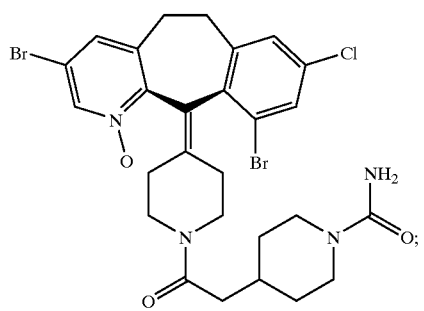
(61.0)
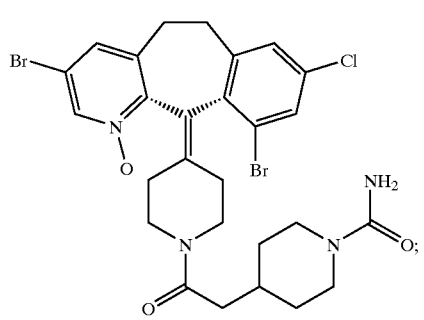
(62.0)
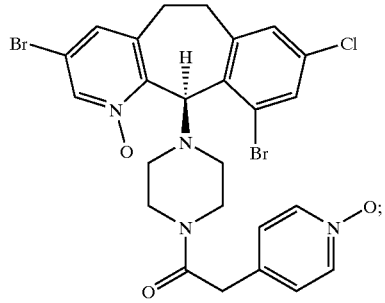
(63.0)
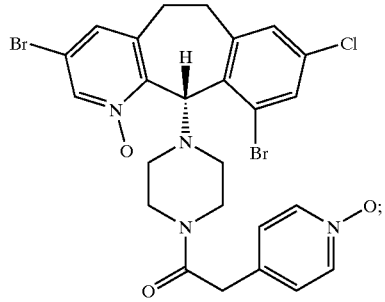
(64.0)
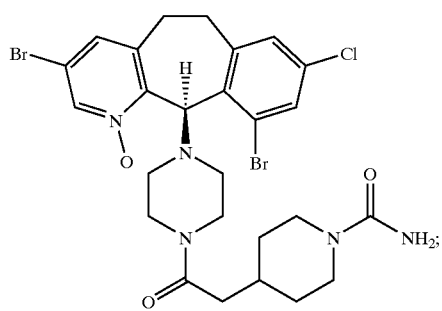
(65.0)
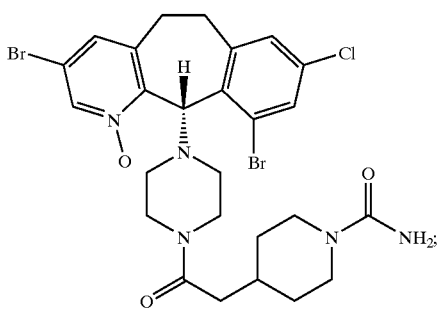
(66.0)
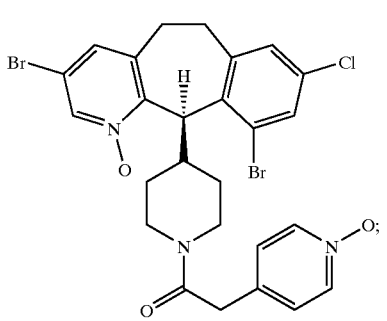
(67.0)
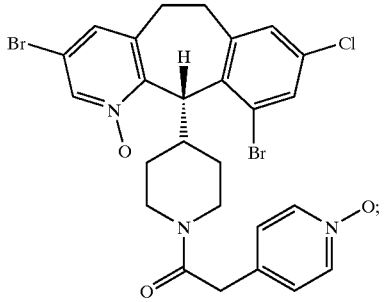
(68.0)
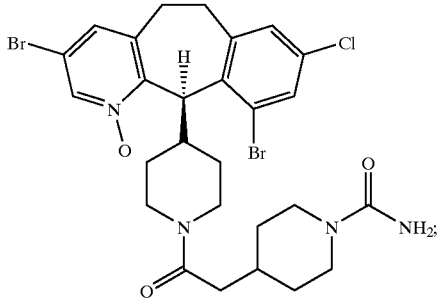
(69.0)
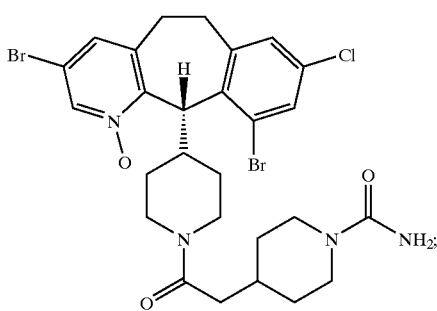

(70.0) 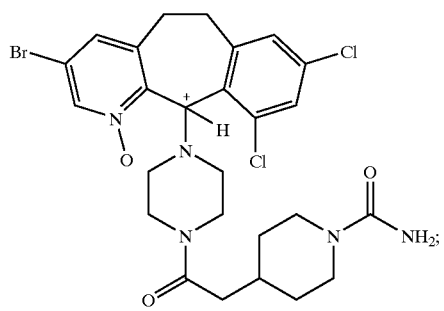
(71.0) 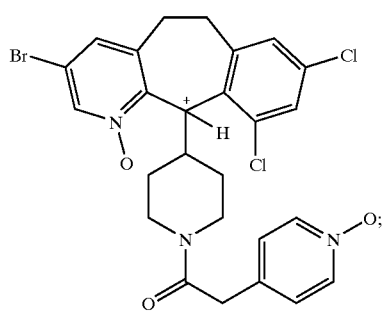
(72.0) 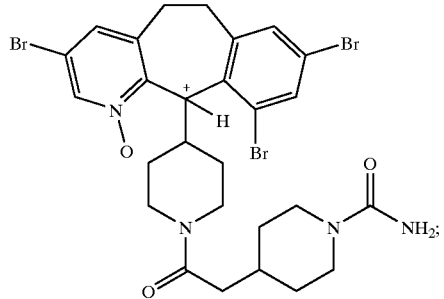
(73.0) 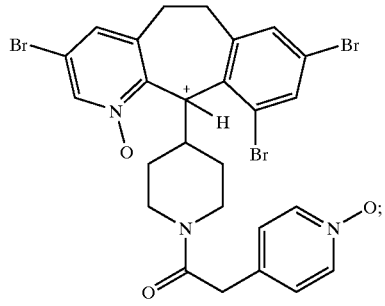
(74.0) 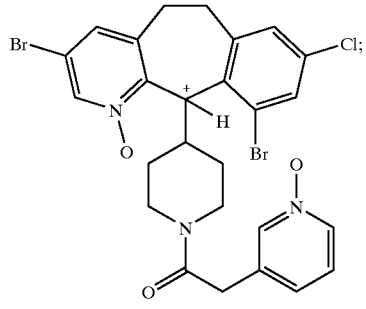
(75.0) 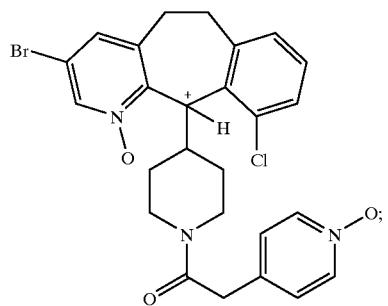
(76.0) 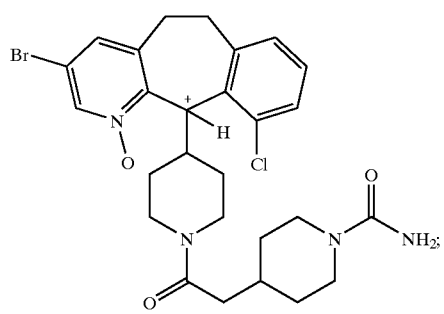
(77.0) 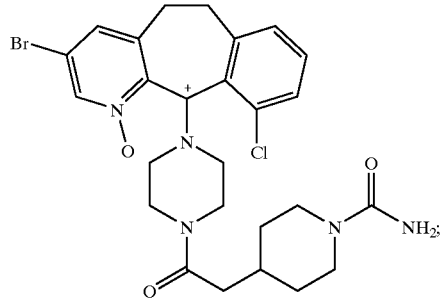
(78.0) 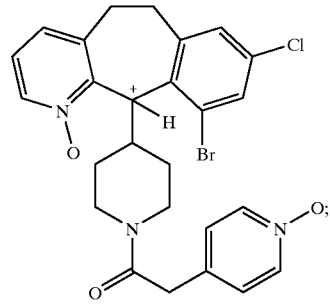
(79.0) 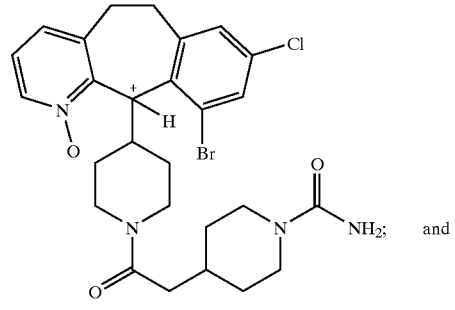
and -continued

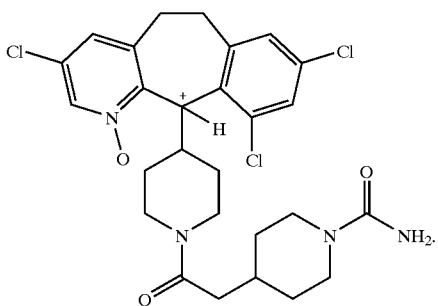

(80.0)

or pharmaceutically acceptable salts or solvates thereof.

U.S. application Ser. No. 08/877,741 filed Jun. 17, 1997, now abandoned, discloses compounds of the formula:

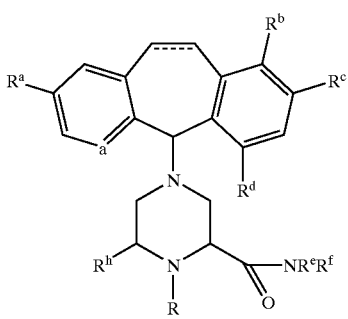

(1.0)

or a pharmaceutically acceptable salt or solvate thereof, wherein:

a represents N or NO⁻;

$R^a$, $R^b$, $R^c$, and $R^d$ dare the same or different, and are selected from the group consisting of H, halo, alkyl, and alkoxy, with the proviso that at least one, but not more than two of $R^a$, $R^b$, $R^c$ and $R^d$ are H;

the dotted line ( - - - ) represents an optional double bond;

R is selected from the group consisting of H, —S(O)₂R¹, —S(O)₂NR¹R¹, —C(O)R¹, and —C(O)NR¹R¹, wherein R¹ and R² are independently selected from the group consisting of H, alkyl, aryl, arylalkyl, heteroaryl, heteroarylalkyl, (C₃–C₇) cycloalkyl, cycloalkylalkyl, heterocycloalkyl, substituted alkyl, substituted aryl, substituted arylalkyl, substituted heteroaryl, substituted heteroarylalkyl, substituted (C₃–C₇) cycloalkyl, substituted cycloalkylalkyl, substituted heterocycloalkyl, wherein said substituted groups have one or more substituents selected from: alkyl, alkoxy, aralkyl, heteroarylalkyl, —NO₂, alkyloxyalkyl, alkyloxyalkyloxyalkyl, C₃–C₇ cycloalkyl, aryl, —CN, heteroaryl, heterocycloalkyl, =O, —OH, amino, substituted amino, nitro and halo;

$R^e$ and $R^f$ are independently selected from H, alkyl, alkyloxyalkyl, alkyloxyalkyloxyalkyl, aryl, arylalkyl, heteroaryl, heteroarylalkyl, (C₃-C₇) cycloalkyl, cycloalkylalkyl, heterocycloalkyl, substituted alkyl, substituted alkyloxyalkyl, substituted alkyloxyalkyloxyalkyl, substituted aryl, substituted arylalkyl, substituted heteroaryl, substituted heteroarylalkyl, substituted (C₃–C₇) cycloalkyl, substituted cycloalkylalkyl, substituted heterocycloalkyl, wherein said substituted groups have one or more substituents selected from: alkyl, alkoxy, aralkyl, heteroarylalkyl, —NO₂, alkyloxyalkyl, alkyloxyalkyloxyalkyl, C₃-C₇ cycloalkyl, aryl, —CN, heteroaryl, heterocycloalkyl, =O, —OH, amino, substituted amino, nitro and halo; or $R^e$ is selected from the group consisting of H, alkyl and aryl and $R^f$ is represented by —(CH₂)ₙ—R¹⁵, wherein n is an integer from 0 to 8 and R¹⁵ is selected from —C(O)NH₂, —SO₂NH₂, aryl, heteroaryl, cycloalkyl, heterocycloalkyl, optionally substituted by alkyl, alkoxy, aralkyl, heteroarylalkyl, —NO₂, alkyloxyalkyl, alkyloxyalkyloxyalkyl, C₃-C₇ cycloalkyl, aryl, —CN, heterocycloalkyl, =O, —OH, amino, substituted amino, nitro and halo;

or R¹⁵ is

wherein B is OH or NH₂ and A is NH, O, NOH or NCN, or R¹⁵ is NR¹⁶R¹⁷, wherein R¹⁶ is H or alkyl and R¹⁷ is H, alkyl, SO₂CH₃, or C(O)NH₂; or $R^e$ and $R^f$ together with the nitrogen to which they are bound, form a 5 or 6 membered heterocycloalkyl ring which is optionally substituted by OH, NH₂, NHR¹⁶, NHR¹⁷, NR¹⁶R¹⁷, or (CH₂)ₙR¹⁸R¹⁹, wherein R¹⁶ and R¹⁷ are as defined above, R¹⁸ is H or C₁–C₆ alkyl, and R¹⁹ is selected from H, C₁–C₆ alkyl, substituted alkyl, arylalkyl, acyl (e.g., acetyl, benzoyl, etc.), carboxamido, alkyloxycarbonyl (e.g., methoxycarbonyl), arylalkyloxycarbonyl (e.g., benzyloxycarbonyl), amido derivatives derived from amino acids (e.g., glycine,alnine, serine,etc.), imidate (e.g., phenoxyimidate), cyanide, imidamido (e.g., C(=NH)NH₂, (C=NSO₂NH₂)NH₂, etc.), sulfonamido (e.g., SO₂NH₂, SO₂N(CH₃)₂) sulfonyl (e.g., SO₂CH₃, SO₂C₆H₅, SO₂CH₂C₆H₅, etc.), phosphinate (e.g., P(=O)(CH₃)₂), heterocyclyl and imidamido (e.g., (C=NC₆H₅)C₆H₅), (C=NH)C₆H₅,etc.), wherein n is as defined above; and $R^h$ is H or =O; with the further proviso that when $R^h$ is H and $R^b$ and $R^d$ are both H, $R^e$ is H and

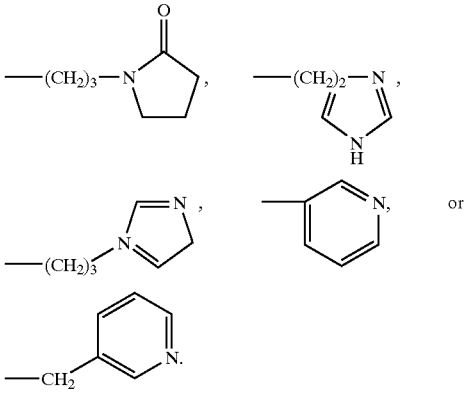

Compounds which are also P-gp inhibitors useful in this invention include compounds of formula 1.0:

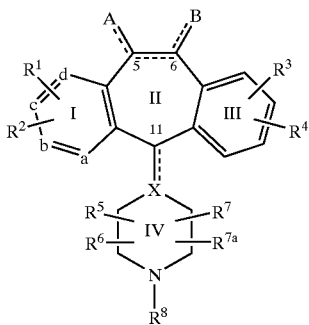

(1.0)

or a pharmaceutically acceptable salt or solvate thereof, wherein:
one of a, b, c and d represents N or $N^+O^-$, and the remaining a, b, c, and d groups represent C, wherein each carbon has an $R^1$ or $R^2$ group bound to said carbon; or
each of a, b, c, and d are C, wherein each carbon has an $R^1$ or $R^2$ group bound to said carbon;
The dotted lines ( - - - ) represent optional bonds;
X represents N or CH when the optional bond is absent, and represents C when the optional bond is present;
When the optional bond is present between carbon atom 5 and carbon atom 6 then there is only one A substituent bound to carbon atom 5 and there is only one B substituent bound to carbon atom 6 and A or B is other than H;
When the optional bond is not present between carbon atom 5 and carbon atom 6 single bond, then there are two A substituents bound to carbon atom 5, wherein each A substituent is independently selected and two B substituents bound to carbon atom 6, wherein each B substituent is independently selected;
A and B are independently selected from:
(1) —H;
(2) —$R^9$;
(3) —$R^9$—C(O)—$R^9$;
(4) —$R^9$—$CO_2$—$R^{9a}$;
(5) —$(CH_2)pR^{26}$;
(6) —$C(O)N(R^9)_2$, wherein each $R^9$ is the same or different;
(7) —$C(O)NHR^9$;
(8) —$C(O)NH$—$CH_2$—$C(O)$—$NH_2$;
(9) —$C(O)NHR^{26}$;
(10) —$(CH_2)pC(R^9)$—O—$R^{9a}$;
(11) —$(CH_2)p(R^9)_2$, wherein each $R^9$ is the same or different;
(12) —$(CH_2)pC(O)R^9$;
(13) —$(CH_2)pC(O)R^{27a}$;
(14) —$(CH_2)pC(O)N(R^9)_2$, wherein each $R^9$ is the same or different;
(15) —$(CH_2)pC(O)NH(R^9)$;
(16) —$(CH_2)pC(O)N(R^{26})_2$, wherein each $R^{26}$ is the same or different;
(17) —$(CH_2)pN(R^9)$—$R^{9a}$, (e.g. —$CH_2$—N(CH2-pyridine)-$CH_2$-imidazole);
(18) —$(CH_2)pN(R^{26})_2$, wherein $R^{26}$ is the same or different (e.g., —$(CH_2)p$—NH—$CH_2$—$CH_3$);
(19) —$(CH_2)pNHC(O)R^{50}$;
(20) —$(CH_2)pNHC(O)_2R^{50}$;
(21) —$(CH_2)pN(C(O)R^{27a})_2$ wherein each $R^{27a}$ is the same or different;
(22) —$(CH_2)pNR^{51}C(O)R^{27}$, optionally, $R^{51}$ and $R^{27}$, taken together with the atoms to which they are bound, form a heterocycloalkyl ring consisting of, 5 or 6 members, provided that when $R^{51}$ and $R^{27}$ form a ring, $R^{51}$ is not H;
(23) —$(CH_2)pNR^{51}C(O)NR^{27}$, optionally, $R^{51}$ and $R^{27}$, taken together with the atoms to which they are bound, form a heterocycloalkyl ring consisting or 5 or 6 members, provided that when $R^{51}$ and $R^{27}$ form a ring, $R^{51}$ is not H;
(24) —$(CH_2)pNR^{51}C(O)N(R^{27a})_2$, wherein each $R^{27a}$ is the same or different;
(25) —$(CH_2)pNHSO_2N(R^{51})_2$, wherein each $R^{51}$ is the same or different;
(26) —$(CH_2)pNHCO_2R^{50}$;
(27) —$(CH_2)pNC(O)NHR^{51}$;
(28) —$(CH_2)pCO_2R^{51}$;
(29) —$NHR^9$;
(30)

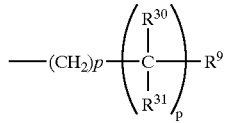

wherein $R^{30}$ and $R^{31}$ are the same or different;
(31)

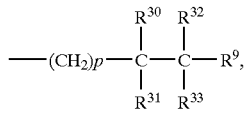

wherein $R^{30}$, $R^{31}$, $R^{32}$ and $R^{33}$ are the same or different;
(32) -alkenyl-$CO_2R^{9a}$;
(33) -alkenyl-$C(O)R^{9a}$;
(34) -alkenyl-$CO_2R^{51}$;
(35) -alkenyl-$C(O)$—$R^{27a}$;
(36) $(CH_2)$p-alkenyl-$CO_2$—$R^{51}$;
(37) —$(CH_2)pC$=$NOR^{51}$ or
(38) —$(CH_2)$p-Phthalimid;
p is 0, 1, 2, 3 or 4;
Each $R^1$ and $R^2$ is independently selected from H, Halo, —$CF_3$,
—$OR^{10}$, $COR^{10}$, —$SR^{10}$, —$S(O)_tR^{15}$ (wherein t is, 0, 1 or 2, —$N(R^{10})_2$, —$NO_2$,
—$OC(O)R^{10}$, $CO_2R^{10}$, —$OCO_2R^{15}$, —CN, —$NR^{10}COOR^{15}$, —$SR^{15}C(O)OR^{15}$,
—$SR^{15}N(R^{13})_2$ (provided that $R^{15}$ in —$SR^{15}N(R^{13})_2$ is not —$CH_2$) wherein each $R^{13}$ is independently selected from H or —$C(O)OR^{15}$, benzotriazol-1-yloxy, tetrazol-5-ylthio, or substituted tetrazol-5-ylthio, alkynyl, alkenyl or alkyl, said alkyl or alkenyl group optionally being substituted with halo, —$OR^{10}$ or —$CO_2R^{10}$;
$R^3$ and $R^4$ are the same or different and each independently represents H, any of the substituents of $R^1$ and $R^2$;
$R^5$, $R^6$, $R^7$ and $R^{7a}$ each independently represents H, —$CF_3$,
—$COR^{10}$, alkyl or aryl, said alkyl or aryl optionally being substituted with
—$OR^{10}$, —$SR^{10}$, —$S(O)_tR^{15}$, —$NR^{10}COOR^{15}$, —$N(R^{10})_2$, —$NO_2$, —$C(O)R^{10}$, —OCOR$^{10}$, —OCO$_2$R$^{15}$, —CO$_2$R$^{10}$, OPO$_3$R$^{10}$, or R$^5$ is combined with R$^6$ to represent =O or =S;

R$^8$ is selected from:

H, (2.0)
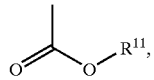

(3.0)
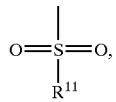

(4.0)
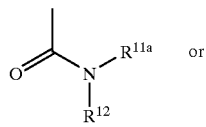 or (5.0)
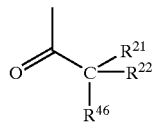

R$^9$ is selected from:
(1) heteroaryl;
(2) substituted heteroaryl;
(3) arylalkoxy;
(4) substituted arylalkoxy;
(5) heterocycloalkyl;
(6) substituted heterocycloalkyl;
(7) heterocycloalkylalkyl;
(8) substituted heterocycloalkylalkyl;
(9) heteroarylalkyl;
(10) substituted heteroarylalkyl;
(11) heteroarylalkenyl;
(12) substituted heteroarylalkenyl;
(13) heteroarylalkynyl or
(14) substituted heteroarylalkynyl;

wherein said substituted R$^9$ groups are substituted with one or more (e.g. 1, 2 or 3) substituents selected from:
(1) —OH;
(2) —CO$_2$R$^{14}$;
(3) —CH$_2$OR$^{14}$,
(4) halo (e.g. Br, Cl or F),
(5) alkyl (e.g. methyl, ethyl, propyl, butyl or t-butyl);
(6) amino;
(7) trityl;
(8) heterocycloalkyl;
(9) cycloalkyl, (e.g. cyclopropyl or cyclohexyl);
(10) arylalkyl;
(11) heteroaryl;
(12) heteroarylalkyl or

(13)
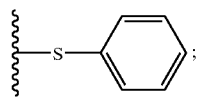

wherein R$^{14}$ is independently selected from: H; alkyl; aryl, arylalkyl, heteroaryl or heteroarylalkyl;

R$^{9a}$ is selected from: alky or arylalkyl;

R$^{10}$ is selected from: H; alkyl; aryl or arylalkyl;

R$^{11}$ is selected from:
(1) alkyl;
(2) substituted alkyl;
(3) aryl;
(4) substituted aryl;
(5) cycloalkyl;
(6) substituted cycloalkyl;
(7) heteroaryl;
(8) substituted heteroaryl;
(9) heterocycloalkyl; or
(10) substituted heterocycloalkyl;

wherein said substituted R$^{11}$ groups have 1, 2 or 3, substituents selected from:
(1) —H;
(2) halo or
(3) alkyl;

R$^{11a}$ is selected from:
(1) H;
(2) OH;
(3) alkyl;
(4) substituted alkyl;
(5) aryl;
(6) substituted aryl;
(7) cycloalkyl;
(8) substituted cycloalkyl;
(9) heteroaryl;
(10) substituted heteroaryl;
(11) heterocycloalkyl; or
(12) substituted heterocycloalkyl;

wherein said substituted R$^{11a}$ groups have 1, 2 or 3, substituents selected from:
(1) —OH;
(2) —CN;
(3) —CF$_3$;
(4) halo;
(5) alkyl;
(6) cycloalkyl;
(7) heterocycloalkyl;
(8) arylalkyl;
(9) heteroarylalkyl;
(10) alkenyl or
(11) heteroalkenyl;

R$^{12}$ is selected from: H, or alkyl;

R$^{15}$ is selected from: alkyl or aryl;

$R^{21}$, $R^{22}$ and $R^{46}$ are independently selected from:
(1) —H;
(2) alkyl;
(3) aryl;
(4) substituted aryl,
  optionally substituted with one or more substituents selected from: alkyl, halo, CF3 or OH;
(5) cycloalkyl;
(6) substituted cycloalkyl;
  optionally substituted with one or more substituents selected from: alkyl, halo, CF3 or OH;
(7) heteroaryl of the formula,

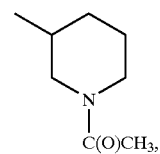

(9) heterocycloalkyl of the formula:

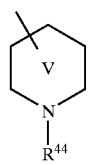

wherein $R^{44}$ is selected from:

(1) —H;
(2) alkyl;
(3) alkylcarbonyl;
(4) alkyloxy carbonyl;
(5) haloalkyl or
(6) —C(O)NH($R^{51}$);
when $R^{21}$, $R^{22}$ or $R^{46}$ is the heterocycloalkyl of the formula above (i.e. Ring V), Ring V includes:

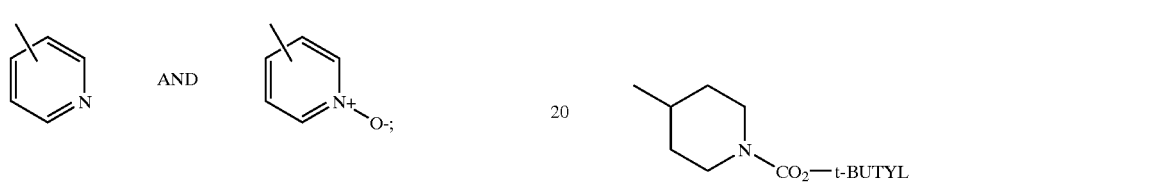

Examples of Ring V include:

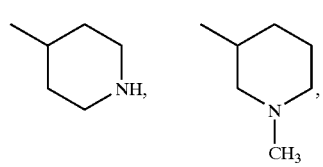

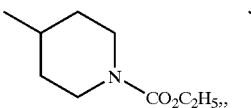

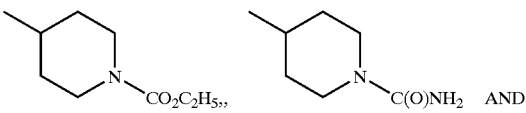

$R^{26}$ is independently selected from:
(1) —H;
(2) alkyl;
(3) alkoxyl;
(4) —CH$_2$—CN;
(5) $R^9$;
(6) —CH$_2$CO$_2$H;
(7) —C(O)alkyl or
(8) CH$_2$CO$_2$alkyl;

$R^{27}$ is independently selected from:
(1) —H;
(2) —OH;
(3) alkyl or
(4) alkoxy;

$R^{27a}$ is independently selected from:
(1) alkyl or
(2) alkoxy;

$R^{30}$ through $R^{33}$ is independently selected from:
(1) —H;
(2) —OH;
(3) =O;
(4) alkyl;
(5) aryl or
(6) arylalkyl;

$R^{50}$ is independently selected from:
(1) alkyl;
(2) heteroaryl;
(3) substituted heteroaryl or
(4) amino;

wherein said substituents on said substituted $R^{50}$ groups are independently selected from: alkyl; halo; or —OH;

$R^{50a}$ is independently selected from:
(1) heteroaryl;
(2) substituted heteroaryl or
(3) amino;
$R^{51}$ is selected from: —H, or alkyl.
Representative examples of the compounds of formula 1.0 include:

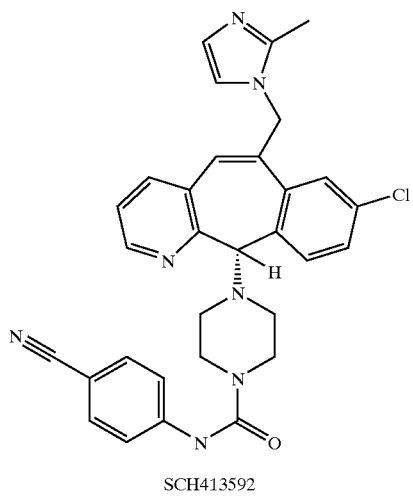

SCH413592

Other Specific Compounds
Preferred compounds of formula 1.0 are as follows:

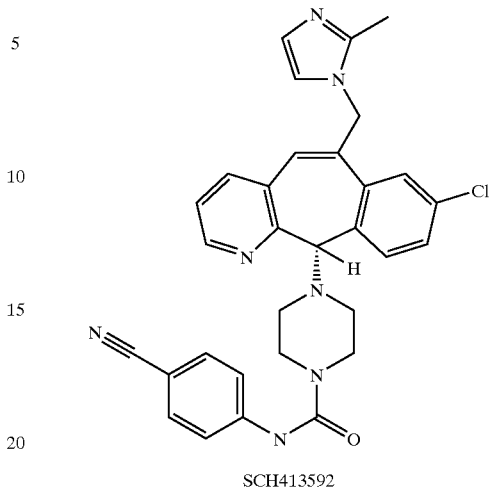

SCH413592

The following processes may be employed to produce compounds of formula 1.0.

Pyridyl Tricyclic Compounds

One skilled in the art will appreciate that the compounds of the invention represented by Formula 1, wherein one of a, b, c or d is N or $N^+$—$O^-$ can be prepared according to the following schemes:

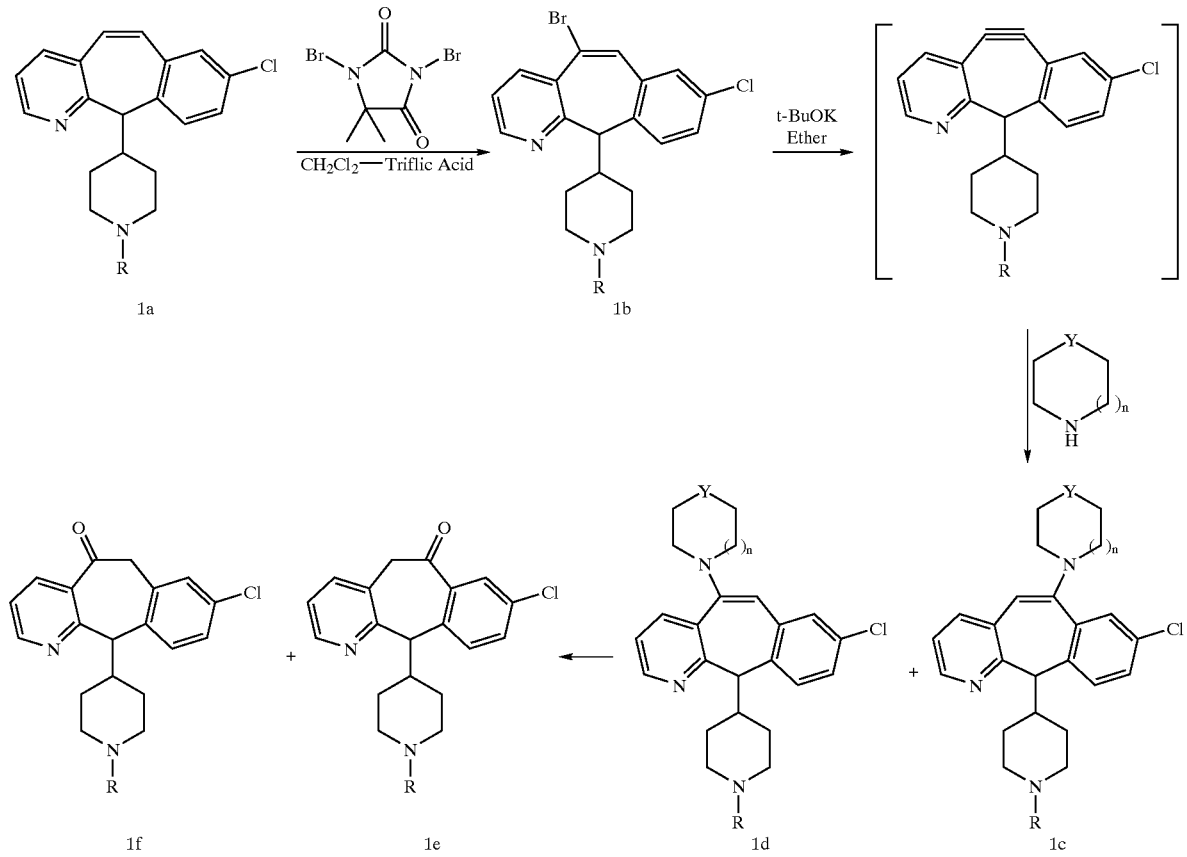

The synthesis of 5-bromo tricyclic compound 1b begins with bridgehead olefin 1a (*J. Med Chem* (1998), 41,1561–1567) which is treated with dibromo dimethylhydantoin in triflic acid media. Further treatment of the vinyl-bromide with potassium t-butoxide in the presence of the appropriate secondary amine gives the 5 and 6-substituted enamine adducts. When Y is NH (piperazine case), acylations, sulfonylations and amide formation can be carried out using standard procedures. Treatment of these amine adducts with HCl(aq) at the appropriate temperatures results in the formation of the 5 and 6 azaketones, 1f and 1e respectively.

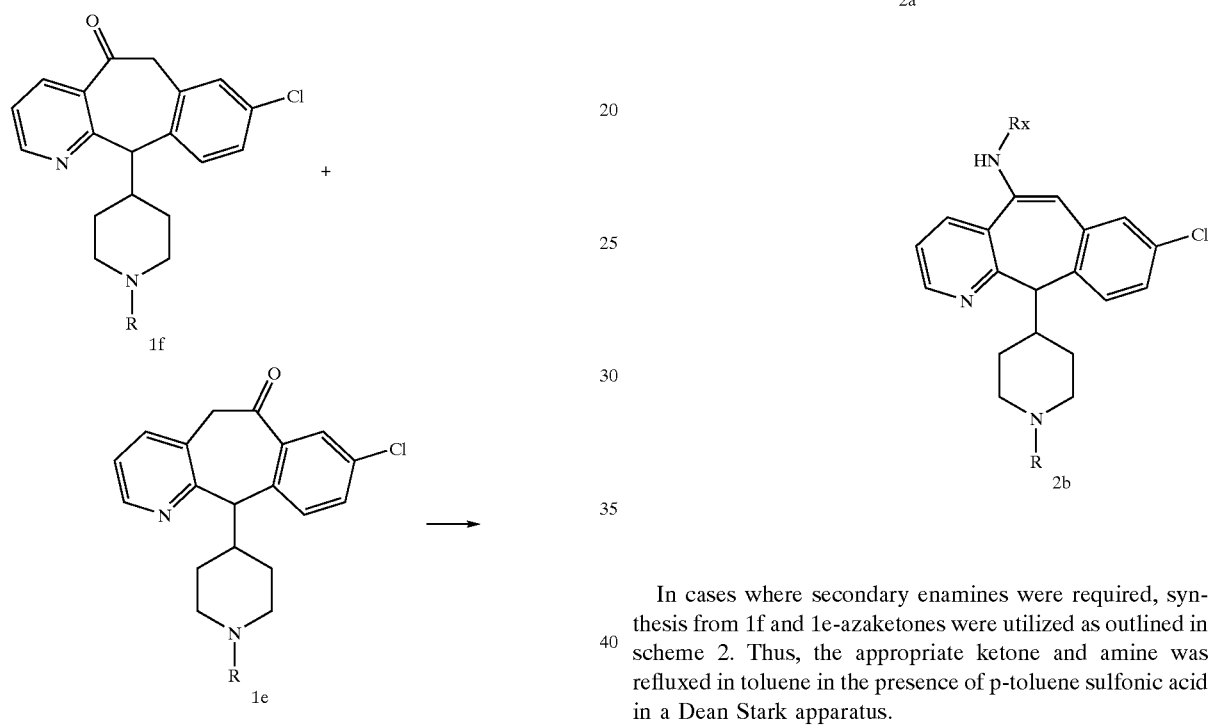

Scheme 2

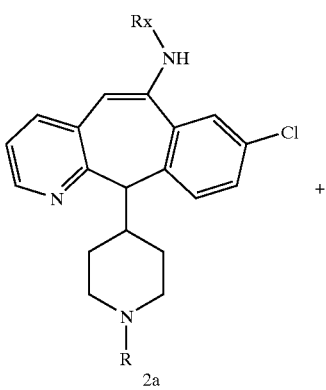

In cases where secondary enamines were required, synthesis from 1f and 1e-azaketones were utilized as outlined in scheme 2. Thus, the appropriate ketone and amine was refluxed in toluene in the presence of p-toluene sulfonic acid in a Dean Stark apparatus.

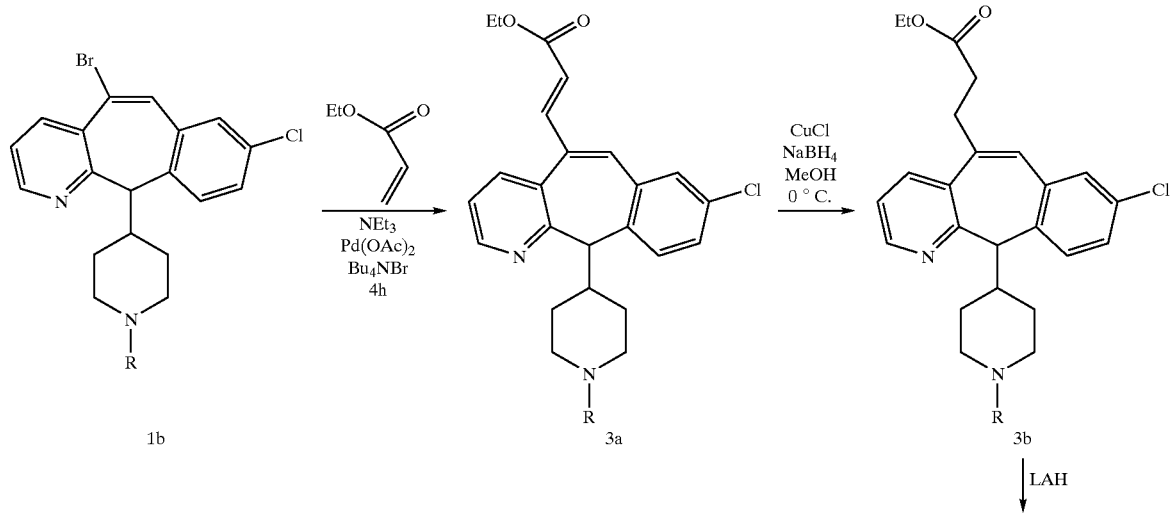

Scheme 3:

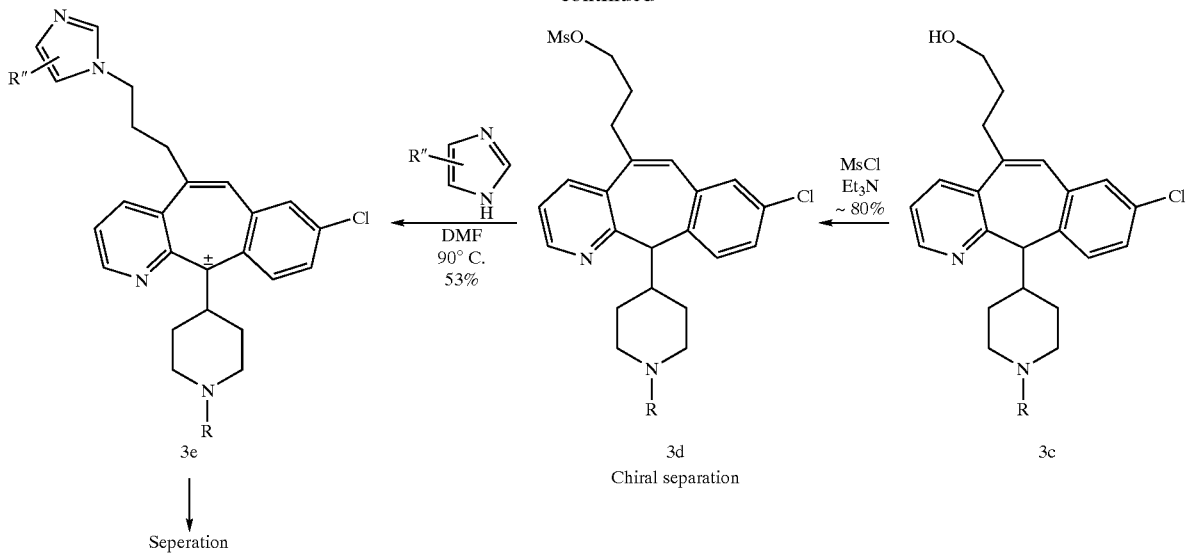

3e Seperation

3d Chiral separation

3c

Synthesis of 3-carbon spaced analogs can be prepared as outlined in scheme 3. Thus, subjecting tricyclic vinyl bromide 1b to a Heck type reaction using ethyl acrylate and catalyzed by Pd⁰ gives the—un-saturated ester 3a. Reduction of the conjugated double bond was carried out using copper chloride-sodium borohydride reducing reagent. The ester was further reduced to alcohol using lithium aluminum hydride. Treatment of the alcohol with methanesulfonyl chloride in an appropriate aprotic solvent, followed by displacement with an appropriate sodium salt resulted in the desired imidazole targets. In most cases, separation of isomers were effected at this point. Where the R group of 3e was a BOC group, deprotection using HCl-dioxane gave the hydrochloride salts of amines. Using standard chemistry, these amines were converted to ureas, carbamates, sulfonamides and amides.

Scheme 4:
PREPARATION OF 6-SUBSTITUTED CARBON ANLOGUES:

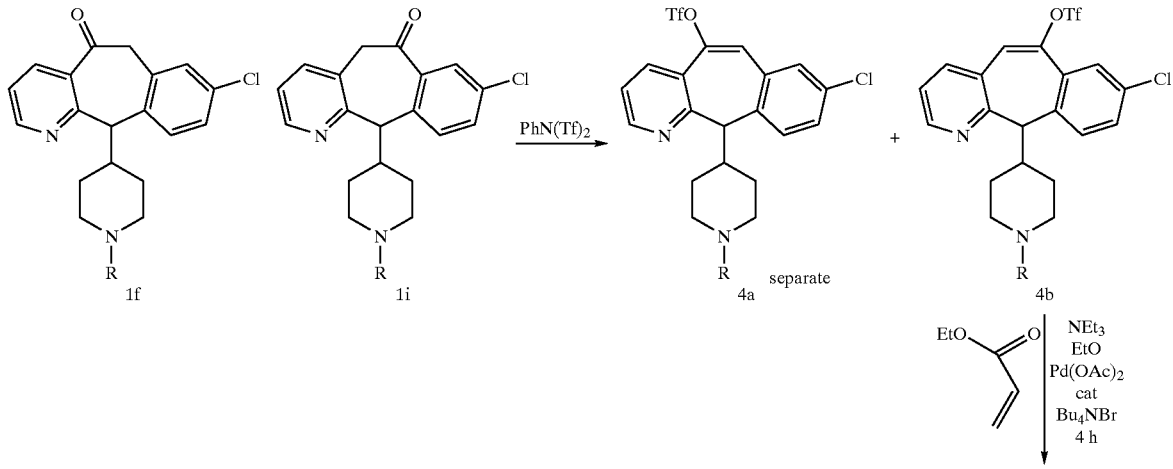

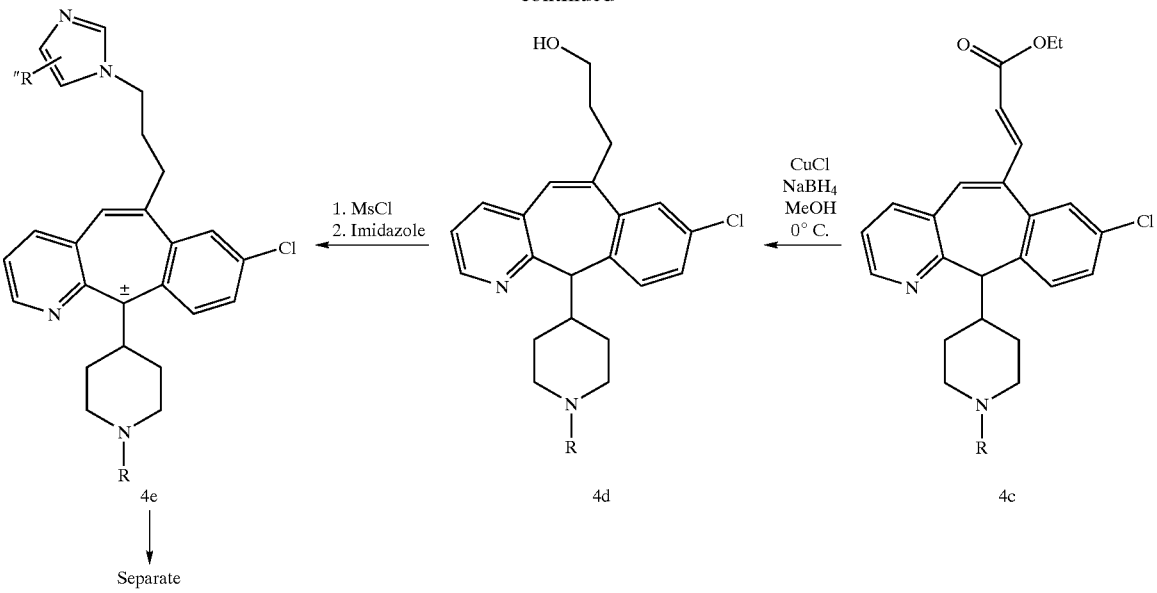

Preparation of 6-substituted 3-carbon spaced imidazole compounds was carried out as outlined in scheme 4. A mixture of ketones 1f and 1i were treated with N-phenytrifluoromethane sulfonimide to give a seperable mixture of 5 and 6-tricyclic triflate compounds. The 6-trilate adduct was converted to the desired 3-carbon spaced analogs using similar protocol as described for the 5-bromo tricyclic compounds outlined in scheme 3.

Scheme 5:
SYNTHESIS OF 2-CARBON SPACER ANALOGUES

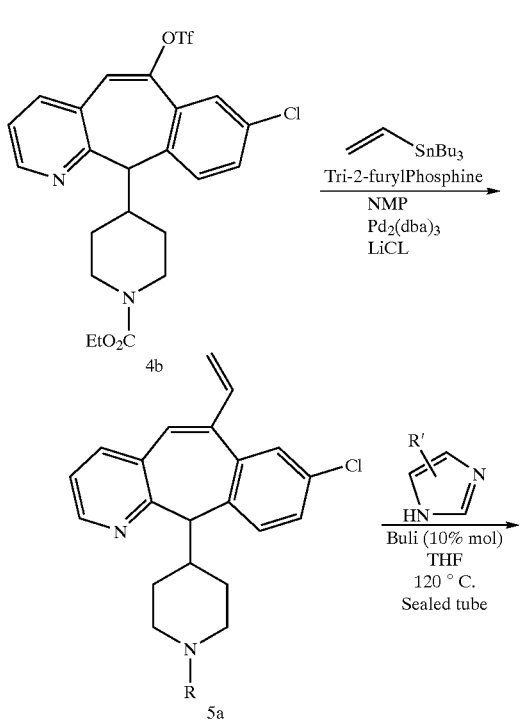

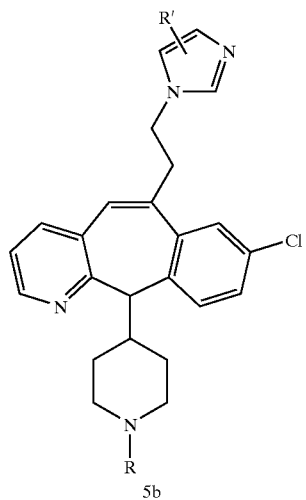

Two carbon spaced analogs were prepared as outlined in scheme 5. Thus, triflate 4b was subjected to Stille chemistry, by reacting with tributylvinyl stannate catalyzed by an appropriate $Pd^0$ to afford the tricyclic vinyl compound 5b. The 2-carbon spaced compounds were obtained by treating the tricylic compound with the appropriate imidazole that had been previously treated with Buli-THF in a sealed tube and refluxed at 120 C. Further funtionalization was carried out as previously described. Suberane compounds were prepared in a similar way.

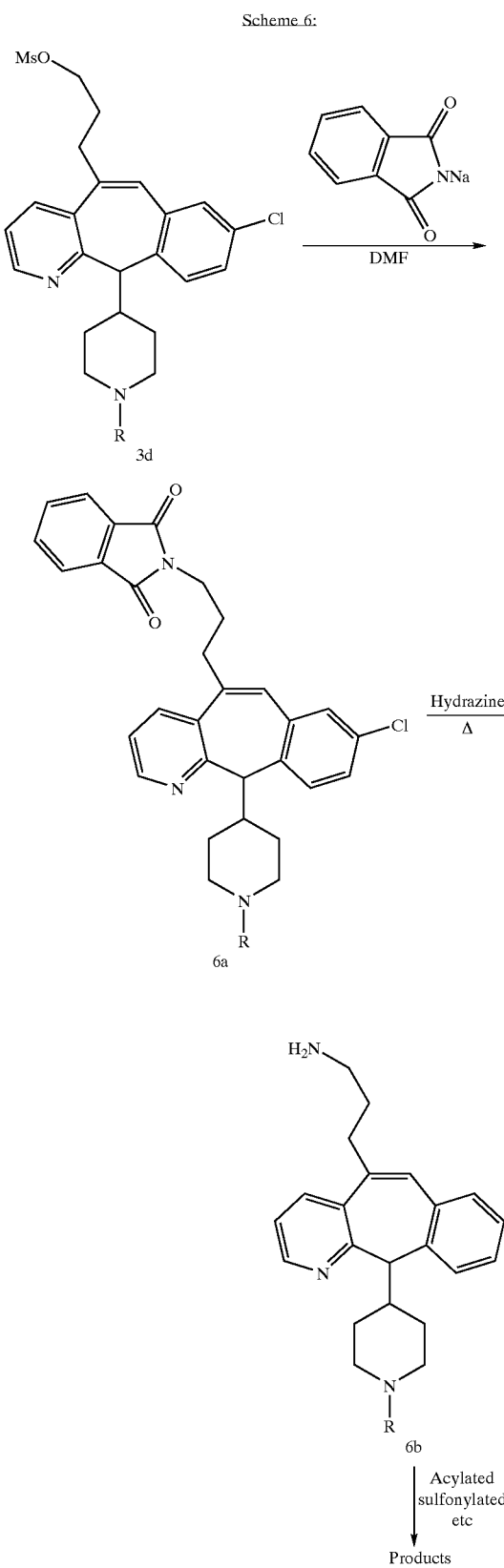
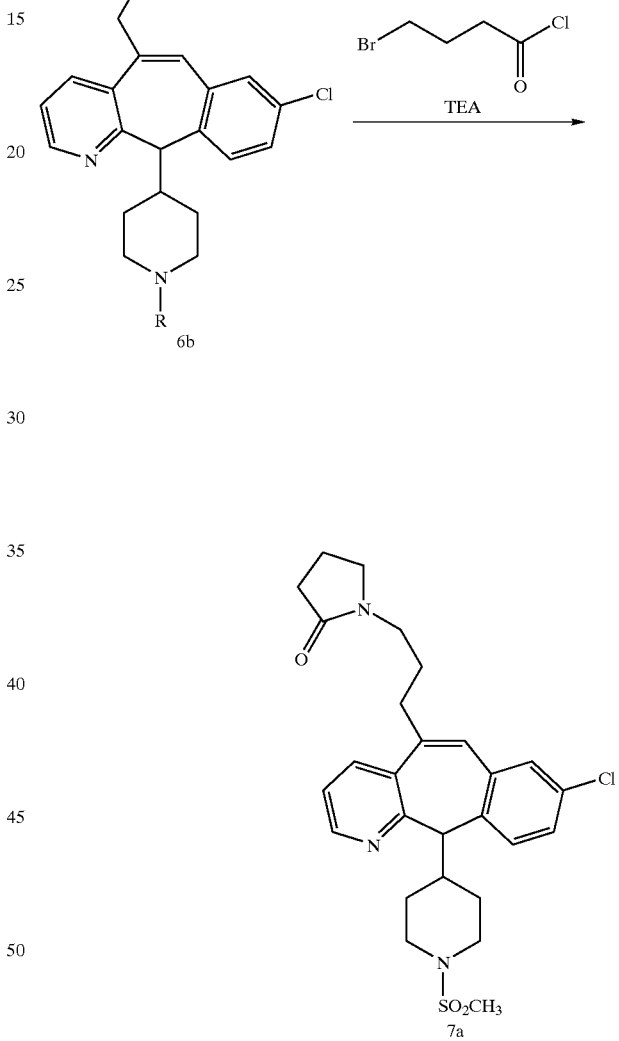
Scheme 6 illustrates method of making amine 6b through phthalimido displacement of a mesylate followed by hydazine hydrolysis of the phthalimido moiety. Amine 6b can be converted to targets that have acyl, sufonyl, carbamoyl and urea functionalities.
Lactams 7a can be prepared from amine 6b by reacting with bromo butanonyl acid chloride as outlined in scheme 7.

Scheme 8: Preparation of cyclic ureas
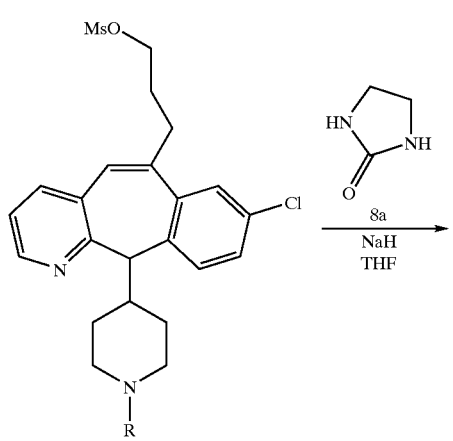
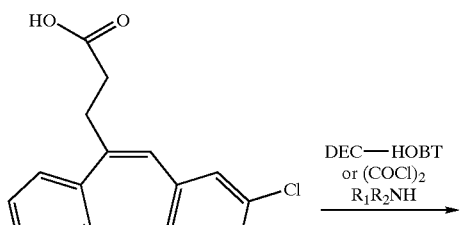
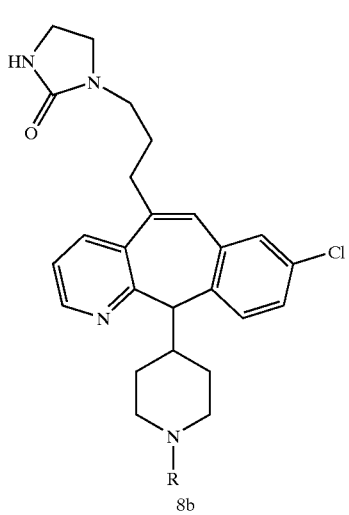
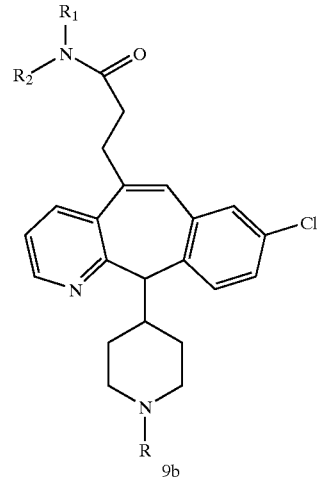
Cyclic urea can be prepared from the mesylate shown above by treating with the salt of the cyclic urea 8a as outlined in scheme 8.
Scheme 9:
PREPARATION OF 5-SUBSTITUTED
PROPANOIC ACID DERIVATIVES
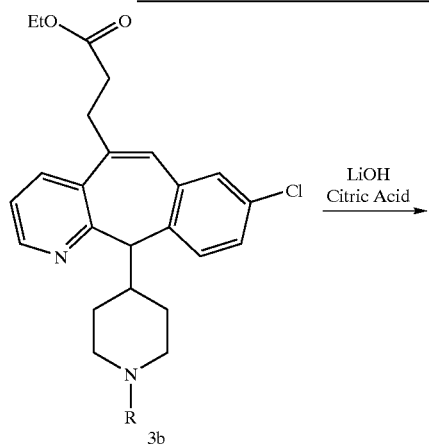
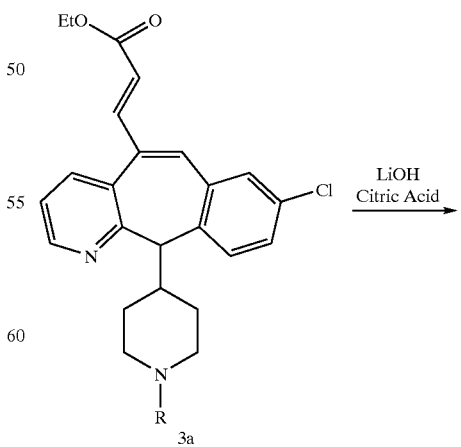

75
-continued
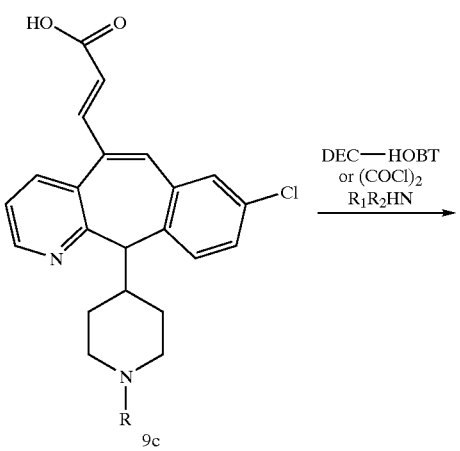
9c
76
-continued
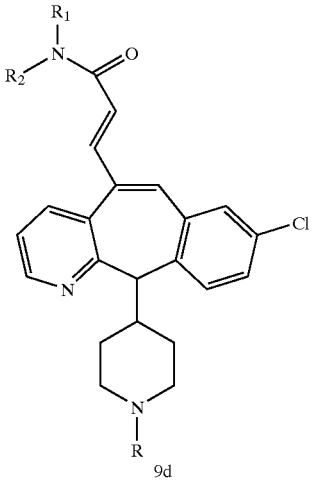
9d
Amides from 3-carbon spaced carboxylic acid 9a and 9c can be prepared as outlined in scheme 10 using either DEC-HOBT mediated protocol or from the appropriate acid chloride.
Scheme 10:
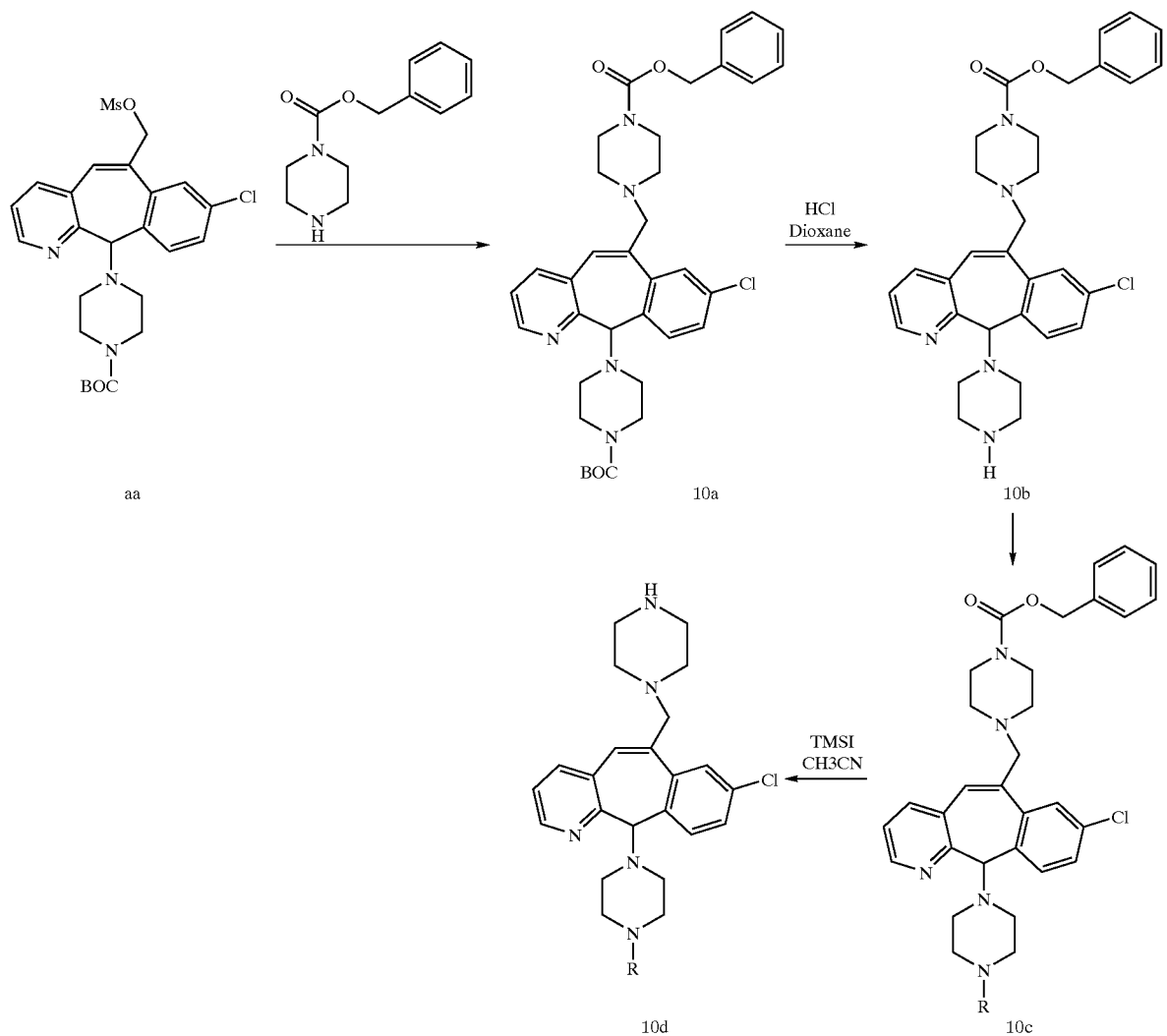

Preparation of piperazine compounds off the bridgehead starts from mesylate aa which is reacted with CBZ-protected piperazine. The BOC group is then removed and the resulting amine 10c is functionalized appropriately. Removal of CBZ group off the piperazine is effected with TMSI.
Scheme 11:
C-SUBSTITUTED IMIDAZOLE-3-METHYLENE-PIPERIDINES
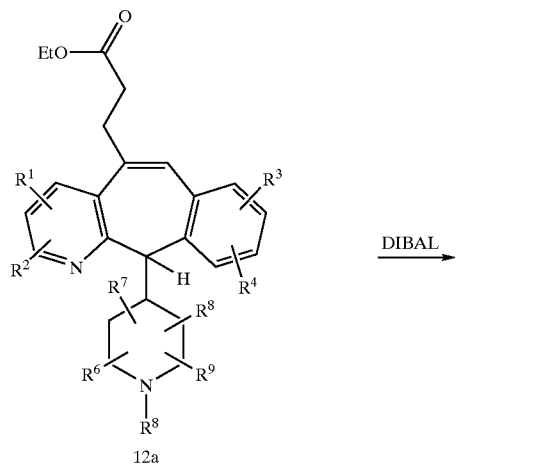
12a
DIBAL
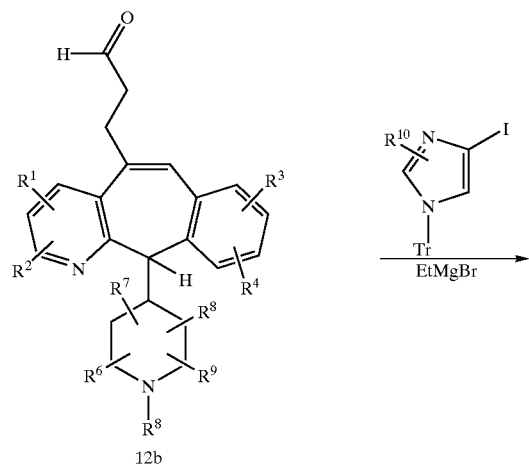
12b
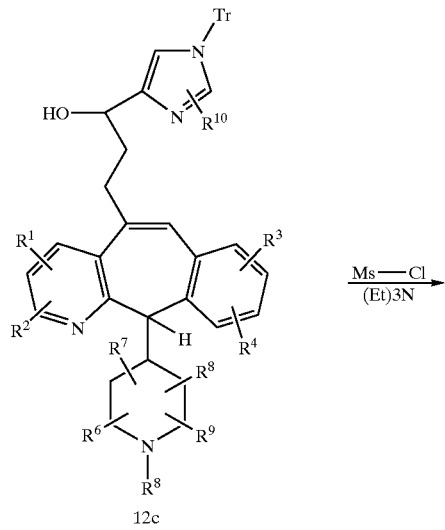
12c
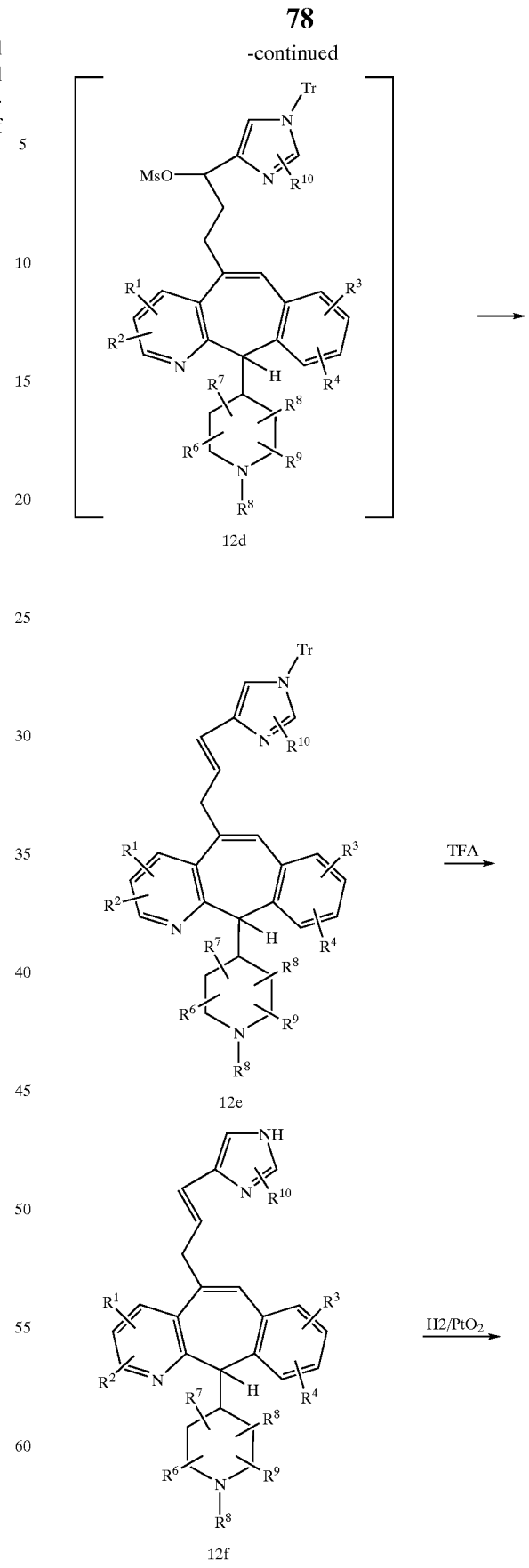
12d
12e
12f

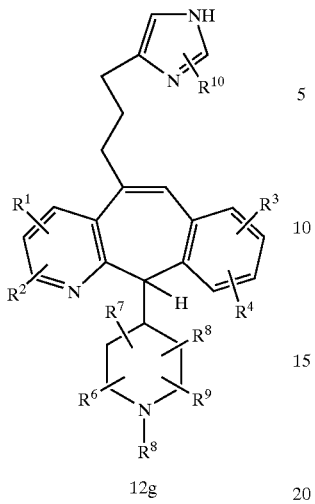

12g

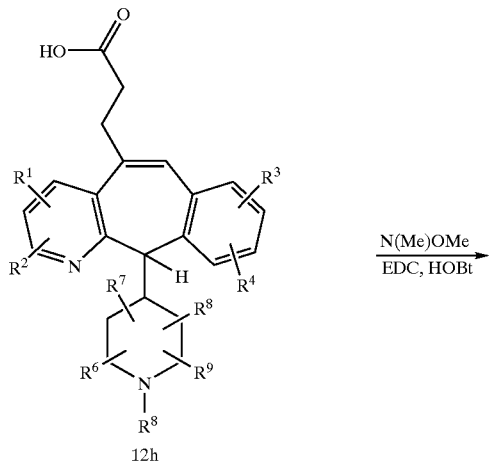

12h

Compound 12a is reduced with DIBAL in an inert solvent such as toluene or tetrahydrofuran to give 12b after acidic workup. Treatment of 12b with an appropriately substituted and tritylated imidazole iodide in the presence of ethylmagnesium bromide in solvents such as dichloromethane at ambient temperature yields the adduct 12c. Elimination of the hydroxyl group by converting the hydroxyl group to an appropriate leaving group such as a mesylate, tosylate, or halide, using methanesulfonyl chloride, p-toluenesulfonyl chloride, or thionyl chloride, followed by elimination using an appropriate base such as triethylamine gives 12e. Removal of the trityl group with acid such as trifluoroacetic acid or hydrochloric acid gives the double bond compound 12f which is then hydrogenated using an appropriate catalyst such as platinum oxide under from 1 to 55 psi of hydrogen in an appropriate solvent such as ethanol gave the desired product 12g.

Alternatively the ester 12a can be saponified with an appropriate base such as lithium hydroxide to obtain the acid 12h. Converting the acid 12h to the "Weinreb amide" followed by reaction with an appropriately substituted and tritylated imidazole iodide in the presence of ethylmagnesium bromide in solvents such as dichloromethane at ambient temperature yields the adduct 12c (shown in Scheme 12 below).

Scheme 12:

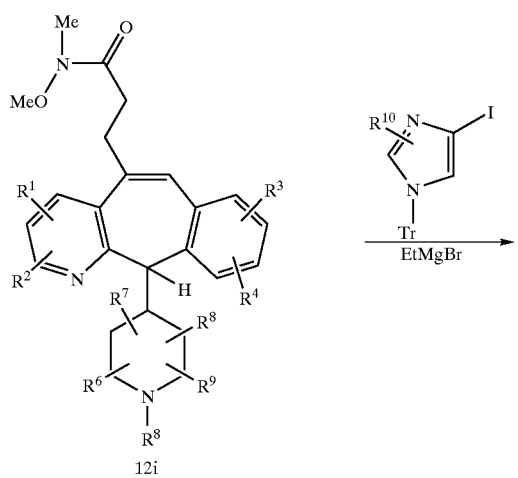

12i

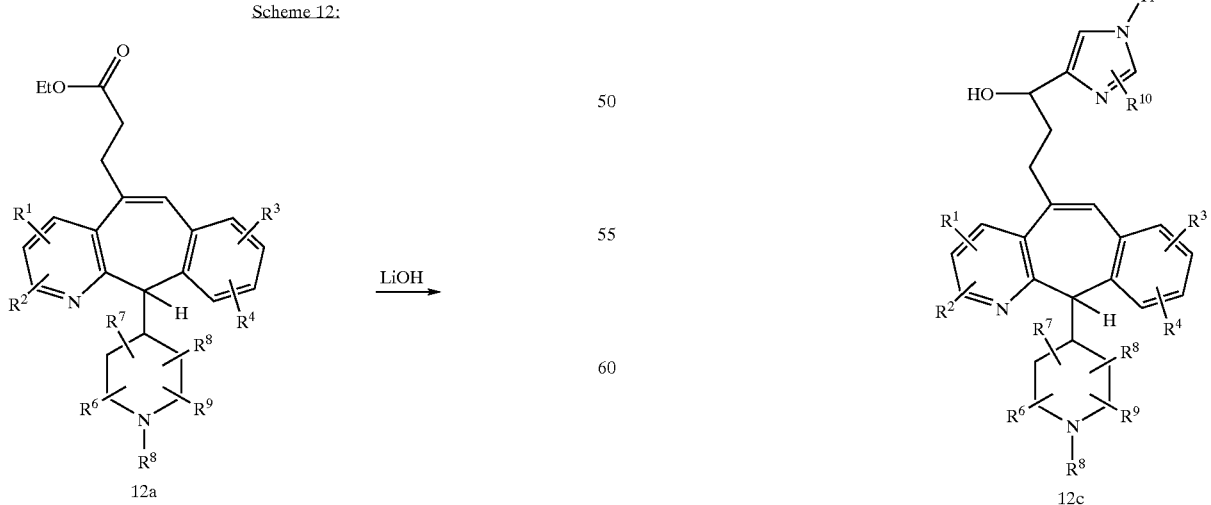

Scheme 12a

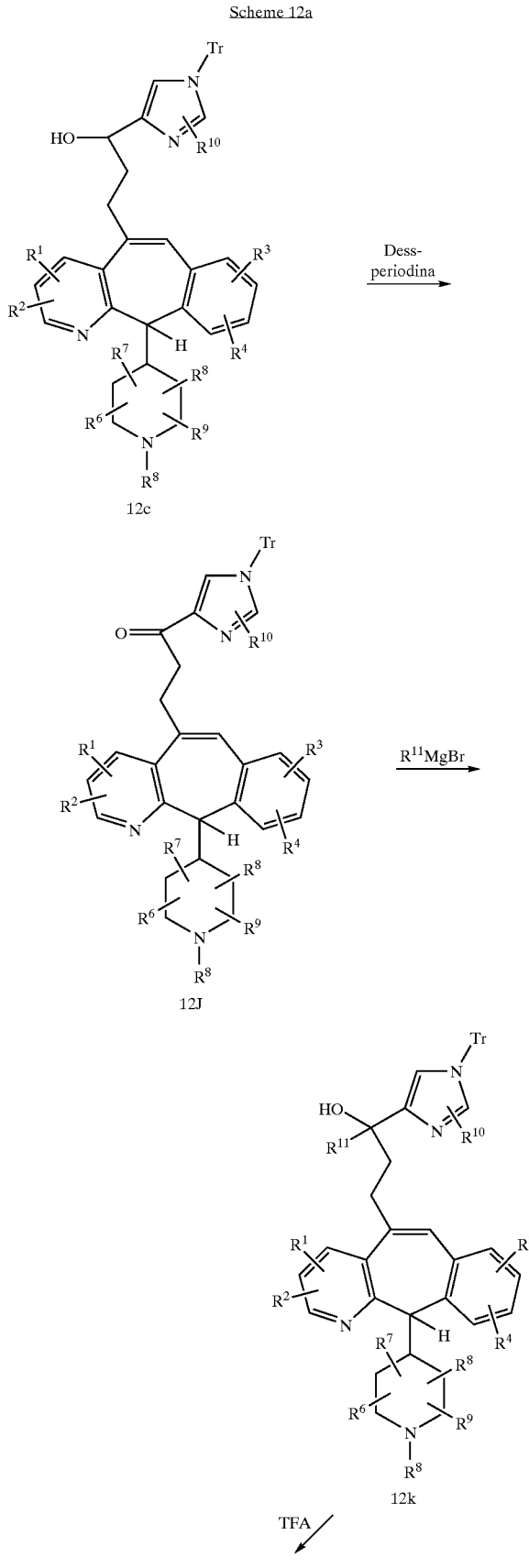

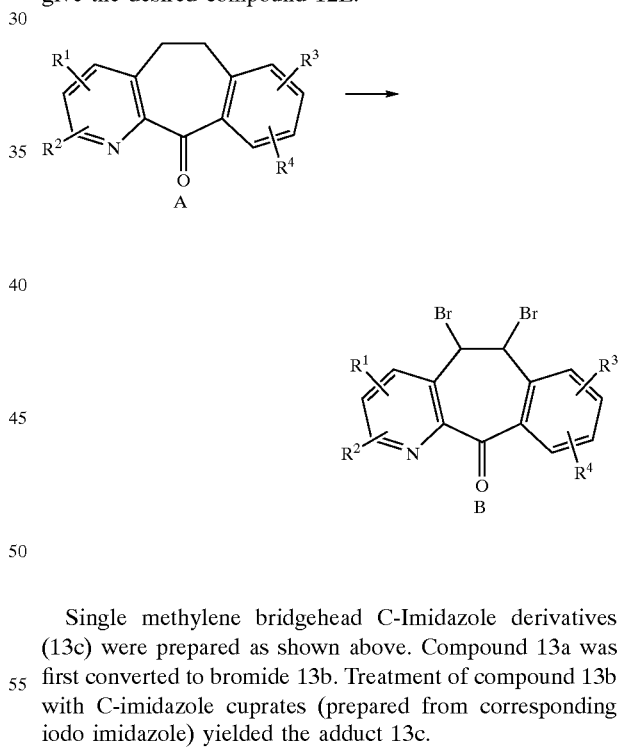

Compounds of type 12L were prepared as shown above. Oxidation of the hydroxyl compound 12c can be accomplished with the Dess Martin periodinane to obtain 12j. Reaction with a grignard reagent gave 12k. The trityl group is removed under standard conditions mentioned above to give the desired compound 12L.

Single methylene bridgehead C-Imidazole derivatives (13c) were prepared as shown above. Compound 13a was first converted to bromide 13b. Treatment of compound 13b with C-imidazole cuprates (prepared from corresponding iodo imidazole) yielded the adduct 13c.

Scheme 14: Preparation of One-methylene Piperazines

Ketone A is brominated with brominating reagents such as NBS, with a small amount of an activator such as benzoyl peroxide, in solvents such as dichloromethane at elevated temperature, such as 80–100° C. to give dibromo compound B.

Scheme 13:
C- Substituted Imidazole Single Methylene Bridgehead Compounds

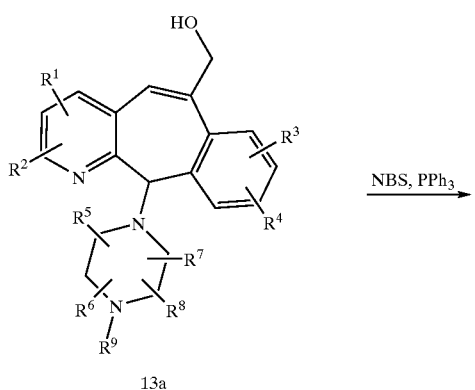

13a

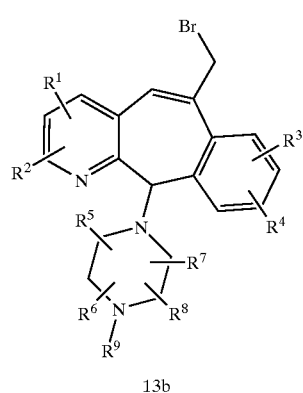

13b

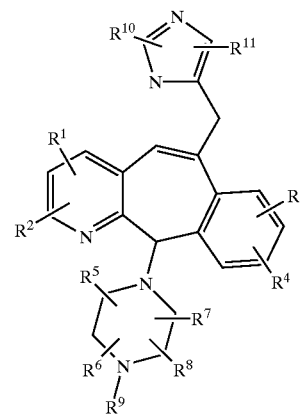

13c

Dibromo compound B is reacted with a base such as DBU in a solvent such as dichloromethane at temperatures from 0° C. to room temperature to give vinylbromides C and D. These vinylbromides are separated by chromatography such as silica gel flash chromatography using solvents mixtures such as ethyl acetate and hexane. Alternatively, vinylbromides C and D can be separated by crystallization from solvents such as dichloromethane.

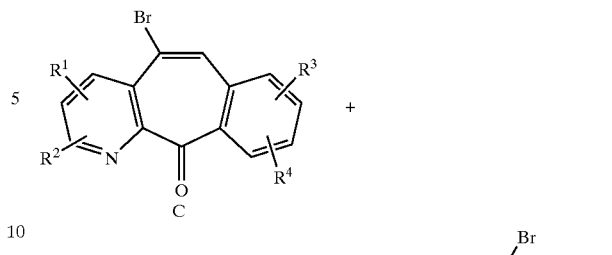

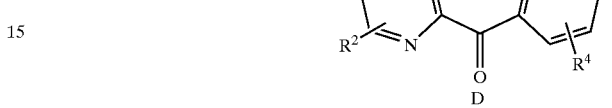

The ketone groups of separated vinylbromides C and D are reduced to the corresponding alcohols E and F with a reducing agent such as $NaBH_4$ in solvents such as methanol or ethanol at temperatures of 0° C. to room temperature.

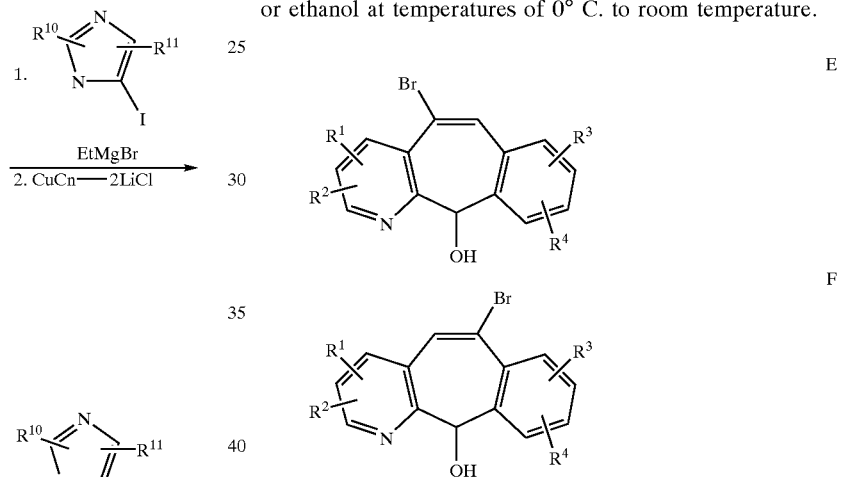

The resulting alcohols functions of E and F are converted to a leaving group, such as a halide, with reagents such as $SOCl_2$ in solvents such as dichloromethane containing a base such as 2,6-lutidine and running the reaction at 0C. to room temperature. The resulting intermediate halides are reacted, without purification, with piperazine or a protected piperazine, such as BOC-piperazine in a solvent such as dichloromethane at room temperature giving intermediates G and H.

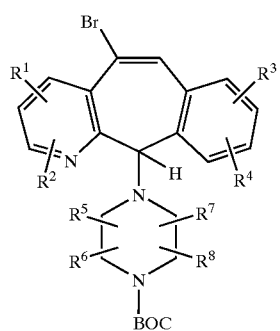

-continued

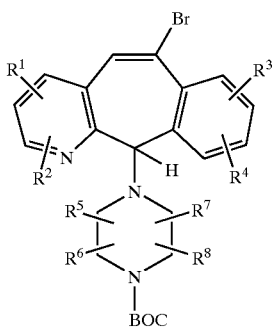
H

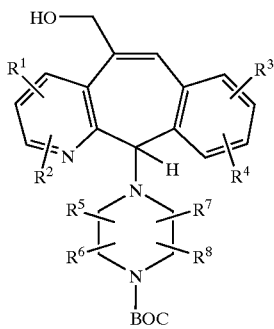
K

The vinylhalide intermediates are carbonylated with CO gas under a pressure of about 100 psi and a temperature of 80° C. to 100° C. using a palladium catalyst such as PdCl₂ and triphenyl phosphine in toluene and containing DBU and an alcohol such as methanol. If methanol is used, methyl esters I and J are obtained.

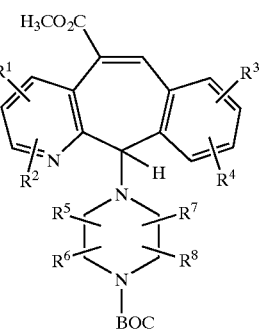
I

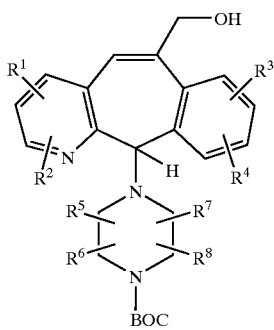
L

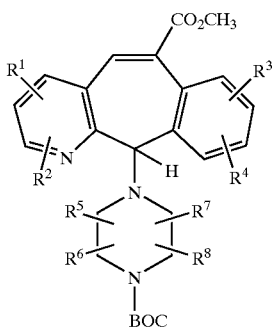
J

The hydroxy functions of K and L are converted into leaving groups such as a methanesulfonate or an arylsulfonate such as a tosylate, by reacting with the appropriate sulfonyl chloride in dichloromethane containing a base such as triethylamine. The sulfonate leaving groups can be displaced by nucleophiles such amines. The nucloephile can also be basic heterocycles such as imidazole or a substituted imidazole. In the case of an imidazole, the anion of the imidazole is first formed with NaH in DMF and then reacted with the above sulfonate. Displacement of the sulfonates with a nucleophile gives O and P, which can be converted to the compounds of this invention 1.0, by first removing the BOC protecting group and then forming the desired amide, urea, carbamate or sulfonamide on the resulting amine by methods well known in the art.

The ester functions are of I and J are reduced to hydroxymethyl functions of K and L. This can be done directly by first removing the protecting BOC group with TFA or HCl-dioxane and then reducing with a reducing agent such as DIBAL-H, followed by reintroduction of the BOC group with di-tert-butyl dicarbonate. Alternatively, the ester function is hydrolyzed with LiOH and water followed by neutralization with citric acid. The resulting carboxylic acids are then converted into a function that is easily reduced, such as a mixed anhydride or an acyl imidazole. This is done by reacting the resulting carbocylic acids with a chloroformate to form the mixed anhydride or with carbonydiimidazole to form the acyl imidazole (Synlett. (1995), 839). The resulting activated carboxylic acids are reduced with NaBH₄ in solvents such as methanol, ethanol or aqueous THF.

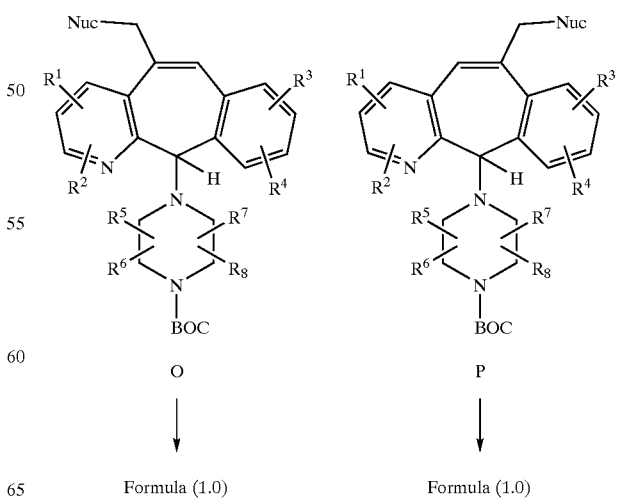

Scheme 15:
Preparation of one-methylene piperidenes

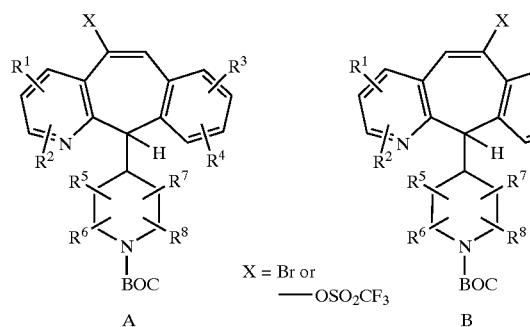

X = Br or —OSO₂CF₃

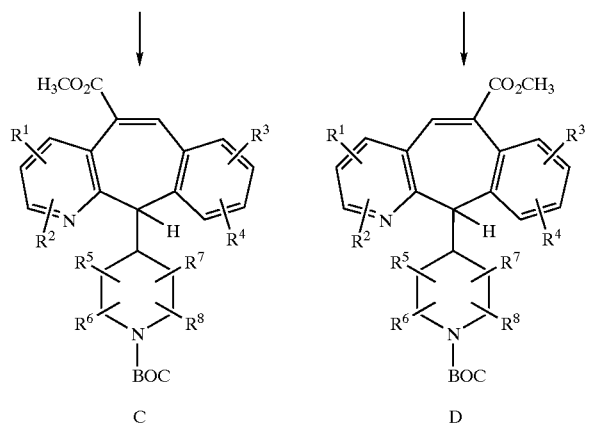

The vinylhalide or vinyltriflate intermediates A and B, (described in other general schemes) are carbonylated with CO gas under a pressure of about 100 psi and a temperature of 80° C. to 100° C. using a palladium catalyst such as PdCl₂ and triphenyl phosphine in toluene and containing DBU and an alcohol such as methanol. If methanol is used, methyl esters C and D are obtained. Intermediates C and D are reacted as are intermediates I and J in the general scheme for one methylene piperazines to yield compounds of Formula 1.0, of this invention.

Scheme 15a:

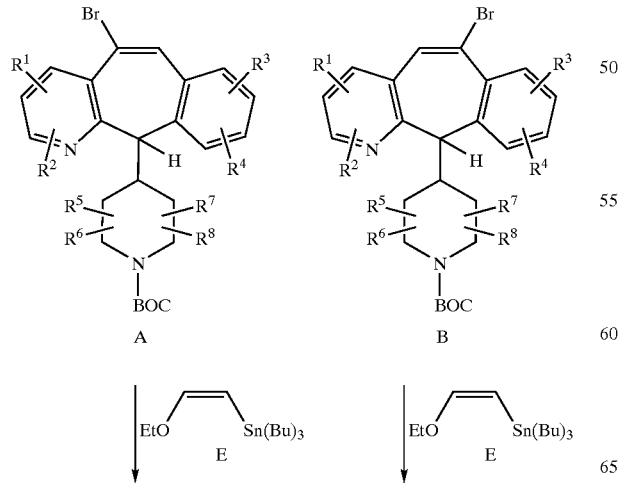

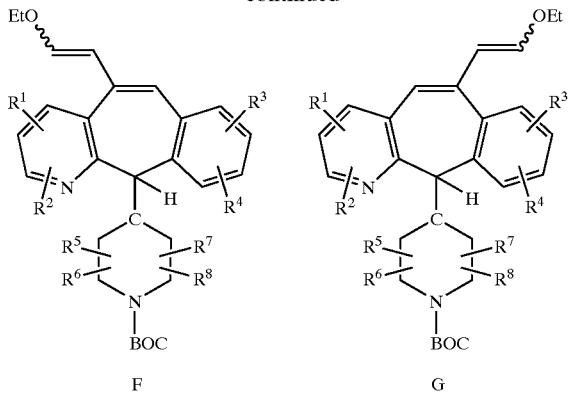

Alternatively, Intermediates A and B can be reacted with tin vinylether E, in the presence of PdCl₂, as described in Tetrahedron, (1991), 47, 1877, to yield vinylethers F and G (Scheme 15a). Allowing F and G to stand until aldehyde is visible by NMR (at least two weeks) and then reacting with Hg(OAc)₂, KI followed by NaBH₄, as described in J. Chem. Soc., Perkin Trans., (1984), 1069 and Tet. Lett., (1988), 6331, yields mixtures H, I and J, K. Intermediates H and J are separated and reacted as are intermediates K and L in the general scheme for one methylene piperazines to yield compounds of Formula 1.0, of this invention.

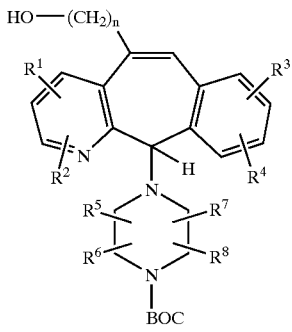

H, n = 1
I, n = 2

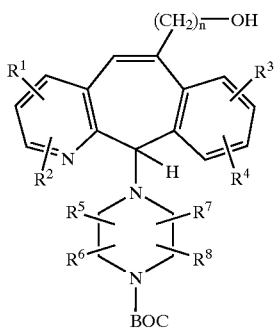

J, n = 1
K, n = 2

Scheme 16: Branching on the methylene chain
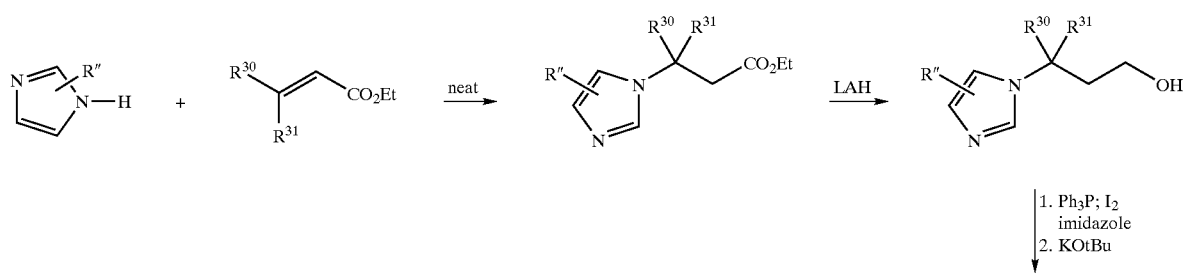
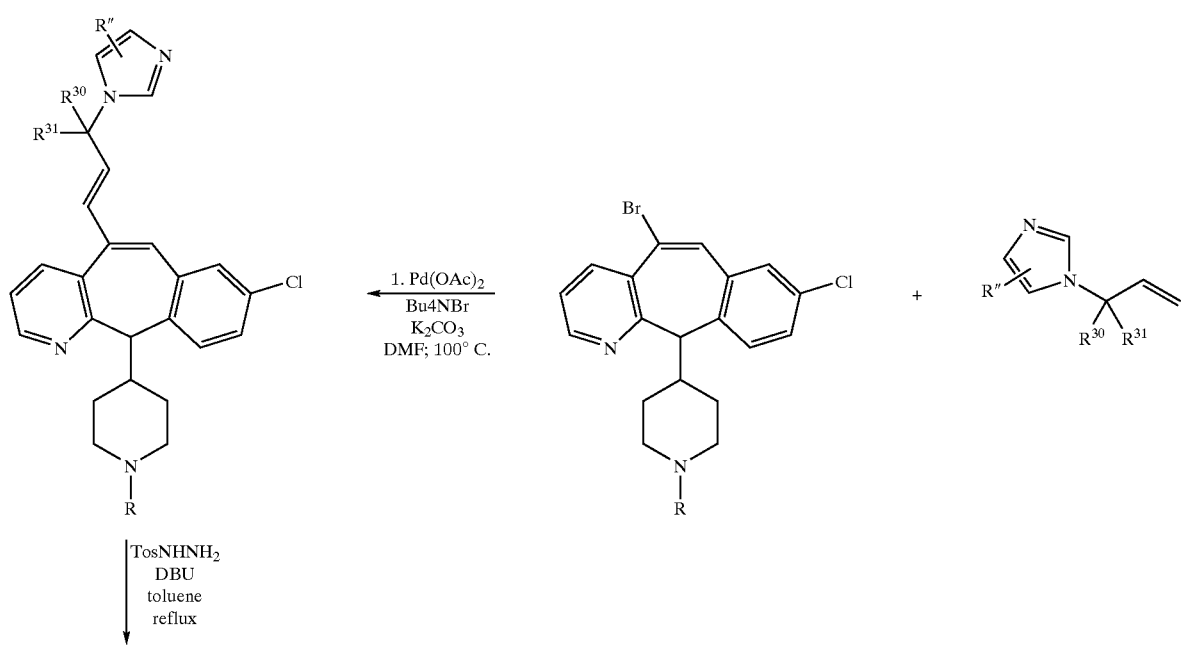
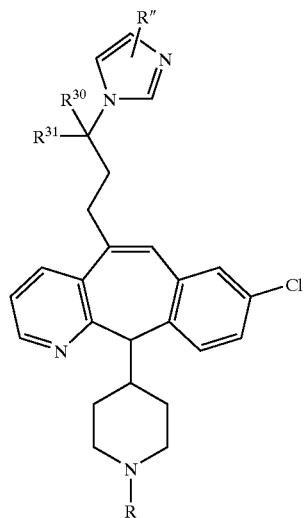

Compounds with substitution along the chain can be synthesized starting with a substituted ethyl acrylate derivative. Addition of imidazole across the olefin followed by reduction gives the terminal alkene, which can be added to the appropriately substituted vinyl bromide under Heck reaction conditions. Selective reduction of the di-substituted olefin gives the saturated derivative (Scheme 16).

Scheme 17: C-linked imidazoles

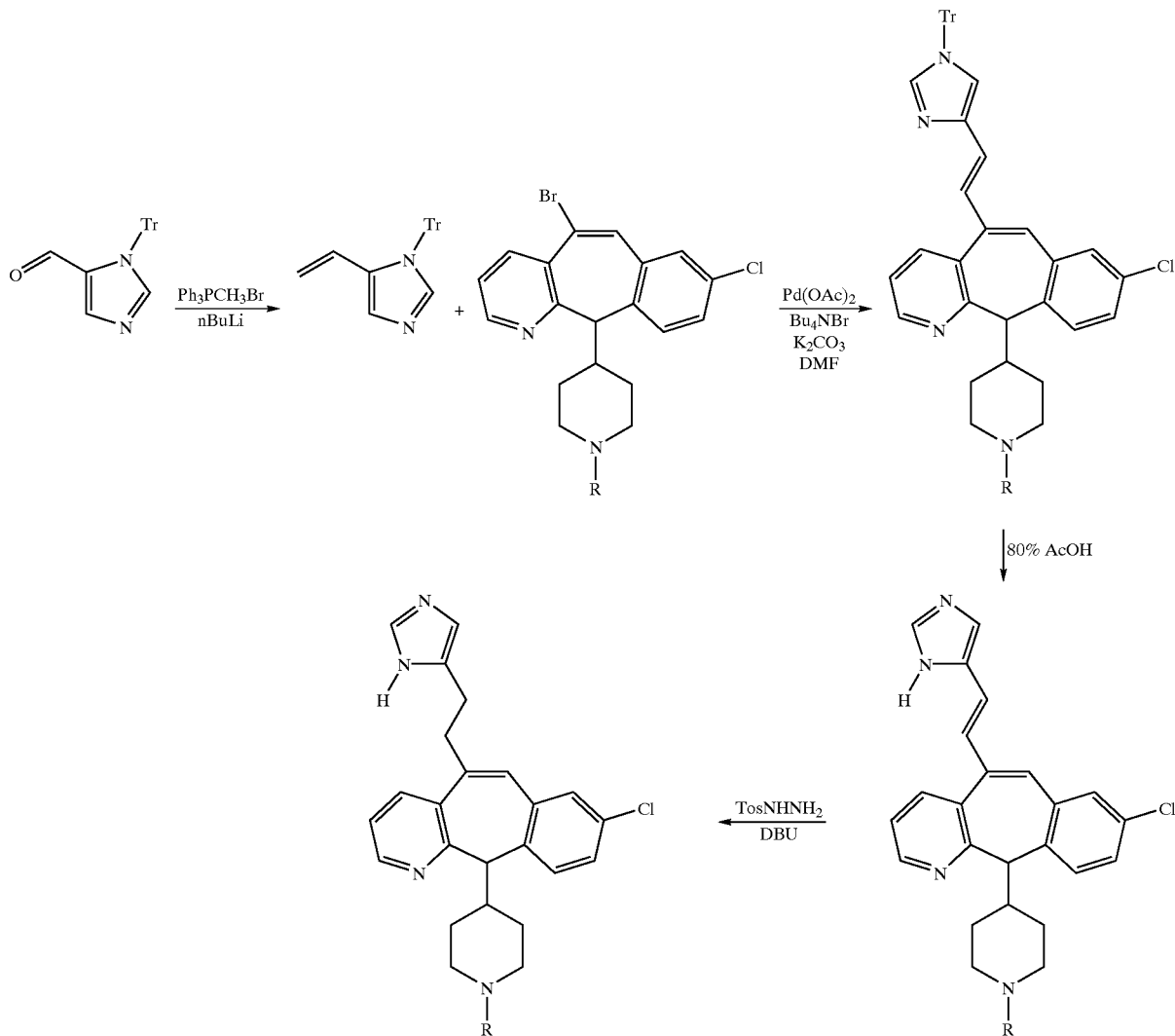

The synthesis of the C-linked imidazoles proceeds through the Heck reaction of the appropriately substituted vinyl imidazole with the appropriate vinyl bromide. Selective reduction of the resulting di-substituted olefin gives the target compound. A similar procedure can be carried out with differentially N-substituted imidazoles to give N-alkyl imidazole derivatives (Scheme 17).

Suberyl Compounds

One skilled in the art will appreciate that the compounds of the invention represented by Formula 1.0, wherein a, b, c or d is C can be prepared according to the following schemes:

Scheme 18: Preparation of suberyl analogues
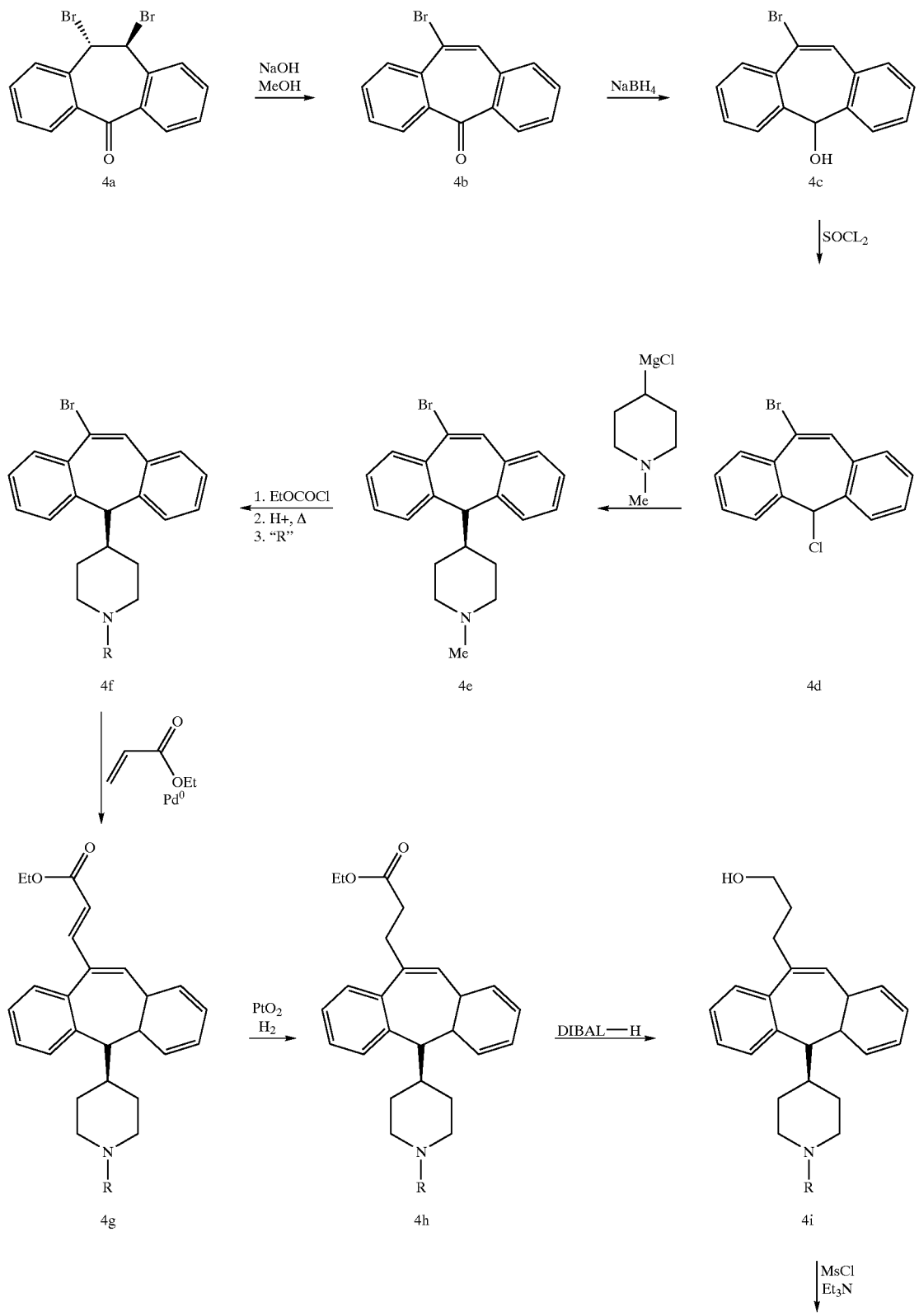

-continued

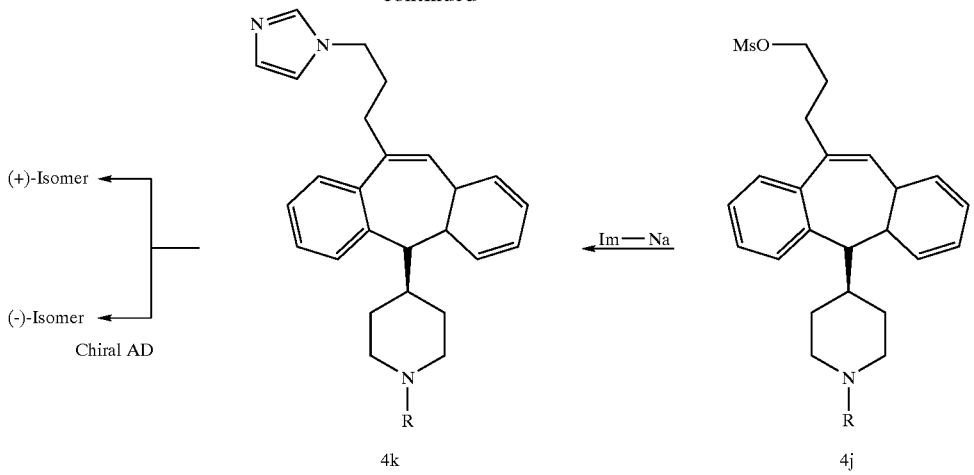

Tricyclic vinyl bromide azaketone 4b was prepared as described by Rupard et. al. (*J. Med. Chem.* 1989, 32, 2261–2268). Reduction of ketone to alcohol 4c was carried out with NaBH$_4$. The alcohol was converted to chloride 4d and then treated with N-methylpiperidine Grignard reagent to give piperidine derivative 4e. Demethylation was effected with ethyl chloroformate followed by acid hydrolysis and subsequent derivitization (i.e sulfonylation, acylation and carbomylation etc.). Preparation of compounds with 3-carbon substituted imidazole moieties on the suberane trycyclic bridgehead was carried out in a similar way as described in scheme 3.

For example, the compound referred to herein as SCH413592

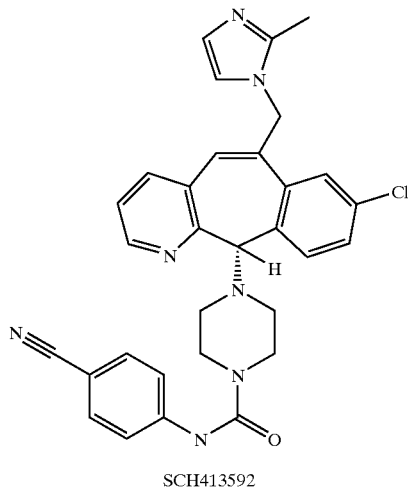

SCH413592

A. Preparation of Compound (233)

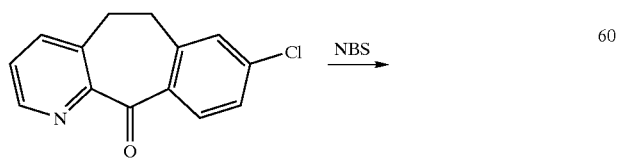

-continued

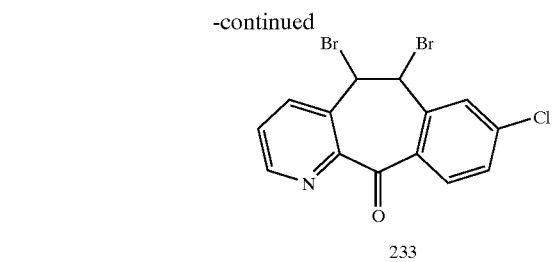

233

The tricyclic keto-compound (disclosed in U.S. Pat. No. 5,151,423) (30.0 g; 123.2 mmol) was combined with NBS (48.2 g; 271.0 mmol) and benzoyl peroxide (0.42 g) in CCl$_4$ (210 ml). The reaction was heated to 80° C. for 10 hr. The mixture was cooled and let stand for 8 hr. The resulting precipitate was filtered. Added MeOH (200 ml) and stirred the mixture over 2 days. The solid was filtered and dried under vacuum to a constant weight.

B. Preparation of Compounds (234a) and (234b)

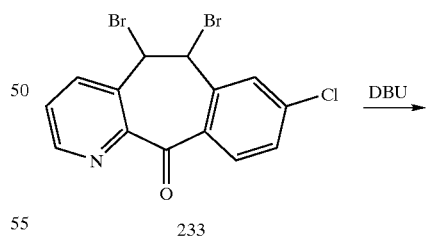

233

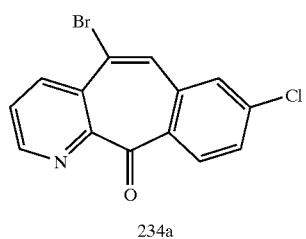

234a

-continued

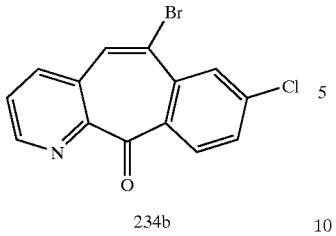

234b

The dibromo compound (233) from Step A (35.72 g; 88.97 mmol) above was dissolved in $CH_2Cl_2$ (1.5 L) and cooled to 0° C. Dropwise, DBU (15.96 ml) was added and the suspension stirred for 3 hr. The reaction mixture was concentrated redissolved in $CH_2Cl_2$ (1.5 L) filtered through a bed of silica gel and rinsed with 5% $EtOAc/CH_2Cl_2$ (4 L). The combined rinses were concentrated and purified by flash silica gel column chromatography into pure 5 and 6 monobromo substituted compounds eluting with 10–30% EtOAc/Hex then 3% $EtOAc/CH_2Cl_2$.

C. Preparation of Compound (235)

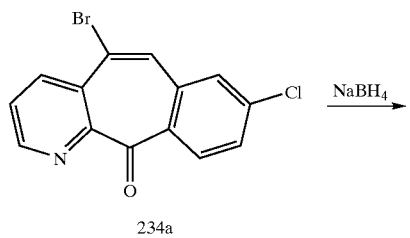

234a

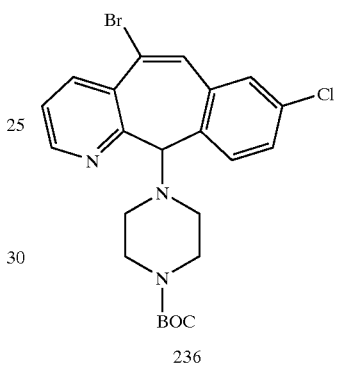

235

The 5-bromo substituted compound (234a) from Step B above (4.0 g; 12.45 mmol) was taken up in MeOH and cooled to 0° C. $NaBH_4$ (916.4 mg; 24.2 mmol) was added and the reaction mixture stirred for 5.5 hr. The solvent was removed and the resulting residue was used directly.

Step D Preparation of Compound (236)

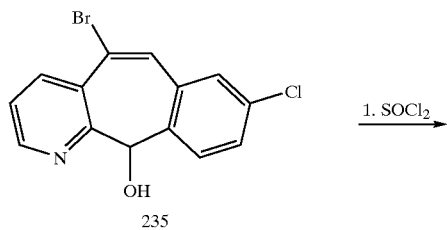

235

-continued

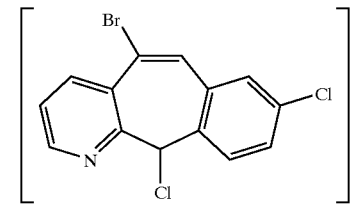

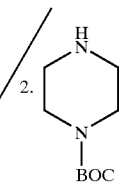

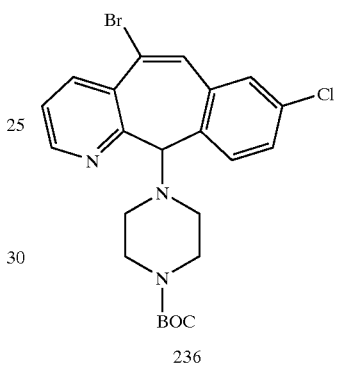

236

The alcohol compound (235) from Step C above (3.98 g; 12 mmol) was dissolved in $CH_2Cl_2$ cooled to 0° C. and treated with 2,6-Lutidine (5.73 ml; 49 mmol). $SOCl_2$ (1.8 ml; 24.6 mmol) was added and the reaction was allowed to stir and come to room temperature over 3 hr. The reaction mixture was poured into 0.5 N NaOH (80 ml) extracted and concentrated in vacuo. The crude product was taken up in $CH_3CN$ and treated with 1,2,2,6,6-Pentamethylpiperidine (4.45 ml; 24.6 mmol) (Aldrich). The reaction was heated to 60–65° C. treated with tert-butyl 1-piperazinecarboxylate (2.32 g; 12 mmol) (Aldrich) and stirred over night under $N_2$ atmosphere. The reaction mixture was concentrated to dryness, redissolved in $CH_2Cl_2$ and washed with sat. aqueous $NaCO_3$. The organic layer was dried over $Na_2SO_4$, filtered and purified by flash silica gel column chromatography eluting with 1:4–1:2 EtOAc/Hexanes to afford the product as a white solid.

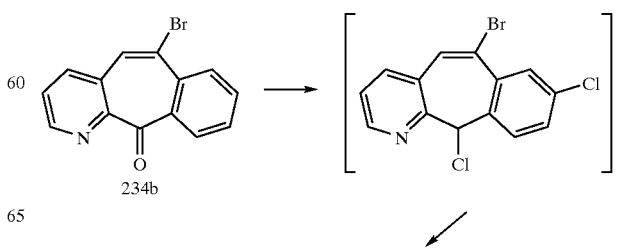

234b

-continued

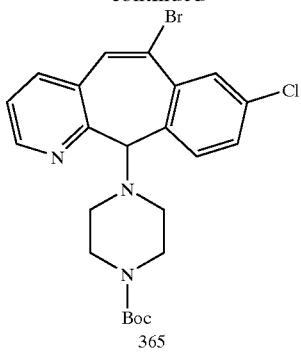
365

In essentially the same manner as in Preparative Example 23, Steps A–D, using the 6-Bromo substituted product from Step B, Compound (234b), the product Compound (365) was prepared (76.6 g, 100% yield).

PREPARATIVE EXAMPLE 42
A. Preparation of Compound (366)

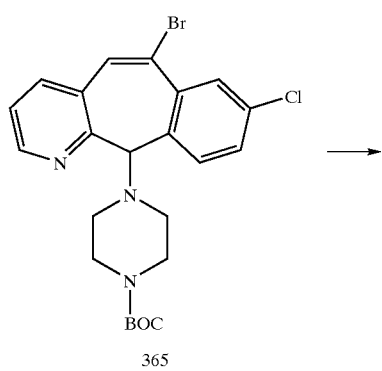
365

366

To a solution of Compound (365) from Preparative Example 41 (4.0 g, 8.16 mmol) in toluene (75 mL) and MeOH (20 mL), was added triphenyl phosphine (1.099 g, 4.08 mmol), DBU (1.7 g, 11.02 mmol) and palladium chloride (0.145 g, 0.82 mmol). The resulting solution was evacuated with CO at 100 psi and heated at 78° C.–82° C. for 5 hours, followed by the extraction with EtOAc—H₂O. The combined organic layer was then washed with brine, dried over Na₂SO4, concentrated to dryness and purified by column chromatography, eluting with 30% EtOAc/70% Hexane to give a Compound (366) (3.12 g, 100% yield, MH$^+$=470.1).

B. Preparation of Compound (367)

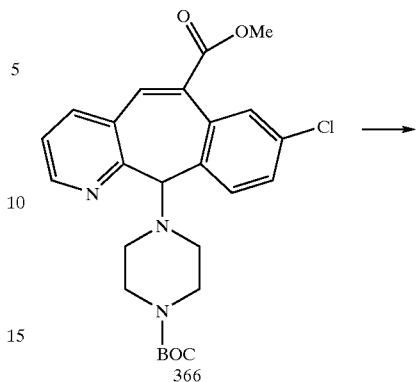
366

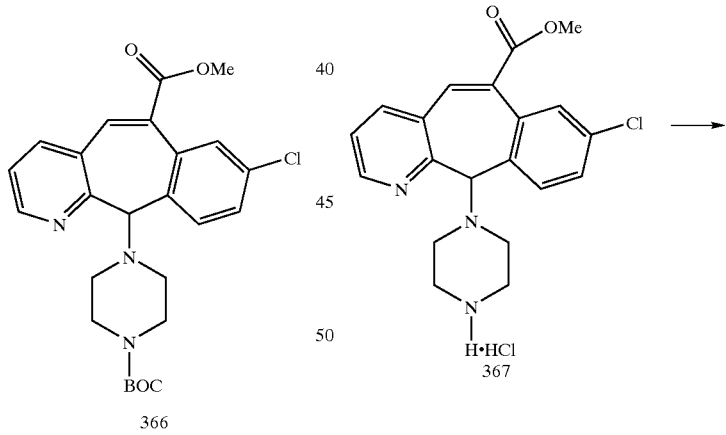
367

A solution of Compound (366) from Step A above (3.1 g, 6.6 mmol) in 4M HCl/Dioxane (120 mL) was stirred for 3 hours and then concentrated to dryness to give the crude salt of Compound (367) (3.89 g, 100% yield, MH$^+$=370.2)

C. Preparation of Compound (368)

367

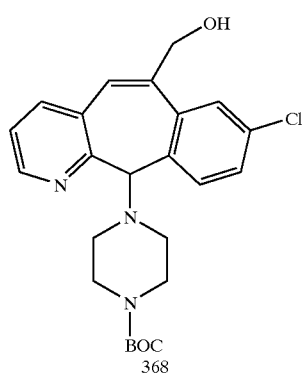
368

To a solution of Compound (367) from Step B above (3.43 g, 8.45 mmol) in THF (60 mL) at 0° C., was added DIBAL (7.21 g, 50.7 mmol). The resulting solution was warmed to room temperature, stirred overnight and then concentrated to dryness, followed by the addition of Boc anhydride (3.69 g, 16.9 mmol). The reaction was then extracted with CH$_2$Cl$_2$—H$_2$O, filtered over Na$_2$SO$_4$ and concentrated to dryness to afford Compound (368) (3.75 g, 100% yield, MH$^+$=442.4).

C.1 Alternate Preparation of Compound (368)

A solution of compound 366 from step A above (23.46 g, 50.98 mmol) in CH$_2$Cl$_2$—MeOH—H$_2$O (120 mL, 600 mL, 60 mL respectively) combined with LiOH (12.0 g, 350.88 mmol) was refluxed at 40° C. overnight. Solvent was removed from the reaction mixture and the residue diluted with CH$_2$Cl$_2$, was acidified to pH 6 with 1N HCl. The organic layer was separated and washed with water, dried over Na$_2$SO$_4$ and concentrated. The product was dissolved in THF (285 mL) at 0° C. Triethyl amine (6 mL, 42.97 mmol) and ethyl chloroformate (4.1 mL, 42.97 mmol) were added and stirred at 0° C. for 1 h. The reaction mixture was filtered and the filtrate was cooled to −70° C. To this filtrate was added NaBH$_4$ (3.97 g, 104.94 mmol) and stirred for 1 h at −70° C. after which time 40 mL of MeOH was added dropwise. The solvents were removed and the residue taken up in methylene chloride, washed with sat. (aq) NaHCO$_3$, then brine, dried over Na$_2$SO$_4$ and concentrated to give Compound (368) as a solid.

D. Preparation of Compound (369)

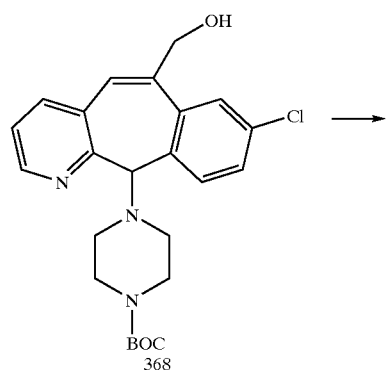
368

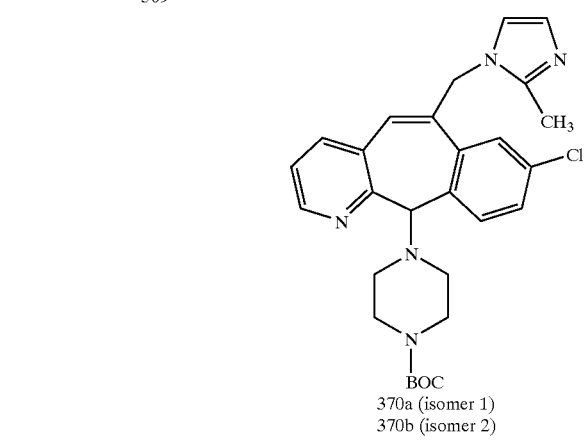
369

To a solution of Compound (368) from Step C above (3.74 g, 8.46 mmol) in CH$_2$Cl$_2$ (100 mL) was added triethyl amine (3.5 mL, 25.38 mmol) and methanesulfonyl chloride (1.45 g, 2.7 mmol). The resulting solution was stirred under nitrogen at room temperature for overnight and then washed with saturated NaHCO$_3$, then brine, and dried over Na$_2$SO$_4$ to give the mesylate compound (369) (3.86 g, 88% yield).

E. Preparation of Compounds (370a) and (370b)

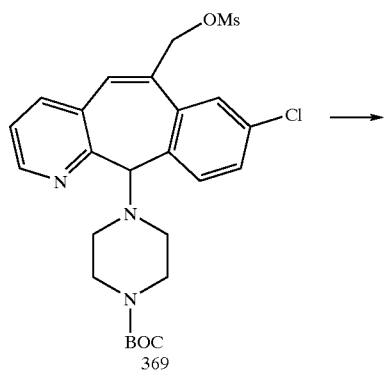
369

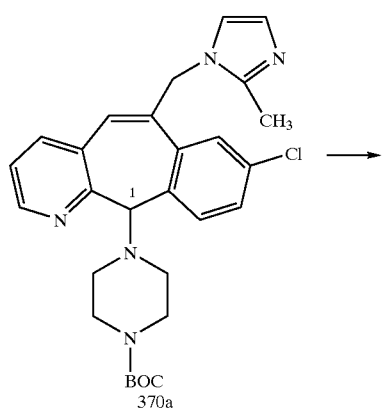
BOC
370a (isomer 1)
370b (isomer 2)

To a solution of 2-methylimidazole (2.43 g, 29.68 mmol) in DMF (30 mL) under N$_2$ was added NaH (0.53 g, 22.3 mmol) and stirred for 10 min, followed by the addition of Compound (369) from Step D above (3.86 g, 7.42 mmol). The solution was stirred over night. The solution was then concentrated to dryness and extracted with EtOAc—NaHCO$_3$, dried over Na$_2$SO$_4$, and concentrated. The crude product was purified by column chromatography, eluting with 2% MeOH—NH$_3$/98% CH$_2$Cl$_2$ to afford a mixture of isomers. Further separation was accomplished by Preparative HPLC Chiral AD Column chromatography, eluting with 25% IPA/75% hexane/0.2% DEA to give pure Compound (370a) (isomer 1) (0.160 g) and Compound (370b) (isomer 2) (0.140 g) (MH$^+$=506.1)

F. Preparation of Compounds (371a) and (371b)

370a

103
-continued

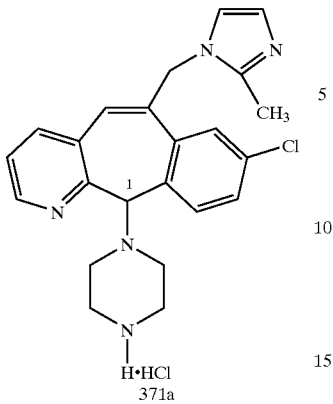

371a

A solution of Compound (370a) (isomer 1) from Step E above (0.105 g, 0.21 mmol) in 4M HCl/Dioxane (10 mL) was stirred at room temperature for 3 hours and concentrated to dryness to afford Compound (371a) (0.147 g, 100% yield)

Compound (370b) (isomer 2) from Step E was treated in the same manner as isomer 1 above, to afford Compound (371b) (isomer 2).

EXAMPLE 167

Preparation of Compound (372)

To a solution of compound 371a (1.3 g, 2.94 mmol) in CH$_2$Cl$_2$ (60 mL) was added triethyl amine (1.3 mL, 9.4 mmol) and p-cyano phenyl isocyanate (0.466 g, 3.24 mmol). The resulting solution was stirred at room temperature overnight, followed by the extraction with CH$_2$Cl$_2$ and saturated NaHCO$_3$ The organic layer was dried over Na$_2$SO$_4$, evaporated and the residue purified by column chromatography, eluting with 1% –2% MeOH—NH$_3$/98% CH$_2$Cl$_2$ to afford compound (372) (0.870 g , 48% yield) see table below.

Preferred P-gp Inhibitors are Selected from

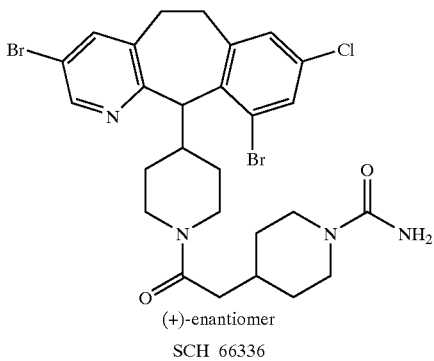

(+)-enantiomer
SCH 66336

104
and the compounds of Formula I:

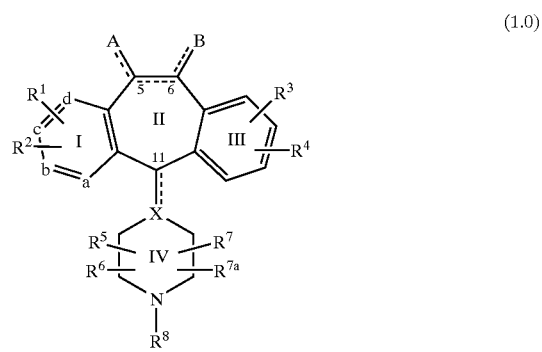

(1.0)

or a pharmaceutically acceptable salt or solvate thereof, wherein:
  one of a, b, c and d represents N or N$^+$O$^-$, and the remaining a, b, c, and d groups represent C, wherein each carbon has an R$^1$ or R$^2$ group bound to said carbon; or
  each of a, b, c, and d are C, wherein each carbon has an R$^1$ or R$^2$ group bound to said carbon;
  The dotted lines ( - - - ) represent optional bonds;
  X represents N or CH when the optional bond is absent, and represents C when the optional bond is present;
  When the optional bond is present between carbon atom 5 and carbon atom 6 then there is only one A substituent bound to carbon atom 5 and there is only one B substituent bound to carbon atom 6 and A or B is other than H;
  When the optional bond is not present between carbon atom 5 and carbon atom 6 single bond, then there are two A substituents bound to carbon atom 5, wherein each A substituent is independently selected and two B substituents bound to carbon atom 6, wherein each B substituent is independently selected;
  A and B are independently selected from:
  (1) —H;
  (2) —R$^9$;
  (3) —R$^9$—C(O)—R$^9$;
  (4) —R$^9$—CO$_2$—R$^{9a}$;
  (5) —(CH$_2$)pR$^{26}$;
  (6) —C(O)N(R$^9$)$_2$, wherein each R$^9$ is the same or different;
  (7) —C(O)NHR$^9$;
  (8) —C(O)NH—CH$_2$—C(O)—NH$_2$;
  (9) —C(O)NHR$^{26}$;
  (10) —(CH$_2$)pC(R$^9$)—O—R$^{9a}$;
  (11) —(CH$_2$)p(R$^9$)$_2$, wherein each R$^9$ is the same or different;
  (12) —(CH$_2$)pC(O)R$^9$;
  (13) —(CH$_2$)pC(O)R$^{27a}$;
  (14) —(CH$_2$)pC(O)N(R$^9$)$_2$, wherein each R$^9$ is the same or different;
  (15) —(CH$_2$)pC(O)NH(R$^9$);
  (16) —(CH$_2$)pC(O)N(R$^{26}$)$_2$, wherein each R$^{26}$ is the same or different;
  (17) —(CH$_2$)pN(R$^9$)—R$^{9a}$, (e.g. —CH$_2$—N(CH2-pyridine)-CH$_2$-imidazole);
  (18) —(CH$_2$)pN(R$^{26}$)$_2$, wherein R$^{26}$ is the same or different (e.g., —(CH$_2$)p—NH—CH$_2$—CH$_3$);
  (19) —(CH$_2$)pNHC(O)R$^{50}$;
  (20) —(CH$_2$)pNHC(O)$_2$R$^{50}$;
  (21) —(CH$_2$)pN(C(O)R$^{27a}$)$_2$ wherein each R$^{27a}$ is the same or different;

(22) —(CH$_2$)pNR$^{51}$C(O)R$^{27}$, optionally, R$^{51}$ and R$^{27}$, taken together with the atoms to which they are bound, form a heterocycloalkyl ring consisting of, 5 or 6 members, provided that when R$^{51}$ and R$^{27}$ form a ring, R$^{51}$ is not H;

(23) —(CH$_2$)pNR$^{51}$C(O)NR$^{27}$, optionally, R$^{51}$ and R$^{27}$, taken together with the atoms to which they are bound, form a heterocycloalkyl ring consisting or 5 or 6 members, provided that when R$^{51}$ and R$^{27}$ form a ring, R$^{51}$ is not H;

(24) —(CH$_2$)pNR$^{51}$C(O)N(R$^{27a}$)$_2$, wherein each R$^{27a}$ is the same or different;

(25) —(CH$_2$)pNHSO$_2$N(R$^{51}$)$_2$, wherein each R$^{51}$ is the same or different;

(26) —(CH$_2$)pNHCO$_2$R$^{50}$;

(27) —(CH$_2$)pNC(O)NHR$^{51}$;

(28) —(CH$_2$)pCO$_2$R$^{51}$;

(29) —NHR$^9$, (30)

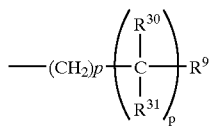

wherein R$^{30}$ and R$^{31}$ are the same or different;

(31)

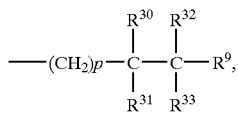

wherein R$^{30}$, R$^{31}$, R$^{32}$ and R$^{33}$ are the same or different;

(32) -alkenyl-CO$_2$R$^{9a}$;
(33) -alkenyl-C(O)R$^{9a}$;
(34) -alkenyl-CO$_2$R$^{51}$;
(35) -alkenyl-C(O)—R$^{27a}$;
(36) (CH$_2$)p-alkenyl-CO$_2$—R$^{51}$;
(37) —(CH$_2$)pC=NOR$^{51}$or
(38) —(CH$_2$)p-Phthalimid;

p is 0, 1, 2, 3 or 4;

Each R$^1$ and R$^2$ is independently selected from H, Halo, —CF$_3$,

—OR$^{10}$, COR$^{10}$, —SR$^{10}$, —S(O)$_t$R$^{15}$ (wherein t is 0, 1 or 2, —N(R$^{10}$)$_2$, —NO$_2$, —OC(O)R$^{10}$, CO$_2$R$^{10}$, —OCO$_2$R$^{15}$, —CN, —NR$^{10}$COOR$^{15}$, —SR$^{15}$C(O)OR$^{15}$, —SR$^{15}$N(R$^{13}$)$_2$ (provided that R$^{15}$ in —SR$^{15}$N(R$^{13}$)$_2$ is not —CH$_2$) wherein each R$^{13}$ is independently selected from H or —C(O)OR$^{15}$, benzotriazol-1-yloxy, tetrazol-5-ylthio, or substituted tetrazol-5-ylthio, alkynyl, alkenyl or alkyl, said alkyl or alkenyl group optionally being substituted with halo, —OR$^{10}$ or —CO$_2$R$^{10}$;

R$^3$ and R$^4$ are the same or different and each independently represents H, any of the substituents of R$^1$ and R$^2$;

R$^5$, R$^6$, R$^7$ and R$^{7a}$ each independently represents H, —CF$_3$,

—COR$^{10}$, alkyl or aryl, said alkyl or aryl optionally being substituted with —OR$^{10}$, —SR$^{10}$, —S(O)$_t$R$^{15}$, —NR$^{10}$COOR$^{15}$, —N(R$^{10}$)$_2$, —NO$_2$, —C(O)R$^{10}$, —OCOR$^{10}$, —OCO$_2$R$^{15}$, —CO$_2$R$^{10}$, OPO$_3$R$^{10}$, or R$^5$ is combined with R$^6$ to represent =O or =S;

R$^8$ is selected from:

H, (2.0)

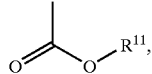

(3.0)

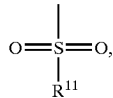

(4.0)

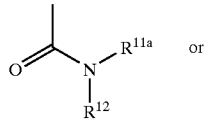 or (5.0)

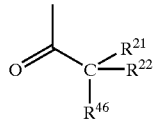

R$^9$ is selected from:
(1) heteroaryl;
(2) substituted heteroaryl;
(3) arylalkoxy;
(4) substituted arylalkoxy;
(5) heterocycloalkyl;
(6) substituted heterocycloalkyl;
(7) heterocycloalkylalkyl;
(8) substituted heterocycloalkylalkyl;
(9) heteroarylalkyl;
(10) substituted heteroarylalkyl;
(11) heteroarylalkenyl;
(12) substituted heteroarylalkenyl;
(13) heteroarylalkynyl or
(14) substituted heteroarylalkynyl;

wherein said substituted R$^9$ groups are substituted with one or more (e.g. 1, 2 or 3) substituents selected from:
(1) —OH;
(2) —CO$_2$R$^{14}$;
(3) —CH$_2$OR$^{14}$,
(4) halo (e.g. Br, Cl or F),
(5) alkyl (e.g. methyl, ethyl, propyl, butyl or t-butyl);
(6) amino;
(7) trityl;
(8) heterocycloalkyl;
(9) cycloalkyl, (e.g. cyclopropyl or cyclohexyl);
(10) arylalkyl;
(11) heteroaryl;
(12) heteroarylalkyl or
(13)

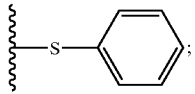

wherein R$^{14}$ is independently selected from: H; alkyl; aryl, arylalkyl, heteroaryl or heteroarylalkyl;

R$^{9a}$ is selected from: alky or arylalkyl;

R$^{10}$ is selected from: H; alkyl; aryl or arylalkyl;

$R^{11}$ is selected from:
(1) alkyl;
(2) substituted alkyl;
(3) aryl;
(4) substituted aryl;
(5) cycloalkyl;
(6) substituted cycloalkyl;
(7) heteroaryl;
(8) substituted heteroaryl;
(9) heterocycloalkyl; or
(10) substituted heterocycloalkyl;
wherein said substituted $R^{11}$ groups have 1, 2 or 3, substituents selected from:
(1) —OH;
(2) halo or
(3) alkyl;

$R^{11a}$ is selected from:
(1) H;
(2) OH;
(3) alkyl;
(4) substituted alkyl;
(5) aryl;
(6) substituted aryl;
(7) cycloalkyl;
(8) substituted cycloalkyl;
(9) heteroaryl;
(10) substituted heteroaryl;
(11) heterocycloalkyl; or
(12) substituted heterocycloalkyl;
wherein said substituted $R^{11a}$ groups have 1, 2 or 3, substituents selected from:
(1) —OH;
(2) —CN;
(3) —CF$_3$;
(4) halo;
(5) alkyl;
(6) cycloalkyl;
(7) heterocycloalkyl;
(8) arylalkyl;
(9) heteroarylalkyl;
(10) alkenyl or
(11) heteroalkenyl;

$R^{12}$ is selected from: H, or alkyl;

$R^{15}$ is selected from: alkyl or aryl;

$R^{21}$, $R^{22}$ and $R^{46}$ are independently selected from:
(1) —H;
(2) alkyl;
(3) aryl;
(4) substituted aryl,
 optionally substituted with one or more substituents selected from: alkyl, halo, CF3 or OH;
(5) cycloalkyl;
(6) substituted cycloalkyl;
 optionally substituted with one or more substituents selected from: alkyl, halo, CF3 or OH;
(7) heteroaryl of the formula,

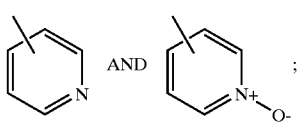
AND (9) heterocycloalkyl of the formula:

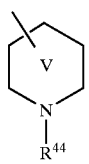

wherein $R^{44}$ is selected from:
(1) —H;
(2) alkyl;
(3) alkylcarbonyl;
(4) alkyloxy carbonyl;
(5) haloalkyl or
(6) —C(O)NH($R^{51}$);

when $R^{21}$, $R^{22}$ or $R^{46}$ is the heterocycloalkyl of the formula above (i.e. Ring V), Ring V includes:

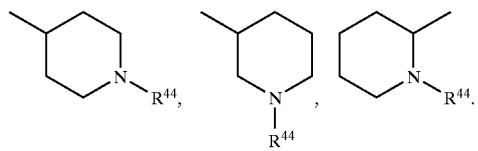

Examples of Ring V include:

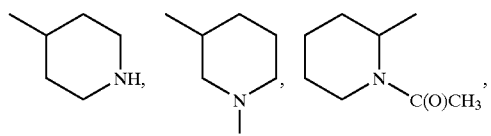

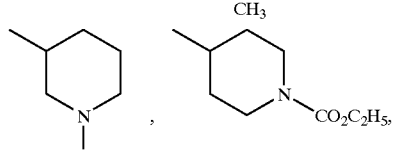

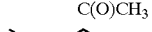

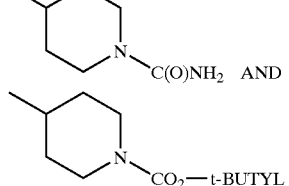

$R^{26}$ is independently selected from:
(1) —H;
(2) alkyl;
(3) alkoxyl;
(4) —CH$_2$—CN;
(5) $R^9$;
(6) —CH$_2$CO$_2$H;
(7) —C(O)alkyl or
(8) CH$_2$CO$_2$alkyl;

$R^{27}$ is independently selected from:
(1) —H;
(2) —OH;
(3) alkyl or
(4) alkoxy;

$R^{27a}$ is independently selected from:
(1) alkyl or
(2) alkoxy;

$R^{30}$ through $R^{33}$ is independently selected from:
(1) —H;
(2) —OH;
(3) =O;
(4) alkyl;
(5) aryl or
(6) arylalkyl;

$R^{50}$ is independently selected from:
(1) alkyl;
(2) heteroaryl;
(3) substituted heteroaryl or
(4) amino;

wherein said substituents on said substituted $R^{50}$ groups are independently selected from: alkyl; halo; or —OH;

$R^{50a}$ is independently selected from:
(1) heteroaryl;
(2) substituted heteroaryl or
(3) amino;

$R^{51}$ is selected from: —H, or alkyl.

More preferred compounds are selected from:

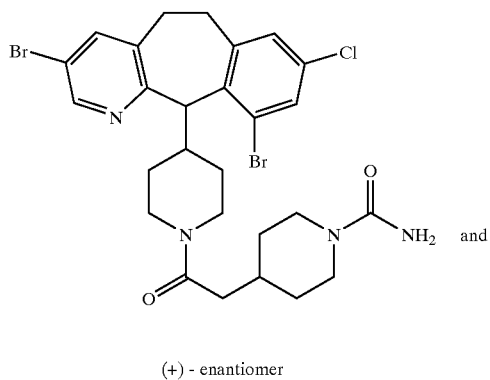

(+) - enantiomer
SCH66336

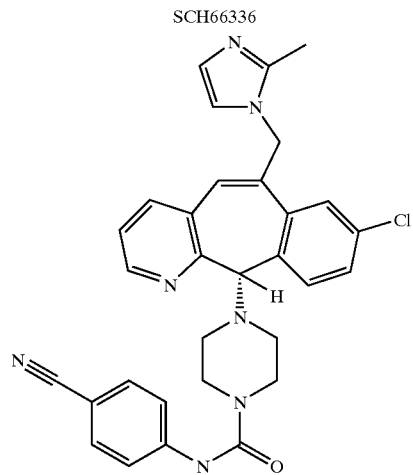

SCH413592 and

Most preferred is:

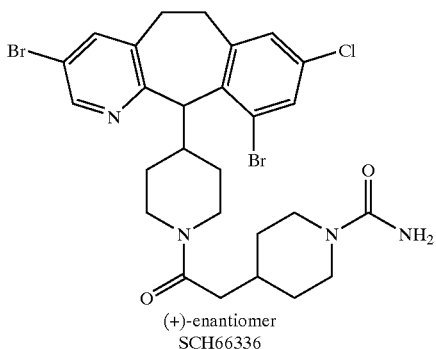

(+)-enantiomer
SCH66336

EXAMPLES

The examples set forth below characterize the effects of the following P-gp inhibitory compound (referred herein to as SCH66336 in the Tables below):

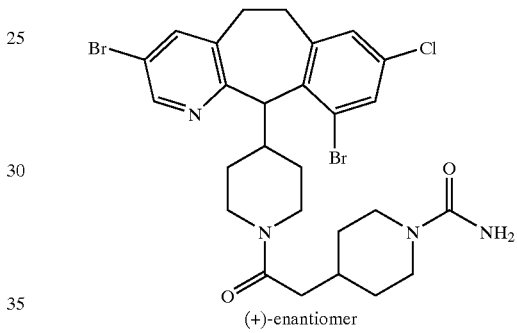

(+)-enantiomer on the P-gp transporter enzyme.

The first Example employed viable transformed cells with an overabundance of P-gp in the membrane. These cells were exposed to SCH66336 over a range of concentrations in order to analyze quantitatively the impedence of transport of a known P-gp substrate. The relationship of the known P-gp substrate's retention to SCH66336 concentration was then mathematically analyzed to determine a half-maximal interaction constant ($IC_{50}$~3 $\mu M$). Comparing this result with those of known positive controls directly demonstrated that SCH66336 impedes the function of the P-gp transporter.

The second Example monitored the consumption of ATP, a high-energy biological energy source required for transporter enzyme function. ATP is converted to two other chemicals—ADP and inorganic phosphate—during the P-gp mediated transport porcess. Therefore, through analysis of the rate of phosphate release at various concentrations of SCH66336, the normalized half-maximal concentrations for the interaction could be determined (Km~3 $\mu M$).

The data presented below surprisingly demonstrate dramatic inhibition of P-gp transport by SCH66336 in a concentration-dependent manner, with an $IC_{50}$ of <3 M (See Example A and FIG. 1). In addition, ATP hydrolysis kinetics show that SCH66336 is a very slow substrate of P-gp (See Example B and FIG. 2). Unlike most P-gp antagonists, which result in increased ATP consumption, SCH66336 has the rare ability to cause decreases in ATP consumption. Since ATP is consumed at a purported rate of about 1 per transport event, the hydrolysis of ATP represents transport function turnover rate or activity assay (Eytan et al., 1996;

Ambudkar et al 1997; Stein 1997; Shapiro et al, 1998). A decrease of consumption suggests that the inhibitor should have a prolonged residence inside the cell, rendering it superior in duration and effect over known P-gp antagonists.

Daunorubicin (DNR), verapamil, colchicine, cyclosporin A, mannitol, dithiothreitol, ATP disodium, ammonium molybdate, ascorbic acid, sodium meta-arsenite, aprotinin, leupeptin, EGTA, EDTA, HEPES, ouabain, phenylmethylsulfonyl fluoride, and TRIZMA base were purchased from Sigma Chemical Co. (St. Louis, Mo.). Hanks' balanced salt solution, Alpha Minimum Essential Medium, DMEM, penicillin/streptomycin, fetal bovine serum (FBS), and trypsin-EDTA were obtained from Life Technologies, Inc. (Rockville, Md.). Sodium orthovanadate was purchased from Pfaltz & Bauer Inc. (Waterbury, Conn.). Microplates (Costar 96-well), plastic tubes, and cell culture flasks (75 cm$^2$) were purchased from Corning Inc. (Corning, N.Y.). All other reagents were of the highest grade commercially available.

Example A

SCH66336 Effectively Inhibits the P-gp-Mediated Transport of Daunorubicin (DNR) and Rhodamine 123 (Rho)

CR1R12 cell line, provided by Dr. Alan Senior (Univ. of Rochester), was maintained in complete α-minimum essential medium (α-MEM) supplemented with 10% FBS, penicillin/streptomycin (50 units/50 µg/ml) in a 5% $CO_2$-95% air atmosphere at 37° C. Colchicine (0.5 µg/ml) was added to the culture medium. Cells were grown to 80–90% confluency and treated with trypsin-EDTA before subculturing. The NIH 3T3 G185 cell line presenting the gene product of human MDR1 was licensed from NIH and maintained in DMEM.

Fluorescence measurements of individual cells were performed using a Becton-Dickinson FACScalibur fluorescence-activated cell sorter (San Jose, Calif.), equipped with an ultraviolet argon laser (excitation at 488 nm, emission at 530/30 and 570/30 nm band-pass filters). Analysis was gated to include single cells on the basis of forward and side light-scatter and was based on acquisition of data from 10,000 cells. Log fluorescence was collected and displayed as single-parameter histograms. A direct functional assay for the P-gp efflux pump in CR1R12 cells was performed with the flow cytometer (Wang et al., 2000).

Cell viability was assessed using exclusion of 0.4% trypan blue as well as propidium iodide staining. Dead cells in which propidium iodide was bound to double strands of DNA or RNA were detected in certain regions of the cytometry dot plots and not included in the final data calculations.

The DNR fluorescence intensity of individual cells was recorded as histograms. The mean fluorescence intensity of 10,000 cells was used for comparison among different conditions. Vanadate was selected as a positive control to normalize the measurements because it can maximally inactivate the P-gp efflux pump. Relative fluorescence was used for quantitation and comparison among different compounds. The relative fluorescence (% inactivation) represents a ratio obtained through the following formula: the geometric mean fluorescence of a discrete sample divided by the geometric mean fluorescence in the presence of 5 mM vanadate, times 100, or expressed as $$\text{Relative fluorescence} = \frac{\text{Fluorescence of sample geometric mean}}{\text{Fluorescence of reference std. Geometric mean}} \times 100$$

Results

As fluorescent substrates transported by P-gp, daunorubicin (DNR) and rhodamine 123 (Rho) serve as markers for active transport function simply by measurement of fluorescence per cell (Wang et al., 2000). The farnesyl protein transferase inhibitor SCH 66336 effectively inhibited the P-gp-mediated transport of DNR and Rho. The $IC_{50}$ (concentration at half-maximum inhibition) can be determined from a simple function, as shown in FIG. 1, where the retained fluorescence is measured for samples of viable cells by a flow cytometer at varying concentrations of SCH66336. The concentration dependency of inhibition displayed a sigmoidal response curve (FIG. 1a), a consequence of cooperativity, with the Hill equation for allosteric interaction enzymes therefore being the appropriate function for fitting to the data: $v = V_{max} S^n / (K' + S^n)$. The $IC_{50}$ of DNR transport in the CR1R12 cell line is ≈9 µM, and SCH66336 can achieve an extent of inhibition exceeding that of verapamil. As shown in FIG. 1b, the $IC_{50}$ for SCH66336 in the G185 cells (which express the gene product of human MDR1) is ≈3 µM, which is three times as potent as the inhibition observed in the CR1R12 cell line overexpressing the rodent enzyme. Because these cell lines overexpress the respective transporter enzymes, the $IC_{50}$ would be expected to be higher than under in vivo conditions, where far fewer copies of the enzyme would be contained per cell. The other fluorescent marker, Rho, is also retained in the presence of SCH66336 with an $IC_{50}$ ~11 M (FIG. 2).

Example B

SCH66336 is a Slow Substrate for P-gp

We have developed an ATP hydrolysis assay based on phosphate-release determination using membrane microsome preparations (Sarkadi et al., 1992; Shapiro and Ling; 1994; Doige et al., 1992). The method was modified to be carried out in a 96-well microplate. The consumption of ATP was determined by the liberated inorganic orthophosphate, which forms a color complex with molybdate (Chifflet et al., 1988).

CR1R12 cell membranes enriched with the MDR1 gene product transport enzyme were used for preparation of membrane microsomes. Cells were washed with complete Hanks' buffer before being resuspended in 10 ml lysis buffer (Tris-25 HCl, 50 mM; mannitol, 50 mM; EGTA, 2 mM; and dithiothreitol, 2 mM; pH 7.0 at 25° C.) containing protease inhibitors (phenylmethylsulfonyl fluoride, 1 mM; aprotinin, 10 µg/ml; leupeptin, 10 µg/ml). All subsequent steps were performed at 4° C. The cells were lysed by nitrogen cavitation (Parr Instrument Co., Moline, Ill.) at 500 psi for 15 min twice. Nuclei and mitochondria were sedimented by centrifugation at 4000×g for 10 min. The microsomal membrane fraction was then sedimented by centrifugation at 100,000×g for 60 min. The pellet was resuspended in 0.25 M sucrose buffer (10 mM Tris-HCl, 1 mM EDTA, pH7.5) and homogenized using a Potter-Elvehjem homogenizer. Aliquots of membrane microsomes were rapidly frozen and stored at −80 ° C. until analysis.

The microsomes were thawed on ice prior to diluting to 3.5 µg protein per well in ice-cold ATPase buffer (sodium ATP, 3 mM; KCl, 50 mM; $MgSO_4$, 10 mM; dithiothreitol, 3 mM; Tris-HCl, 50 mM; pH 7.0) containing 0.5 mM EGTA (to inhibit Ca-ATPase), 0.5 mM ouabain (to inhibit the Na/K-ATPase), and 3 mM sodium azide (to inhibit the mitochondrial ATPase). The total incubation volume including the various inhibitors was 100 μl. The incubation reaction was initiated by transferring the plate from ice to 37° C. and incubating for 30 min; the reaction was terminated by the addition of 50 μl 12% SDS solution at room temperature, followed by the addition of 50 μl of a mixture solution of (equal volumes) 18% fresh ascorbic acid in 1N HCl and 3% ammonium molybdate in 1 N HCl. After 4 min, 100 μl of a solution of 2% sodium citrate and 2% sodium meta-arsenite in 2% acetic acid was added to fix the color formation. After 30 min incubation at room temperature, the fixed released phosphate was quantitated colorimetrically in a microplate reader (Bio-Tek FL600, VT) at 750 nm. The respective values for background with ATPase assay buffer alone were obtained in parallel and subtracted from the values for experimental samples. By comparison to a standard curve, the amount of phosphate released—and hence ATP consumed—was quantified. Water-insoluble drugs were dissolved in methanol; the maximum methanol concentration (2% v/v) was shown not to affect the ATPase activity.

Results

As ATP is consumed at a purported rate of about 1 per transport event (Eytan et al., 1996; Ambudkar et al, 1997; Stein 1997; Shapiro et al, 1998) the hydrolysis of ATP represents transport function turnover rate or activity assay. Most known ligands of P-gp cause increases in ATP hydrodysis. (Table 1 below). The presence of SCH66336 caused a concentration-dependent decrease in the rate of ATP hydrolysis relative to baseline rate, which indicates that it is a comparatively slow substrate for P-gp (FIG. 3). The $K_m$ is ~3 M, and the $V_{max}$ is ~28% baseline. The ATP hydrolysis activity assay results are consonant with the transport function inhibition assays (described above).

TABLE 1

Kinetic parameters of ATP hydrolysis for various substrates

|  | Vmax % control | Std. Dev. | $K_m$, μM | Std. Dev. |
| --- | --- | --- | --- | --- |
| Verapamil | 194 | 7 | 22 | 6 |
| Nifedipine | 180 | 7 | 13 | 9 |
| Ketoconazole | 220 | 18 | 2.4 | 1.4 |
| Quinidine | 239 | 9 | 8 | 1.6 |
| Progesterone | 236 | 8 | 7.4 | 2 |
| Daunorubicin | 170 | 17 | 3 | 2 |
| TPP | 365 | 30 | 41 | 17 |

Pharmaceutical Compositions

Inert, pharmaceutically acceptable carriers used for preparing pharmaceutical compositions of the P-gp inhibitors and the chemotherapeutic agents described herein can be either solid or liquid. Solid preparations include powders, tablets, dispersible granules, capsules, cachets and suppositories. The powders and tablets may comprise from about 5 to about 70% active ingredient. Suitable solid carriers are known in the art, e.g., magnesium carbonate, magnesium stearate, talc, sugar, and/or lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into conveniently sized molds, allowed to cool and thereby solidify.

Liquid preparations include solutions, suspensions and emulsions. As an example may be mentioned water or water-propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The P-gp inhibitors and the chemotherapeutic agents described herein may also be deliverable transdermally. The transdermal compositions can take the form of creams, lotions, aerosols and/or emulsions and can be included in a transdermal patch of the matrix or reservoir type as are conventional in the art for this purpose.

Preferably the compounds are administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, preferably from about 1 mg to 300 mg, more preferably 10 mg to 200 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the P-gp inhibitors and the chemotherapeutic agents and/or radiation therapy will be regulated according to the judgment of the attending clinician (physician) considering such factors as age, condition and size of the patient as well as severity of the disease being treated. A dosage regimen of the P-gp inhibitors can be oral administration of from 10 mg to 2000 mg/day, preferably 10 to 1000 mg/day, more preferably 50 to 600 mg/day, in two to four (preferably two) divided doses, to block tumor growth. In a preferred embodiment, in cases where the P-GP inhibitor is a fused-ring tricyclic benzocycloheptapyridine, the preferred dosage of the inhibitor is oral administration of from 50 to 600 mg/day, more preferably 50 to 400 mg/day, in two divided doses. Intermittant therapy (e.g., one week out of three weeks or three out of four weeks) may also be used.

The chemotherapeutic agent can be administered according to therapeutic protocols well known in the art. It will be apparent to those skilled in the art that the administration of the chemotherapeutic agent can be varied depending on the disease being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

In a preferred example of combination therapy in the treatment [of pancreatic cancer], the P-gp inhibitor is SCH66336, as identified previously, administered orally in a range of from 50 to 400 mg/day, in two divided doses, on a continuous dosing regimen; and the antineoplastic agent is gemcitabine administered at a dosage of from 750 to 1350 mg/m² weekly for three out of four weeks during the course of treatment.

In a preferred example of combination therapy in the treatment [of lung cancer], the P-gp inhibitor is SCH66336, as identified previously, administered orally in a range of from 50 to 400 mg/day, in two divided doses, on a continuous dosing regimen; and the antineoplastic agent is paclitaxel administered at a dosage of from 65 to 175 mg/m² once every three weeks.

In a preferred example of combination therapy in the treatment of [gliomas], the P-gp inhibitor is SCH66336, as identified previously, administered orally in a range of from 50 to 400 mg/day, in two divided doses; and the antineoplastic agent is temozolomide administered at a dosage of from 100 to 250 mg/m².

In another example of combination therapy, the P-gp inhibitor is SCH66336, as identified previously, administered orally in a range of from 50 to 400 mg/day, in two divided doses, on a continuous dosing regimen; and the antineoplastic agent is 5-Fluorouracil (5-FU) administered either at a dosage of 500 mg/m² per week (once a week), or at a dosage of 200–300 mg/m² per day in the case of continuous infusion of the 5-FU. In the case of 5-FU administration on a weekly injection, 5-FU may be administered in combination with a foliate agonist (e.g., Leucovoran (at a dosage of 20 mg/m²/week).

In the methods of this invention, a P-gp inhibitor is administered concurrently or sequentially with a chemotherapeutic agent. Thus, it is not necessary that, for example, the chemotherapeutic agent and the P-gp inhibitor should be administered simultaneously or essentially simultaneously. The advantage of a simultaneous or essentially simultaneous administration is well within the determination of the skilled clinician.

Also, in general, the P-gp inhibitor and the chemotherapeutic agent do not have to be administered in the same pharmaceutical composition, and may, because of different physical and chemical characteristics, have to be administered by different routes. For example, the P-gp inhibitor may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of P-gp inhibitor, and chemotherapeutic agent and/or radiation will depend upon the diagnosis of the attending physicians and their judgement of the condition of the patient and the appropriate treatment protocol.

The P-gp inhibitor, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent to be administered in conjunction (i.e., within a single treatment protocol) with the P-gp inhibitor.

If the P-gp inhibitor and the chemotherapeutic agent are not administered simultaneously or essentially simultaneously, then the initial order of administration of the P-gp inhibitor, and the chemotherapeutic agent, may not be important. Thus, the P-gp inhibitor may be administered first followed by the administration of the chemotherapeutic agent; or the chemotherapeutic agent may be administered first followed by the administration of the P-gp inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent may be administered first, especially if it is a cytotoxic agent, and then the treatment continued with the administration of the P-gp inhibitor followed, where determined advantageous, by the administration of the chemotherapeutic agent, and so on until the treatment protocol is complete.

Thus, in accordance with experience and knowledge, the practising physician can modify each protocol for the administration of a component (therapeutic agent—i.e., P-gp inhibitor or chemotherapeutic agent) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radio-logical studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The following are examples (Examples 1–4) of capsule formulations for the P-gp Inhibitory Compound:

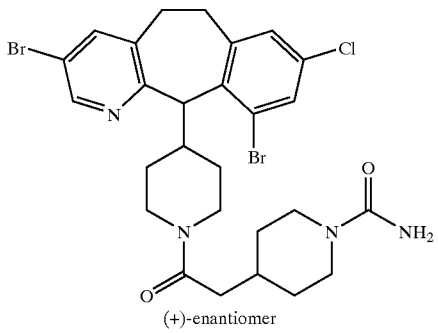

(+)-enantiomer

Examples 1 and 2

Capsule Formulation

| Composition | Example 1 mg/capsule | Example 2 mg/capsule | % Composition |
|---|---|---|---|
| Solid Solution | 100 | 400.0 | 84.2 |
| Silicon Dioxide NF[1] | 0.625 | 2.5 | 0.5 |
| Magnesium Stearate NF[2] | 0.125 | 0.5 | 0.1 |
| Croscarmellose Sodium NF | 11.000 | 44.0 | 9.3 |
| Pluronic F68 NF | 6.250 | 25.0 | 5.3 |
| Silicon Dioxide NF[3] | 0.625 | 2.5 | 0.5 |
| Magnesium Stearate NF[4] | 0.125 | 0.5 | 0.1 |
| TOTAL | 118.750 | 475.00 | |
| Capsule size | No. 4 | No. 0 | |

Method (Examples 1 and 2)

Preparation of Solid Solution

| Composition | g/batch | % Composition |
|---|---|---|
| P-gp Inhibitory Compound | 80 | 33.3 |
| Povidone NF K29/32 | 160 | 66.6 |
| Methylene Chloride | 5000 mL | evaporates |

Crystalline P-gp Inhibitory Compound and the povidone were dissolved in methylene chloride. The solution was dried using a suitable solvent spray dryer. The residue was then reduced to fine particles by grinding. The powder was then passed through a 30 mesh screen. The powder was found to be amorphous by x-ray analysis.

The solid solid solution, silicon dioxide[1] and magnesium stearate[2] were mixed in a suitable mixer for 10 minutes. The mixture is compacted using a suitable roller compactor and milled using a suitable mill fitted with 30 mesh screen. Croscarmellose sodium, Pluronic F68 and silicon dioxide[3] are added to the milled mixture and mixed further for 10 minutes. A premix was made with magnesium stearate[4] and equal portions of the mixture. The premix was added to the remainder of the mixture and mixed for 5 minutes. the mixture was encapsulated in hard shell gelatin capsule shells.

Examples 3 and 4

Capsule Formulation

| Composition | Example 3 mg/capsule | Example 4 mg/capsule | % Composition |
|---|---|---|---|
| Solid Solution | 400 | 200.0 | 80.0 |
| Silicon Dioxide NF[1] | 3.75 | 1.875 | 0.75 |
| Magnesium Stearate NF[2] | 0.125 | 0.625 | 0.25 |
| Croscarmellose Sodium NF | 40.00 | 20.00 | 8.0 |
| Pluronic F68 NF | 50.00 | 25.00 | 10 |
| Silicon Dioxide NF[3] | 3.75 | 1.875 | 0.75 |
| Magnesium Stearate NF[4] | 1.25 | 0.625 | 0.25 |
| TOTAL | 500.00 | 250.00 | |
| Capsule size | No. 0 | No. 2 | |

Method Examples 3 and 4

Preparation of Solid Solution

| Composition | g/batch | % Composition |
|---|---|---|
| P-gp Inhibitory Compound | 15 | 50 |
| Povidone NF K29/32 | 15 | 50 |
| Methylene Chloride | 140 mL | evaporates |
| Methanol | 60 mL | evaporates |

For information on formulations, reference can also be made to U.S. patent application Ser. Nos. 08/997,168, now abandoned, and 60/068,387 (filed Dec. 22, 1997), incorporated herein by reference.

Crystalline P-gp Inhibitory Compound and the povidone were dissolved in a mixture of methylene chloride and methanol. The solution was dried using a suitable solvent spray dryer. The residue was then reduced to fine particles by grinding. The powder was then passed through a 30 mesh screen. The powder was found to be amorphous by x-ray analysis.

The solid solid solution, silicon dioxide[1] and magnesium stearate[2] were mixed in a suitable mixer for 10 minutes. The mixture is compacted using a suitable roller compactor and milled using a suitable mill fitted with 30 mesh screen. Croscarmellose sodium, Pluronic F68 and silicon dioxide[3] are added to the milled mixture and mixed further for 10 minutes. A premix was made with magnesium stearate[4] and equal portions of the mixture. The premix was added to the remainder of the mixture and mixed for 5 minutes. The mixture was encapsulated in hard shell gelatin capsule shells.

The scope of the invention in its pharmaceutical composition aspect is not to be limited by the examples provided.

All documents (e.g., publications and patent applications) cited herein are incorporated by reference to the same extent as if each individual document was specifically and individually indicated to be incorporated by reference.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A method of treating multidrug resistance of refractory tumor cells in a patient in need of such treatment, said method comprising administering, concurrently or sequentially, an effective amount of (1) the P-gp inhibitor:
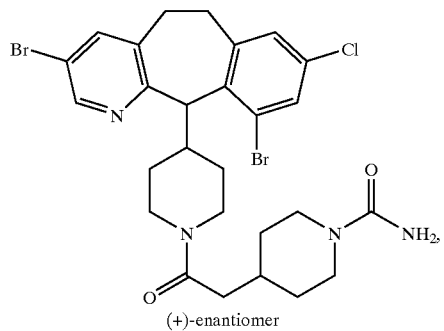
(+)-enantiomer
and (2) an antineoplastic agent to said patient.
* * * * *